(12) United States Patent
Rusanescu

(10) Patent No.: US 10,398,760 B2
(45) Date of Patent: Sep. 3, 2019

(54) METHOD OF TREATING PAIN USING AGENTS THAT PROMOTE NEURONAL DIFFERENTIATION

(71) Applicant: Gabriel Rusanescu, Somerville, MA (US)

(72) Inventor: Gabriel Rusanescu, Somerville, MA (US)

( * ) Notice: Subject to any disclaimer, the term of this patent is extended or adjusted under 35 U.S.C. 154(b) by 82 days.

(21) Appl. No.: 15/249,402

(22) Filed: Aug. 27, 2016

(65) Prior Publication Data

US 2018/0000897 A1    Jan. 4, 2018

Related U.S. Application Data

(60) Provisional application No. 62/356,615, filed on Jun. 30, 2016.

(51) Int. Cl.
| | |
|---|---|
| *A61K 38/16* | (2006.01) |
| *A61K 38/17* | (2006.01) |
| *A61K 38/18* | (2006.01) |
| *C07K 14/475* | (2006.01) |
| *A61K 38/05* | (2006.01) |
| *A61K 31/506* | (2006.01) |
| *A61K 31/198* | (2006.01) |
| *A61K 31/352* | (2006.01) |
| *A61K 31/7048* | (2006.01) |

(52) U.S. Cl.
CPC .......... *A61K 38/185* (2013.01); *A61K 31/198* (2013.01); *A61K 31/352* (2013.01); *A61K 31/506* (2013.01); *A61K 31/7048* (2013.01); *A61K 38/05* (2013.01)

(58) Field of Classification Search
None
See application file for complete search history.

(56) References Cited

U.S. PATENT DOCUMENTS

2013/0196908 A1*   8/2013   Toll ................. A61K 9/0043
                                                           514/8.4

OTHER PUBLICATIONS

Frank et al. (1997). Experimental Neurology. 145:62-70.*

* cited by examiner

*Primary Examiner* — Christine J Saoud
*Assistant Examiner* — Jon M Lockard

(57) ABSTRACT

The present invention is based on the seminal concept of treating pain by promoting neuronal differentiation. The invention provides a method of treating pain utilizing agents that induce neuronal differentiation by activating specific receptors. The invention also provides a method of screening of agents for the purpose of use in treating pain, based on their neuronal differentiation activity.

3 Claims, 10 Drawing Sheets
Specification includes a Sequence Listing.

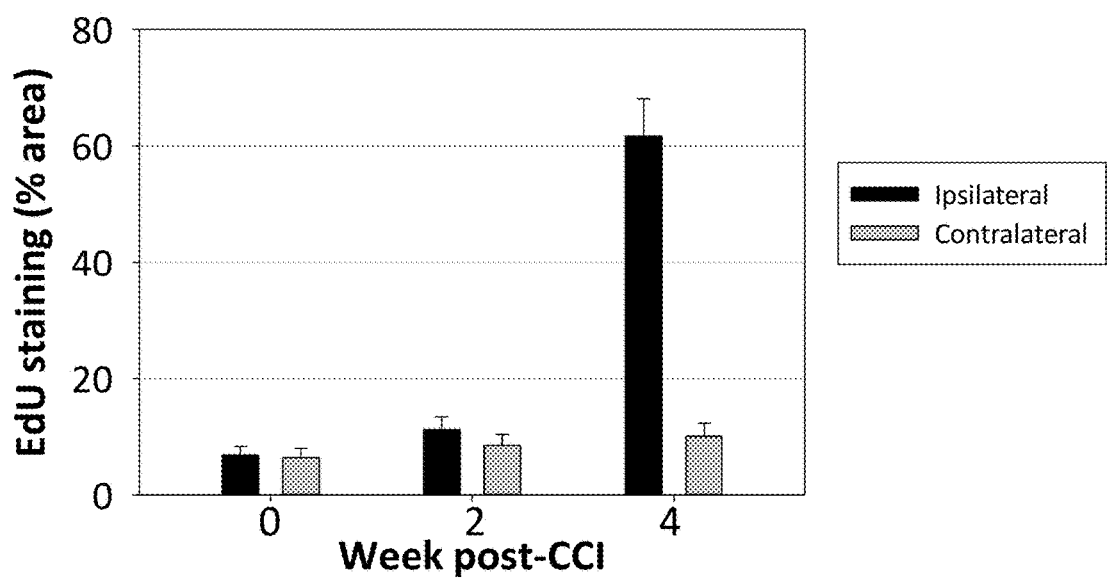
Figure 1: EdU staining shows increased number of proliferating cells in the spinal cord ipsilateral to peripheral nerve injury Figure 2 - Nestin expression is increased in the spinal cord dorsal horn ipsilateral to peripheral nerve injury
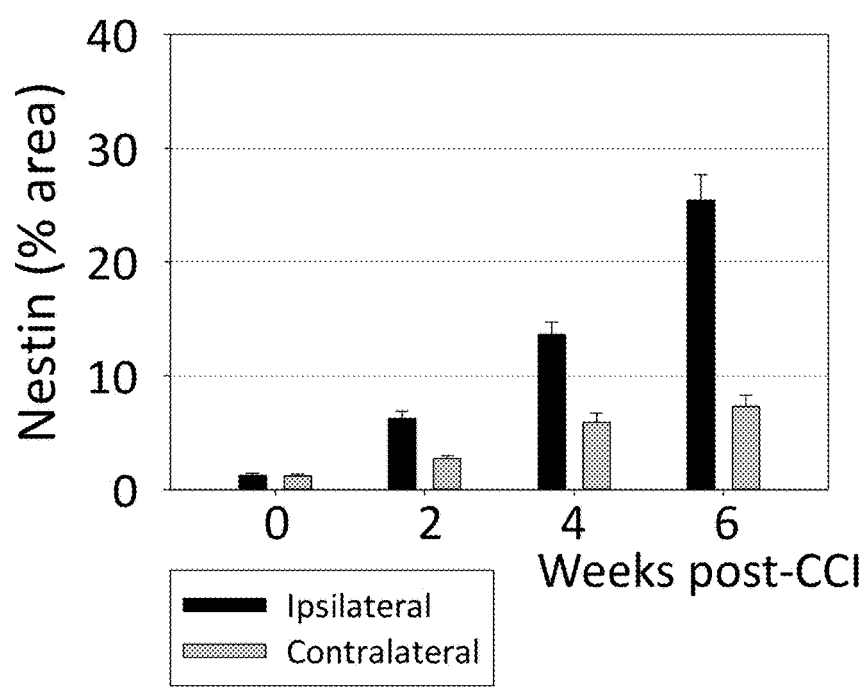

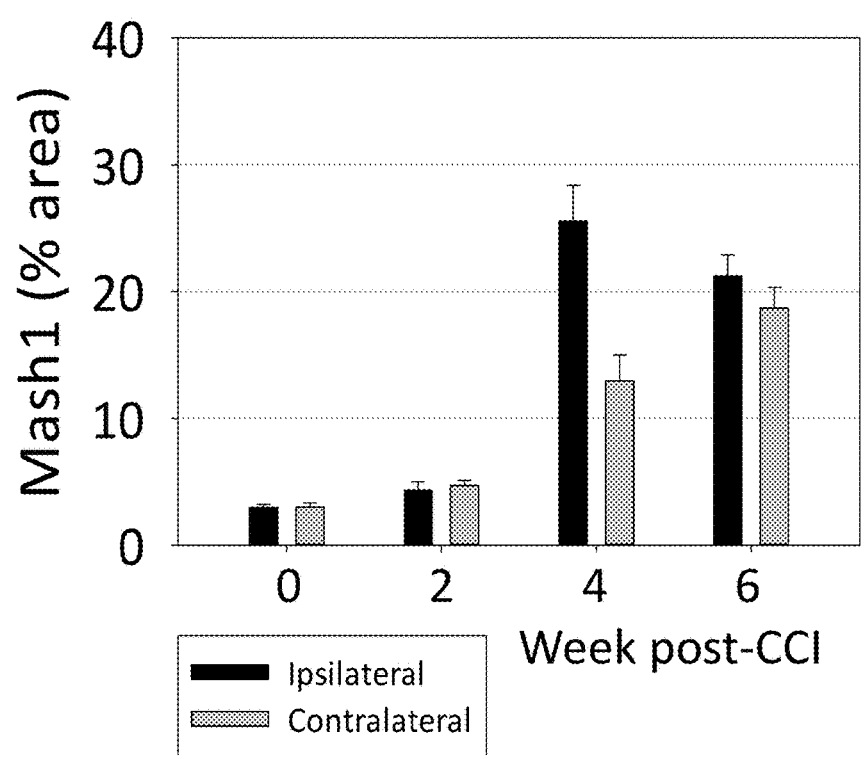
Figure 3 - Mash1 expression is increased in the spinal cord ipsilateral to peripheral nerve injury Figure 4 - Doublecortin expression is increased in the spinal cord ipsilateral to peripheral nerve injury
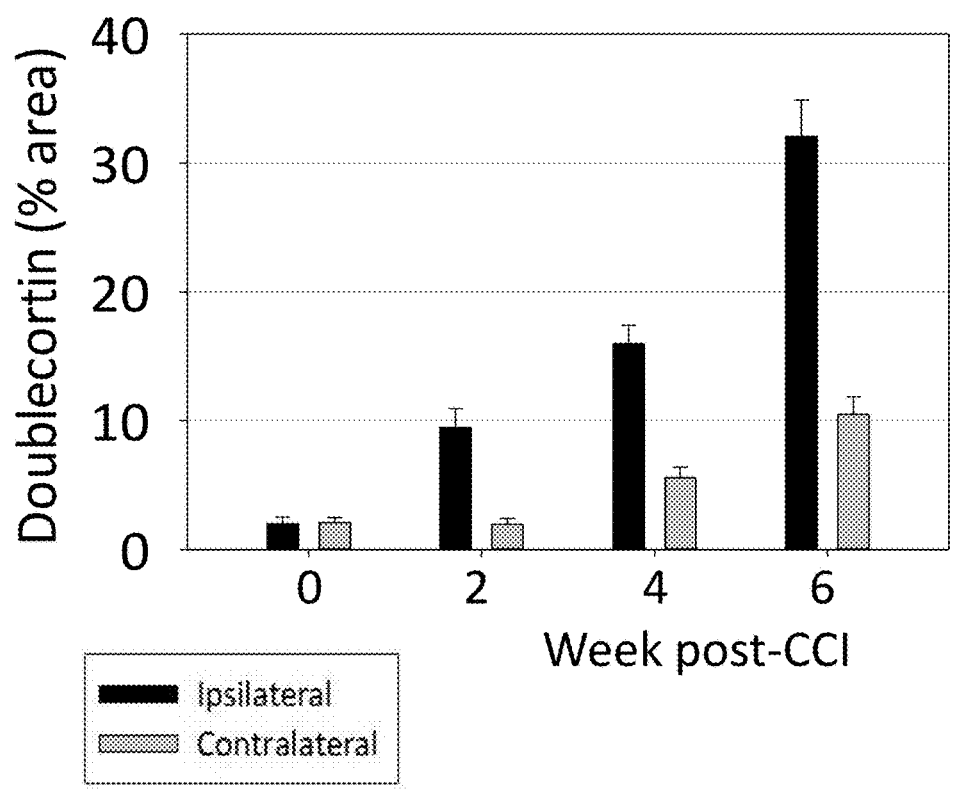

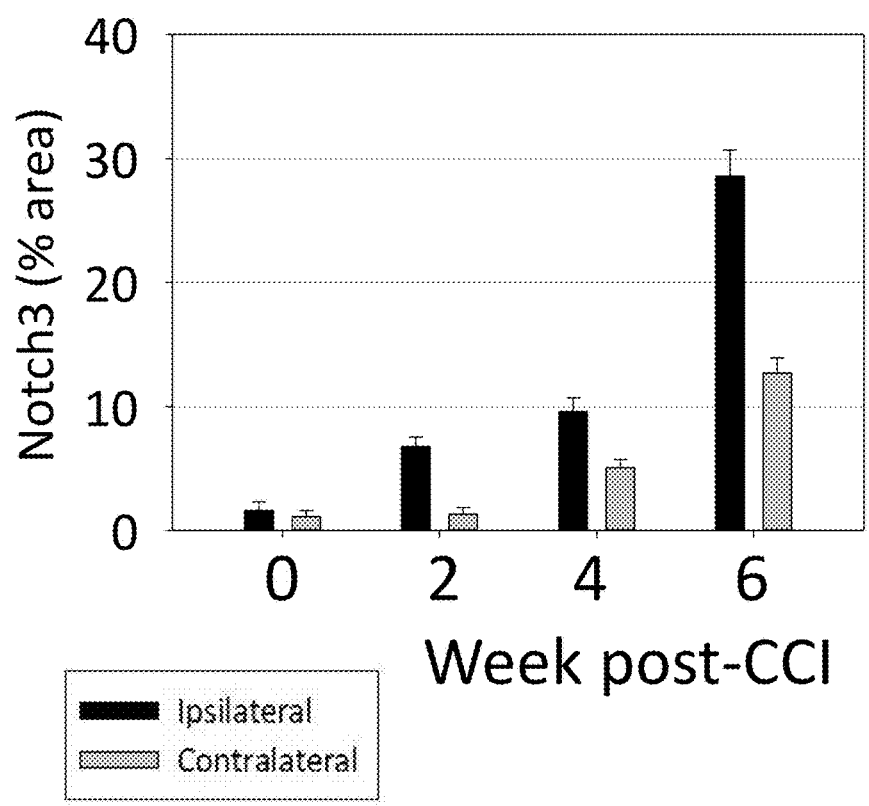
Figure 5 - Notch3 expression is increased in the spinal cord ipsilateral to peripheral nerve injury

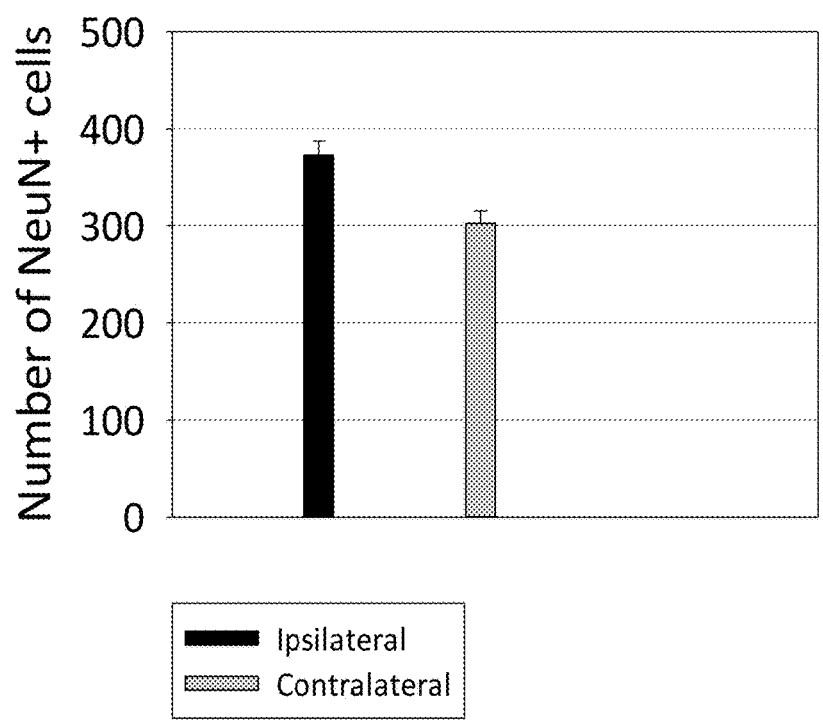
Figure 6 - The number of Neu-positive mature neurons is increased in the ipsilateral spinal cord layers 1-2, after peripheral nerve injury

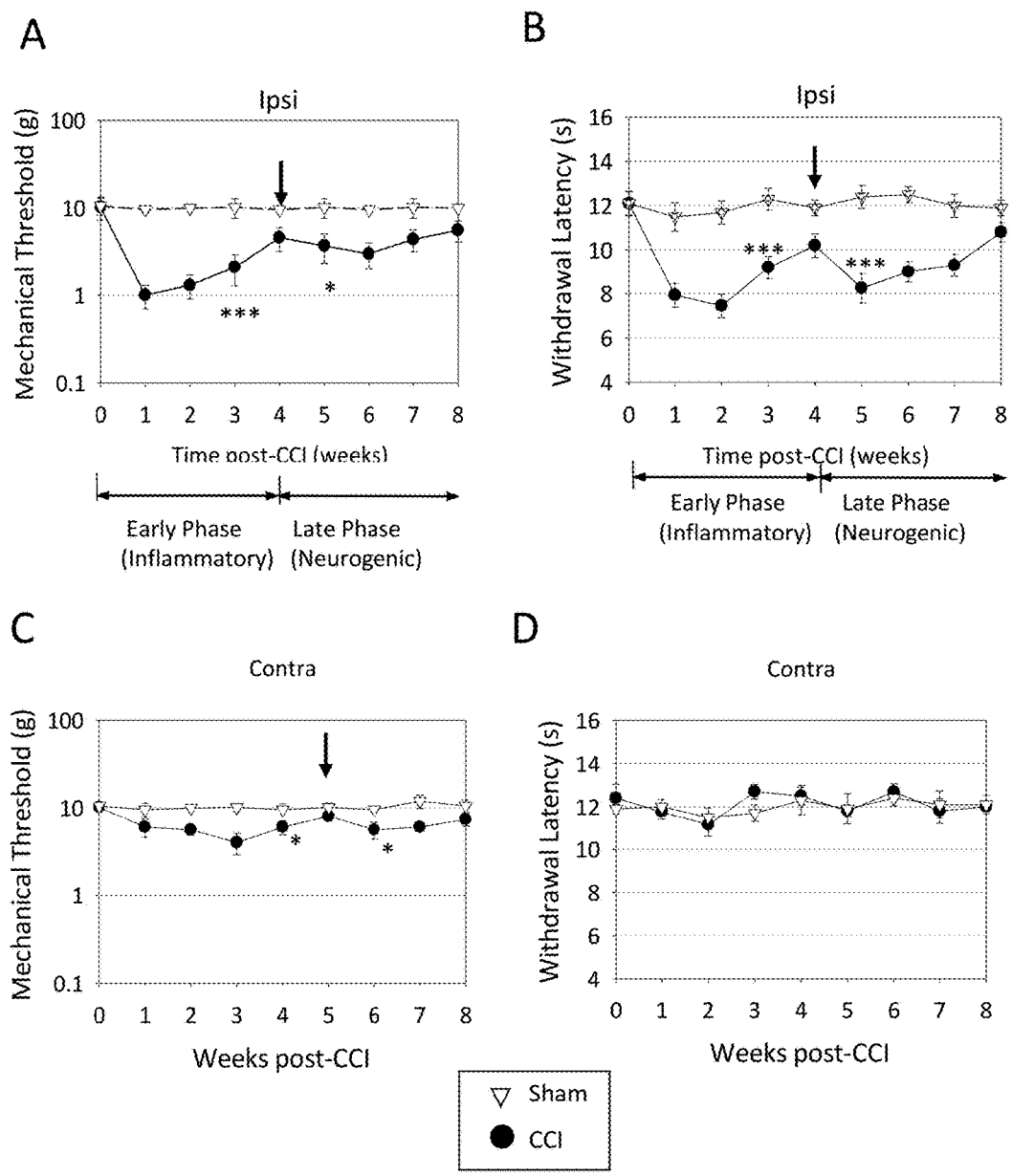
Figure 7 - Pain induced by peripheral nerve injury has a long-term neurogenesis-dependent phase.

Figure 8 - Pain sensitivity is dependent on the level of spinal cord adult neurogenesis.
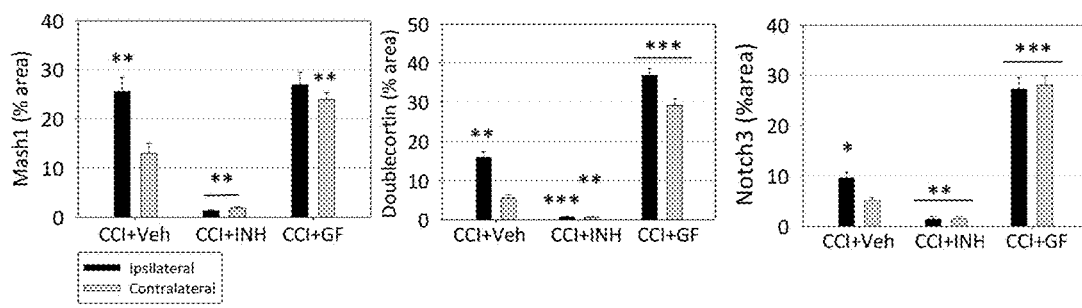
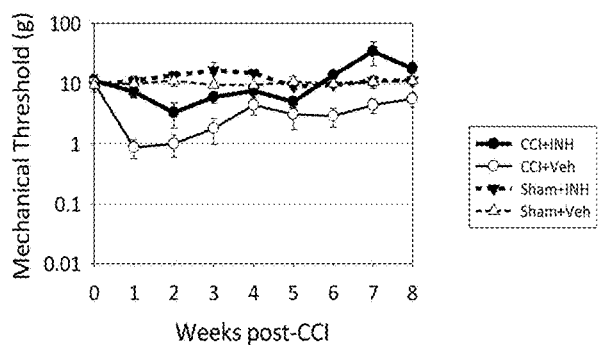
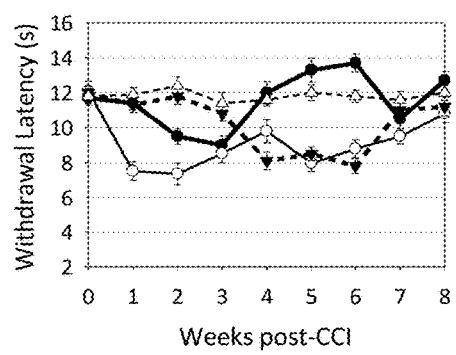
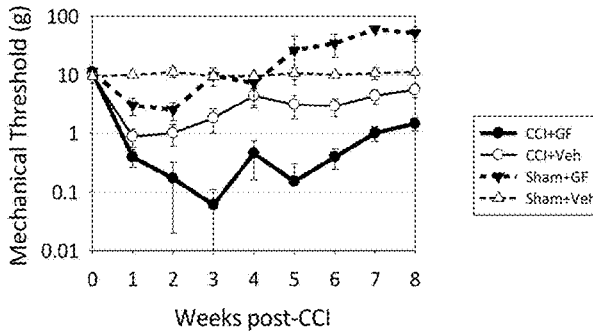
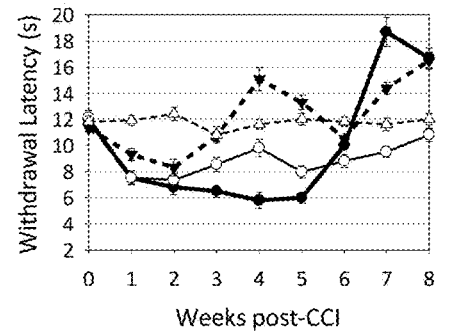

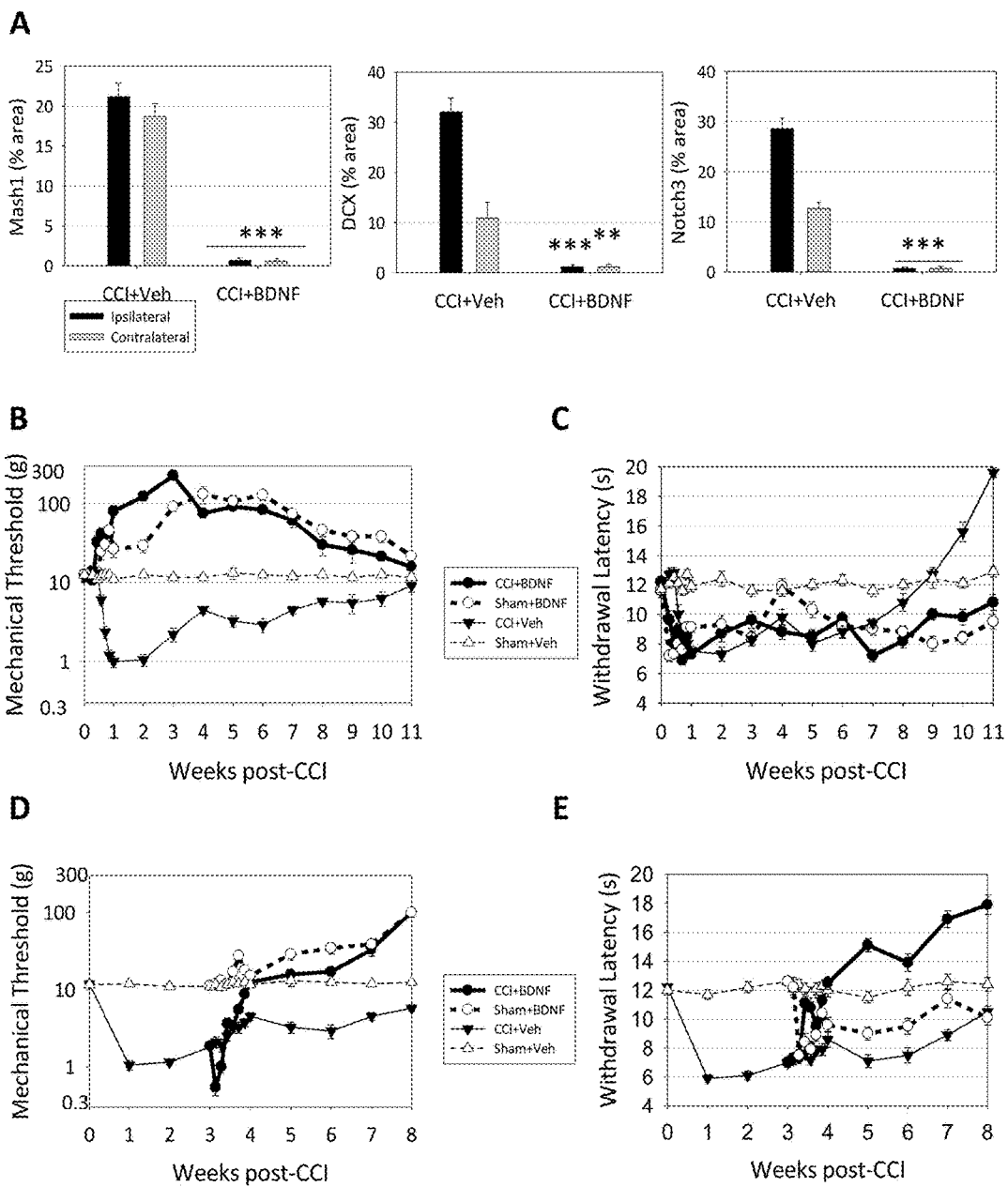
Figure 9 - BDNF reduces long-term pain sensitivity by promoting the differentiation of spinal cord immature neurons.

Figure 10 - 7,8 Dihidroxyflavone reduces long-term pain sensitivity by promoting the differentiation of spinal cord immature neurons.
A
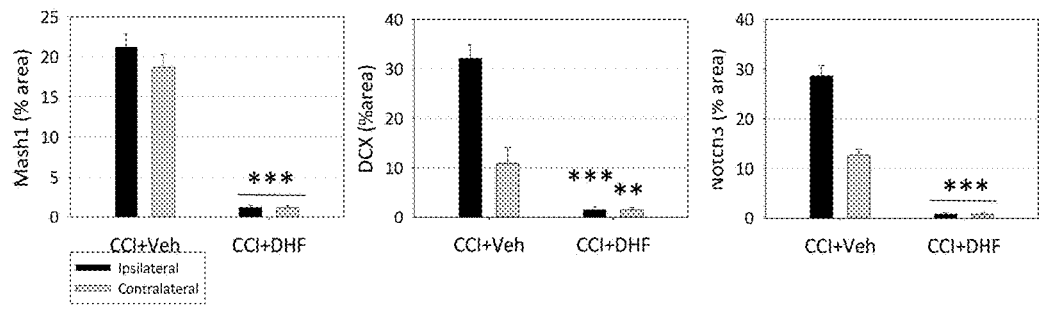
B
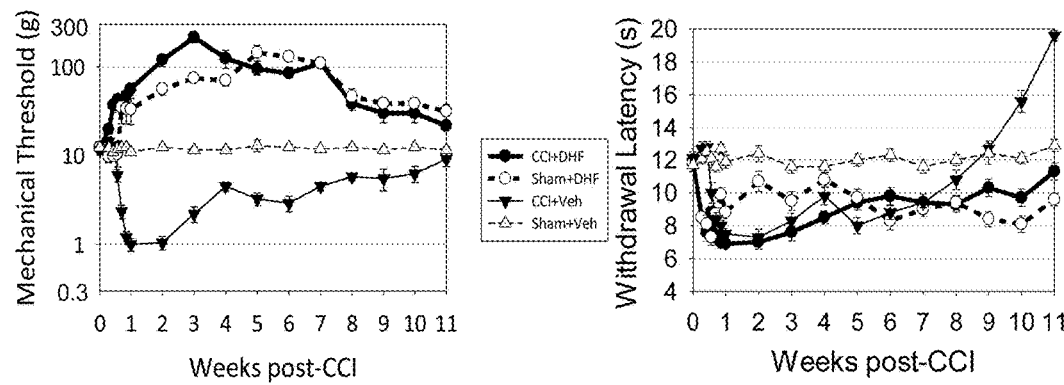
C
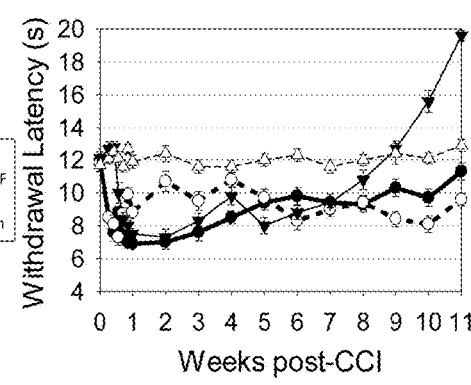
D
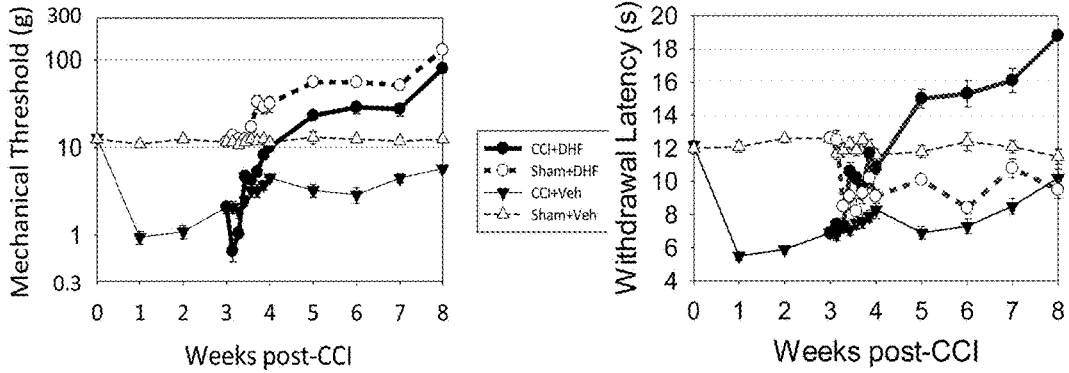
E
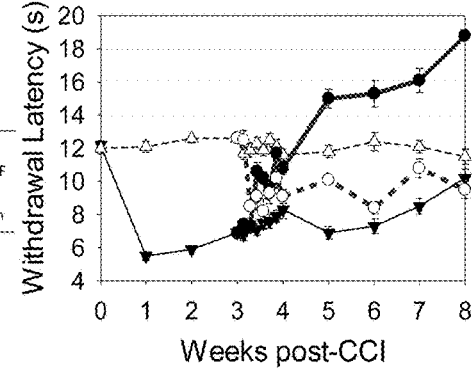

SEQUENCE LISTING

```
<160> NUMBER OF SEQ ID NOS: 54

<210> SEQ ID NO 1
<211> LENGTH: 119
<212> TYPE: PRT
<213> ORGANISM: Homo sapiens
<300> PUBLICATION INFORMATION:
<308> DATABASE ACCESSION NUMBER: P23560
<309> DATABASE ENTRY DATE: 2016-07-06
<313> RELEVANT RESIDUES IN SEQ ID NO: (129)..(247)

<400> SEQUENCE: 1

His Ser Asp Pro Ala Arg Arg Gly Glu Leu Ser Val Cys Asp Ser Ile
1               5                   10                  15
```

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg
        115

<210> SEQ ID NO 2
<211> LENGTH: 120
<212> TYPE: PRT
<213> ORGANISM: Homo sapiens
<300> PUBLICATION INFORMATION:
<308> DATABASE ACCESSION NUMBER: P01138
<309> DATABASE ENTRY DATE: 2016-07-06
<313> RELEVANT RESIDUES IN SEQ ID NO: (122)..(241)

<400> SEQUENCE: 2

Ser Ser Ser His Pro Ile Phe His Arg Gly Glu Phe Ser Val Cys Asp
1               5                   10                  15

Ser Val Ser Val Trp Val Gly Asp Lys Thr Thr Ala Thr Asp Ile Lys
            20                  25                  30

Gly Lys Glu Val Met Val Leu Gly Glu Val Asn Ile Asn Asn Ser Val
        35                  40                  45

Phe Lys Gln Tyr Phe Phe Glu Thr Lys Cys Arg Asp Pro Asn Pro Val
50                  55                  60

Asp Ser Gly Cys Arg Gly Ile Asp Ser Lys His Trp Asn Ser Tyr Cys
65                  70                  75                  80

Thr Thr Thr His Thr Phe Val Lys Ala Leu Thr Met Asp Gly Lys Gln
                85                  90                  95

Ala Ala Trp Arg Phe Ile Arg Ile Asp Thr Ala Cys Val Cys Val Leu
            100                 105                 110

Ser Arg Lys Ala Val Arg Arg Ala
        115                 120

<210> SEQ ID NO 3
<211> LENGTH: 119
<212> TYPE: PRT
<213> ORGANISM: Homo sapiens
<300> PUBLICATION INFORMATION:
<308> DATABASE ACCESSION NUMBER: P20783
<309> DATABASE ENTRY DATE: 2016-07-06
<313> RELEVANT RESIDUES IN SEQ ID NO: (139)..(257)

<400> SEQUENCE: 3

Tyr Ala Glu His Lys Ser His Arg Gly Glu Tyr Ser Val Cys Asp Ser
1               5                   10                  15

Glu Ser Leu Trp Val Thr Asp Lys Ser Ser Ala Ile Asp Ile Arg Gly
            20                  25                  30

His Gln Val Thr Val Leu Gly Glu Ile Lys Thr Gly Asn Ser Pro Val
        35                  40                  45

Lys Gln Tyr Phe Tyr Glu Thr Arg Cys Lys Glu Ala Arg Pro Val Lys

Asn Gly Cys Arg Gly Ile Asp Asp Lys His Trp Asn Ser Gln Cys Lys
65                  70                  75                  80

Thr Ser Gln Thr Tyr Val Arg Ala Leu Thr Ser Glu Asn Asn Lys Leu
                85                  90                  95

Val Gly Trp Arg Trp Ile Arg Ile Asp Thr Ser Cys Val Cys Ala Leu
            100                 105                 110

Ser Arg Lys Ile Gly Arg Thr
            115

<210> SEQ ID NO 4
<211> LENGTH: 130
<212> TYPE: PRT
<213> ORGANISM: Homo sapiens
<300> PUBLICATION INFORMATION:
<308> DATABASE ACCESSION NUMBER: P34130
<309> DATABASE ENTRY DATE: 2016-07-06
<313> RELEVANT RESIDUES IN SEQ ID NO: (81)..(210)

<400> SEQUENCE: 4

Gly Val Ser Glu Thr Ala Pro Ala Ser Arg Arg Gly Glu Leu Ala Val
1               5                   10                  15

Cys Asp Ala Val Ser Gly Trp Val Thr Asp Arg Arg Thr Ala Val Asp
                20                  25                  30

Leu Arg Gly Arg Glu Val Glu Val Leu Gly Glu Val Pro Ala Ala Gly
            35                  40                  45

Gly Ser Pro Leu Arg Gln Tyr Phe Phe Glu Thr Arg Cys Lys Ala Asp
        50                  55                  60

Asn Ala Glu Glu Gly Gly Pro Gly Ala Gly Gly Gly Cys Arg Gly
65                  70                  75                  80

Val Asp Arg Arg His Trp Val Ser Glu Cys Lys Ala Lys Gln Ser Tyr
                85                  90                  95

Val Arg Ala Leu Thr Ala Asp Ala Gln Gly Arg Val Gly Trp Arg Trp
            100                 105                 110

Ile Arg Ile Asp Thr Ala Cys Val Cys Thr Leu Leu Ser Arg Thr Gly
        115                 120                 125

Arg Ala
    130

<210> SEQ ID NO 5
<211> LENGTH: 200
<212> TYPE: PRT
<213> ORGANISM: Homo sapiens
<300> PUBLICATION INFORMATION:
<308> DATABASE ACCESSION NUMBER: P26441
<309> DATABASE ENTRY DATE: 2016-07-06
<313> RELEVANT RESIDUES IN SEQ ID NO: (1)..(200)

<400> SEQUENCE: 5

Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
                20                  25                  30

Ala Leu Thr Glu Ser Tyr Val Lys His Gln Gly Leu Asn Lys Asn Ile
            35                  40                  45

Asn Leu Asp Ser Ala Asp Gly Met Pro Val Ala Ser Thr Asp Gln Trp
        50                  55                  60

Ser Glu Leu Thr Glu Ala Glu Arg Leu Gln Glu Asn Leu Gln Ala Tyr
65                  70                  75                  80

```
Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
    130                 135                 140

Asn Val Gly Asp Gly Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys Lys Met
        195                 200

<210> SEQ ID NO 6
<211> LENGTH: 134
<212> TYPE: PRT
<213> ORGANISM: Homo sapiens
<300> PUBLICATION INFORMATION:
<308> DATABASE ACCESSION NUMBER: P39905
<309> DATABASE ENTRY DATE: 2016-07-06
<313> RELEVANT RESIDUES IN SEQ ID NO: (78)..(211)

<400> SEQUENCE: 6

Ser Pro Asp Lys Gln Met Ala Val Leu Pro Arg Arg Glu Arg Asn Arg
1               5                   10                  15

Gln Ala Ala Ala Ala Asn Pro Glu Asn Ser Arg Gly Lys Gly Arg Arg
            20                  25                  30

Gly Gln Arg Gly Lys Asn Arg Gly Cys Val Leu Thr Ala Ile His Leu
        35                  40                  45

Asn Val Thr Asp Leu Gly Leu Gly Tyr Glu Thr Lys Glu Glu Leu Ile
    50                  55                  60

Phe Arg Tyr Cys Ser Gly Ser Cys Asp Ala Ala Glu Thr Thr Tyr Asp
65                  70                  75                  80

Lys Ile Leu Lys Asn Leu Ser Arg Asn Arg Arg Leu Val Ser Asp Lys
                85                  90                  95

Val Gly Gln Ala Cys Cys Arg Pro Ile Ala Phe Asp Asp Asp Leu Ser
            100                 105                 110

Phe Leu Asp Asp Asn Leu Val Tyr His Ile Leu Arg Lys His Ser Ala
        115                 120                 125

Lys Arg Cys Gly Cys Ile
    130

<210> SEQ ID NO 7
<211> LENGTH: 113
<212> TYPE: PRT
<213> ORGANISM: Homo sapiens
<300> PUBLICATION INFORMATION:
<308> DATABASE ACCESSION NUMBER: Q5T4W7
<309> DATABASE ENTRY DATE: 2016-07-06
<313> RELEVANT RESIDUES IN SEQ ID NO: (108)..(220)

<400> SEQUENCE: 7

Ala Gly Gly Pro Gly Ser Arg Ala Arg Ala Ala Gly Ala Arg Gly Cys
1               5                   10                  15
```

```
Arg Leu Arg Ser Gln Leu Val Pro Val Arg Ala Leu Gly Gly His
             20                  25                  30

Arg Ser Asp Glu Leu Val Arg Phe Arg Phe Cys Ser Gly Ser Cys Arg
         35                  40                  45

Arg Ala Arg Ser Pro His Asp Leu Ser Leu Ala Ser Leu Leu Gly Ala
 50                  55                  60

Gly Ala Leu Arg Pro Pro Gly Ser Arg Pro Val Ser Gln Pro Cys
 65                  70                  75                  80

Cys Arg Pro Thr Arg Tyr Glu Ala Val Ser Phe Met Asp Val Asn Ser
             85                  90                  95

Thr Trp Arg Thr Val Asp Arg Leu Ser Ala Thr Ala Cys Gly Cys Leu
            100                 105                 110

Gly
```

```
<210> SEQ ID NO 8
<211> LENGTH: 102
<212> TYPE: PRT
<213> ORGANISM: Homo sapiens
<300> PUBLICATION INFORMATION:
<308> DATABASE ACCESSION NUMBER: Q99748
<309> DATABASE ENTRY DATE: 2016-07-06
<313> RELEVANT RESIDUES IN SEQ ID NO: (96)..(197)

<400> SEQUENCE: 8

Ala Arg Leu Gly Ala Arg Pro Cys Gly Leu Arg Glu Leu Glu Val Arg
 1               5                  10                  15

Val Ser Glu Leu Gly Leu Gly Tyr Ala Ser Asp Glu Thr Val Leu Phe
             20                  25                  30

Arg Tyr Cys Ala Gly Ala Cys Glu Ala Ala Ala Arg Val Tyr Asp Leu
         35                  40                  45

Gly Leu Arg Arg Leu Arg Gln Arg Arg Arg Leu Arg Arg Glu Arg Val
     50                  55                  60

Arg Ala Gln Pro Cys Cys Arg Pro Thr Ala Tyr Glu Asp Glu Val Ser
 65                  70                  75                  80

Phe Leu Asp Ala His Ser Arg Tyr His Thr Val His Glu Leu Ser Ala
             85                  90                  95

Arg Glu Cys Ala Cys Val
            100
```

```
<210> SEQ ID NO 9
<211> LENGTH: 135
<212> TYPE: PRT
<213> ORGANISM: Homo sapiens
<300> PUBLICATION INFORMATION:
<308> DATABASE ACCESSION NUMBER: O60542
<309> DATABASE ENTRY DATE: 2016-07-06
<313> RELEVANT RESIDUES IN SEQ ID NO: (22)..(156)

<400> SEQUENCE: 9

Trp Gly Pro Asp Ala Arg Gly Val Pro Val Ala Asp Gly Glu Phe Ser
 1               5                  10                  15

Ser Glu Gln Val Ala Lys Ala Gly Gly Thr Trp Leu Gly Thr His Arg
             20                  25                  30

Pro Leu Ala Arg Leu Arg Arg Ala Leu Ser Gly Pro Cys Gln Leu Trp
         35                  40                  45

Ser Leu Thr Leu Ser Val Ala Glu Leu Gly Leu Gly Tyr Ala Ser Glu
     50                  55                  60

Glu Lys Val Ile Phe Arg Tyr Cys Ala Gly Ser Cys Pro Arg Gly Ala
 65                  70                  75                  80
```

```
Arg Thr Gln His Gly Leu Ala Leu Ala Arg Leu Gln Gly Gln Gly Arg
                85                  90                  95

Ala His Gly Gly Pro Cys Cys Arg Pro Thr Arg Tyr Thr Asp Val Ala
            100                 105                 110

Phe Leu Asp Asp Arg His Arg Trp Gln Arg Leu Pro Gln Leu Ser Ala
        115                 120                 125

Ala Ala Cys Gly Cys Gly Gly
    130             135

<210> SEQ ID NO 10
<211> LENGTH: 180
<212> TYPE: PRT
<213> ORGANISM: Homo sapiens
<300> PUBLICATION INFORMATION:
<308> DATABASE ACCESSION NUMBER: P15018
<309> DATABASE ENTRY DATE: 2016-07-06
<313> RELEVANT RESIDUES IN SEQ ID NO: (23)..(202)

<400> SEQUENCE: 10

Ser Pro Leu Pro Ile Thr Pro Val Asn Ala Thr Cys Ala Ile Arg His
1               5                   10                  15

Pro Cys His Asn Asn Leu Met Asn Gln Ile Arg Ser Gln Leu Ala Gln
            20                  25                  30

Leu Asn Gly Ser Ala Asn Ala Leu Phe Ile Leu Tyr Tyr Thr Ala Gln
        35                  40                  45

Gly Glu Pro Phe Pro Asn Asn Leu Asp Lys Leu Cys Gly Pro Asn Val
    50                  55                  60

Thr Asp Phe Pro Pro Phe His Ala Asn Gly Thr Glu Lys Ala Lys Leu
65                  70                  75                  80

Val Glu Leu Tyr Arg Ile Val Val Tyr Leu Gly Thr Ser Leu Gly Asn
                85                  90                  95

Ile Thr Arg Asp Gln Lys Ile Leu Asn Pro Ser Ala Leu Ser Leu His
            100                 105                 110

Ser Lys Leu Asn Ala Thr Ala Asp Ile Leu Arg Gly Leu Leu Ser Asn
        115                 120                 125

Val Leu Cys Arg Leu Cys Ser Lys Tyr His Val Gly His Val Asp Val
    130                 135                 140

Thr Tyr Gly Pro Asp Thr Ser Gly Lys Asp Val Phe Gln Lys Lys Lys
145                 150                 155                 160

Leu Gly Cys Gln Leu Leu Gly Lys Tyr Lys Gln Ile Ile Ala Val Leu
                165                 170                 175

Ala Gln Ala Phe
            180

<210> SEQ ID NO 11
<211> LENGTH: 8
<212> TYPE: PRT
<213> ORGANISM: Homo sapiens
<300> PUBLICATION INFORMATION:
<308> DATABASE ACCESSION NUMBER: P01019
<309> DATABASE ENTRY DATE: 2016-07-06
<313> RELEVANT RESIDUES IN SEQ ID NO: (34)..(41)

<400> SEQUENCE: 11

Asp Arg Val Tyr Ile His Pro Phe
1               5

<210> SEQ ID NO 12
<211> LENGTH: 343
```

```
<212> TYPE: PRT
<213> ORGANISM: Homo sapiens
<300> PUBLICATION INFORMATION:
<308> DATABASE ACCESSION NUMBER: P04628
<309> DATABASE ENTRY DATE: 2016-07-06
<313> RELEVANT RESIDUES IN SEQ ID NO: (28)..(370)

<400> SEQUENCE: 12

Ala Asn Ser Ser Gly Arg Trp Trp Gly Ile Val Asn Val Ala Ser Ser
1               5                   10                  15

Thr Asn Leu Leu Thr Asp Ser Lys Ser Leu Gln Leu Val Leu Glu Pro
            20                  25                  30

Ser Leu Gln Leu Leu Ser Arg Lys Gln Arg Arg Leu Ile Arg Gln Asn
        35                  40                  45

Pro Gly Ile Leu His Ser Val Ser Gly Gly Leu Gln Ser Ala Val Arg
    50                  55                  60

Glu Cys Lys Trp Gln Phe Arg Asn Arg Arg Trp Asn Cys Pro Thr Ala
65                  70                  75                  80

Pro Gly Pro His Leu Phe Gly Lys Ile Val Asn Arg Gly Cys Arg Glu
                85                  90                  95

Thr Ala Phe Ile Phe Ala Ile Thr Ser Ala Gly Val Thr His Ser Val
            100                 105                 110

Ala Arg Ser Cys Ser Glu Gly Ser Ile Glu Ser Cys Thr Cys Asp Tyr
        115                 120                 125

Arg Arg Arg Gly Pro Gly Gly Pro Asp Trp His Trp Gly Gly Cys Ser
    130                 135                 140

Asp Asn Ile Asp Phe Gly Arg Leu Phe Gly Arg Glu Phe Val Asp Ser
145                 150                 155                 160

Gly Glu Lys Gly Arg Asp Leu Arg Phe Leu Met Asn Leu His Asn Asn
                165                 170                 175

Glu Ala Gly Arg Thr Thr Val Phe Ser Glu Met Arg Gln Glu Cys Lys
            180                 185                 190

Cys His Gly Met Ser Gly Ser Cys Thr Val Arg Thr Cys Trp Met Arg
        195                 200                 205

Leu Pro Thr Leu Arg Ala Val Gly Asp Val Leu Arg Asp Arg Phe Asp
    210                 215                 220

Gly Ala Ser Arg Val Leu Tyr Gly Asn Arg Gly Ser Asn Arg Ala Ser
225                 230                 235                 240

Arg Ala Glu Leu Leu Arg Leu Glu Pro Glu Asp Pro Ala His Lys Pro
                245                 250                 255

Pro Ser Pro His Asp Leu Val Tyr Phe Glu Lys Ser Pro Asn Phe Cys
            260                 265                 270

Thr Tyr Ser Gly Arg Leu Gly Thr Ala Gly Thr Ala Gly Arg Ala Cys
        275                 280                 285

Asn Ser Ser Ser Pro Ala Leu Asp Gly Cys Glu Leu Leu Cys Cys Gly
    290                 295                 300

Arg Gly His Arg Thr Arg Thr Gln Arg Val Thr Glu Arg Cys Asn Cys
305                 310                 315                 320

Thr Phe His Trp Cys Cys His Val Ser Cys Arg Asn Cys Thr His Thr
                325                 330                 335

Arg Val Leu His Glu Cys Leu
            340

<210> SEQ ID NO 13
<211> LENGTH: 335
<212> TYPE: PRT
```

<213> ORGANISM: Homo sapiens
<300> PUBLICATION INFORMATION:
<308> DATABASE ACCESSION NUMBER: P09544
<309> DATABASE ENTRY DATE: 2016-07-06
<313> RELEVANT RESIDUES IN SEQ ID NO: (26)..(360)

<400> SEQUENCE: 13

```
Ser Trp Trp Tyr Met Arg Ala Thr Gly Gly Ser Arg Val Met Cys
1               5                   10                  15

Asp Asn Val Pro Gly Leu Val Ser Ser Gln Arg Gln Leu Cys His Arg
            20                  25                  30

His Pro Asp Val Met Arg Ala Ile Ser Gln Gly Val Ala Glu Trp Thr
        35                  40                  45

Ala Glu Cys Gln His Gln Phe Arg Gln His Arg Trp Asn Cys Asn Thr
    50                  55                  60

Leu Asp Arg Asp His Ser Leu Phe Gly Arg Val Leu Leu Arg Ser Ser
65                  70                  75                  80

Arg Glu Ser Ala Phe Val Tyr Ala Ile Ser Ser Ala Gly Val Val Phe
                85                  90                  95

Ala Ile Thr Arg Ala Cys Ser Gln Gly Glu Val Lys Ser Cys Ser Cys
            100                 105                 110

Asp Pro Lys Lys Met Gly Ser Ala Lys Asp Ser Lys Gly Ile Phe Asp
        115                 120                 125

Trp Gly Gly Cys Ser Asp Asn Ile Asp Tyr Gly Ile Lys Phe Ala Arg
    130                 135                 140

Ala Phe Val Asp Ala Lys Glu Arg Lys Gly Lys Asp Ala Arg Ala Leu
145                 150                 155                 160

Met Asn Leu His Asn Asn Arg Ala Gly Arg Lys Ala Val Lys Arg Phe
                165                 170                 175

Leu Lys Gln Glu Cys Lys Cys His Gly Val Ser Gly Ser Cys Thr Leu
            180                 185                 190

Arg Thr Cys Trp Leu Ala Met Ala Asp Phe Arg Lys Thr Gly Asp Tyr
        195                 200                 205

Leu Trp Arg Lys Tyr Asn Gly Ala Ile Gln Val Val Met Asn Gln Asp
    210                 215                 220

Gly Thr Gly Phe Thr Val Ala Asn Glu Arg Phe Lys Lys Pro Thr Lys
225                 230                 235                 240

Asn Asp Leu Val Tyr Phe Glu Asn Ser Pro Asp Tyr Cys Ile Arg Asp
                245                 250                 255

Arg Glu Ala Gly Ser Leu Gly Thr Ala Gly Arg Val Cys Asn Leu Thr
            260                 265                 270

Ser Arg Gly Met Asp Ser Cys Glu Val Met Cys Cys Gly Arg Gly Tyr
        275                 280                 285

Asp Thr Ser His Val Thr Arg Met Thr Lys Cys Gly Cys Lys Phe His
    290                 295                 300

Trp Cys Cys Ala Val Arg Cys Gln Asp Cys Leu Glu Ala Leu Asp Val
305                 310                 315                 320

His Thr Cys Lys Ala Pro Lys Asn Ala Asp Trp Thr Thr Ala Thr
                325                 330                 335
```

<210> SEQ ID NO 14
<211> LENGTH: 352
<212> TYPE: PRT
<213> ORGANISM: Homo sapiens
<300> PUBLICATION INFORMATION:
<308> DATABASE ACCESSION NUMBER: Q93097
<309> DATABASE ENTRY DATE: 2016-07-06

<313> RELEVANT RESIDUES IN SEQ ID NO: (40)..(391)

<400> SEQUENCE: 14

```
Gly Leu Ala Cys Leu Leu Leu Leu Leu Thr Leu Pro Ala Arg
1               5                   10                  15

Val Asp Thr Ser Trp Trp Tyr Ile Gly Ala Leu Gly Ala Arg Val Ile
            20                  25                  30

Cys Asp Asn Ile Pro Gly Leu Val Ser Arg Gln Arg Gln Leu Cys Gln
            35                  40                  45

Arg Tyr Pro Asp Ile Met Arg Ser Val Gly Glu Gly Ala Arg Glu Trp
        50                  55                  60

Ile Arg Glu Cys Gln His Gln Phe Arg His Arg Trp Asn Cys Thr
65                  70                  75                  80

Thr Leu Asp Arg Asp His Thr Val Phe Gly Arg Val Met Leu Arg Ser
                    85                  90                  95

Ser Arg Glu Ala Ala Phe Val Tyr Ala Ile Ser Ser Ala Gly Val Val
                100                 105                 110

His Ala Ile Thr Arg Ala Cys Ser Gln Gly Glu Leu Ser Val Cys Ser
            115                 120                 125

Cys Asp Pro Tyr Thr Arg Gly Arg His His Asp Gln Arg Gly Asp Phe
130                 135                 140

Asp Trp Gly Gly Cys Ser Asp Asn Ile His Tyr Gly Val Arg Phe Ala
145                 150                 155                 160

Lys Ala Phe Val Asp Ala Lys Glu Lys Arg Leu Lys Asp Ala Arg Ala
                165                 170                 175

Leu Met Asn Leu His Asn Asn Arg Cys Gly Arg Thr Ala Val Arg Arg
            180                 185                 190

Phe Leu Lys Leu Glu Cys Lys Cys His Gly Val Ser Gly Ser Cys Thr
        195                 200                 205

Leu Arg Thr Cys Trp Arg Ala Leu Ser Asp Phe Arg Arg Thr Gly Asp
    210                 215                 220

Tyr Leu Arg Arg Arg Tyr Asp Gly Ala Val Gln Val Met Ala Thr Gln
225                 230                 235                 240

Asp Gly Ala Asn Phe Thr Ala Arg Gln Gly Tyr Arg Ala Thr
                245                 250                 255

Arg Thr Asp Leu Val Tyr Phe Asp Asn Ser Pro Asp Tyr Cys Val Leu
                260                 265                 270

Asp Lys Ala Ala Gly Ser Leu Gly Thr Ala Gly Arg Val Cys Ser Lys
            275                 280                 285

Thr Ser Lys Gly Thr Asp Gly Cys Glu Ile Met Cys Cys Gly Arg Gly
290                 295                 300

Tyr Asp Thr Thr Arg Val Thr Arg Val Thr Gln Cys Glu Cys Lys Phe
305                 310                 315                 320

His Trp Cys Cys Ala Val Arg Cys Lys Glu Cys Arg Asn Thr Val Asp
                325                 330                 335

Val His Thr Cys Lys Ala Pro Lys Lys Ala Glu Trp Leu Asp Gln Thr
            340                 345                 350
```

<210> SEQ ID NO 15
<211> LENGTH: 334
<212> TYPE: PRT
<213> ORGANISM: Homo sapiens
<300> PUBLICATION INFORMATION:
<308> DATABASE ACCESSION NUMBER: P56703
<309> DATABASE ENTRY DATE: 2016-07-06
<313> RELEVANT RESIDUES IN SEQ ID NO: (22)..(355)

<400> SEQUENCE: 15

```
Gly Tyr Pro Ile Trp Trp Ser Leu Ala Leu Gly Gln Gln Tyr Thr Ser
1               5                   10                  15
Leu Gly Ser Gln Pro Leu Leu Cys Gly Ser Ile Pro Gly Leu Val Pro
            20                  25                  30
Lys Gln Leu Arg Phe Cys Arg Asn Tyr Ile Glu Ile Met Pro Ser Val
        35                  40                  45
Ala Glu Gly Val Lys Leu Gly Ile Gln Glu Cys Gln His Gln Phe Arg
    50                  55                  60
Gly Arg Arg Trp Asn Cys Thr Thr Ile Asp Asp Ser Leu Ala Ile Phe
65                  70                  75                  80
Gly Pro Val Leu Asp Lys Ala Thr Arg Glu Ser Ala Phe Val His Ala
                85                  90                  95
Ile Ala Ser Ala Gly Val Ala Phe Ala Val Thr Arg Ser Cys Ala Glu
            100                 105                 110
Gly Thr Ser Thr Ile Cys Gly Cys Asp Ser His His Lys Gly Pro Pro
        115                 120                 125
Gly Glu Gly Trp Lys Trp Gly Gly Cys Ser Glu Asp Ala Asp Phe Gly
    130                 135                 140
Val Leu Val Ser Arg Glu Phe Ala Asp Ala Arg Glu Asn Arg Pro Asp
145                 150                 155                 160
Ala Arg Ser Ala Met Asn Lys His Asn Asn Glu Ala Gly Arg Thr Thr
                165                 170                 175
Ile Leu Asp His Met His Leu Lys Cys Lys Cys His Gly Leu Ser Gly
            180                 185                 190
Ser Cys Glu Val Lys Thr Cys Trp Trp Ala Gln Pro Asp Phe Arg Ala
        195                 200                 205
Ile Gly Asp Phe Leu Lys Asp Lys Tyr Asp Ser Ala Ser Glu Met Val
    210                 215                 220
Val Glu Lys His Arg Glu Ser Arg Gly Trp Val Glu Thr Leu Arg Ala
225                 230                 235                 240
Lys Tyr Ser Leu Phe Lys Pro Pro Thr Glu Arg Asp Leu Val Tyr Tyr
                245                 250                 255
Glu Asn Ser Pro Asn Phe Cys Glu Pro Asn Pro Glu Thr Gly Ser Phe
            260                 265                 270
Gly Thr Arg Asp Arg Thr Cys Asn Val Thr Ser His Gly Ile Asp Gly
        275                 280                 285
Cys Asp Leu Leu Cys Cys Gly Arg Gly His Asn Thr Arg Thr Glu Lys
    290                 295                 300
Arg Lys Glu Lys Cys His Cys Ile Phe His Trp Cys Cys Tyr Val Ser
305                 310                 315                 320
Cys Gln Glu Cys Ile Arg Ile Tyr Asp Val His Thr Cys Lys
                325                 330
```

<210> SEQ ID NO 16
<211> LENGTH: 329
<212> TYPE: PRT
<213> ORGANISM: Homo sapiens
<300> PUBLICATION INFORMATION:
<308> DATABASE ACCESSION NUMBER: P56705
<309> DATABASE ENTRY DATE: 2016-07-06
<313> RELEVANT RESIDUES IN SEQ ID NO: (23)..(351)

<400> SEQUENCE: 16

Ser Asn Trp Leu Tyr Leu Ala Lys Leu Ser Ser Val Gly Ser Ile Ser

```
  1               5                  10                 15
Glu Glu Glu Thr Cys Glu Lys Leu Lys Gly Leu Ile Gln Arg Gln Val
                 20                 25                 30
Gln Met Cys Lys Arg Asn Leu Glu Val Met Asp Ser Val Arg Arg Gly
                 35                 40                 45
Ala Gln Leu Ala Ile Glu Glu Cys Gln Tyr Gln Phe Arg Asn Arg Arg
         50                 55                 60
Trp Asn Cys Ser Thr Leu Asp Ser Leu Pro Val Phe Gly Lys Val Val
 65                 70                 75                 80
Thr Gln Gly Thr Arg Glu Ala Ala Phe Val Tyr Ala Ile Ser Ser Ala
                 85                 90                 95
Gly Val Ala Phe Ala Val Thr Arg Ala Cys Ser Ser Gly Glu Leu Glu
                100                105                110
Lys Cys Gly Cys Asp Arg Thr Val His Gly Val Ser Pro Gln Gly Phe
                115                120                125
Gln Trp Ser Gly Cys Ser Asp Asn Ile Ala Tyr Gly Val Ala Phe Ser
        130                135                140
Gln Ser Phe Val Asp Val Arg Glu Arg Ser Lys Gly Ala Ser Ser Ser
145                150                155                160
Arg Ala Leu Met Asn Leu His Asn Asn Glu Ala Gly Arg Lys Ala Ile
                165                170                175
Leu Thr His Met Arg Val Glu Cys Lys Cys His Gly Val Ser Gly Ser
                180                185                190
Cys Glu Val Lys Thr Cys Trp Arg Ala Val Pro Pro Phe Arg Gln Val
                195                200                205
Gly His Ala Leu Lys Glu Lys Phe Asp Gly Ala Thr Glu Val Glu Pro
                210                215                220
Arg Arg Val Gly Ser Ser Arg Ala Leu Val Pro Arg Asn Ala Gln Phe
225                230                235                240
Lys Pro His Thr Asp Glu Asp Leu Val Tyr Leu Glu Pro Ser Pro Asp
                245                250                255
Phe Cys Glu Gln Asp Met Arg Ser Gly Val Leu Gly Thr Arg Gly Arg
                260                265                270
Thr Cys Asn Lys Thr Ser Lys Ala Ile Asp Gly Cys Glu Leu Leu Cys
                275                280                285
Cys Gly Arg Gly Phe His Thr Ala Gln Val Glu Leu Ala Glu Arg Cys
                290                295                300
Ser Cys Lys Phe His Trp Cys Cys Phe Val Lys Cys Arg Gln Cys Gln
305                310                315                320
Arg Leu Val Glu Leu His Thr Cys Arg
                325

<210> SEQ ID NO 17
<211> LENGTH: 319
<212> TYPE: PRT
<213> ORGANISM: Homo sapiens
<300> PUBLICATION INFORMATION:
<308> DATABASE ACCESSION NUMBER: P41221
<309> DATABASE ENTRY DATE: 2016-07-06
<313> RELEVANT RESIDUES IN SEQ ID NO: (62)..(380)

<400> SEQUENCE: 17

Ile Ile Gly Ala Gln Pro Leu Cys Ser Gln Leu Ala Gly Leu Ser Gln
 1               5                  10                 15
Gly Gln Lys Lys Leu Cys His Leu Tyr Gln Asp His Met Gln Tyr Ile
                 20                 25                 30
```

-continued

Gly Glu Gly Ala Lys Thr Gly Ile Lys Glu Cys Gln Tyr Gln Phe Arg
            35                  40                  45

His Arg Arg Trp Asn Cys Ser Thr Val Asp Asn Thr Ser Val Phe Gly
 50                  55                  60

Arg Val Met Gln Ile Gly Ser Arg Glu Thr Ala Phe Thr Tyr Ala Val
 65                  70                  75                  80

Ser Ala Ala Gly Val Val Asn Ala Met Ser Arg Ala Cys Arg Glu Gly
                    85                  90                  95

Glu Leu Ser Thr Cys Gly Cys Ser Arg Ala Ala Arg Pro Lys Asp Leu
                100                 105                 110

Pro Arg Asp Trp Leu Trp Gly Gly Cys Gly Asp Asn Ile Asp Tyr Gly
                115                 120                 125

Tyr Arg Phe Ala Lys Glu Phe Val Asp Ala Arg Glu Arg Glu Arg Ile
            130                 135                 140

His Ala Lys Gly Ser Tyr Glu Ser Ala Arg Ile Leu Met Asn Leu His
145                 150                 155                 160

Asn Asn Glu Ala Gly Arg Arg Thr Val Tyr Asn Leu Ala Asp Val Ala
                    165                 170                 175

Cys Lys Cys His Gly Val Ser Gly Ser Cys Ser Leu Lys Thr Cys Trp
                180                 185                 190

Leu Gln Leu Ala Asp Phe Arg Lys Val Gly Asp Ala Leu Lys Glu Lys
            195                 200                 205

Tyr Asp Ser Ala Ala Ala Met Arg Leu Asn Ser Arg Gly Lys Leu Val
210                 215                 220

Gln Val Asn Ser Arg Phe Asn Ser Pro Thr Thr Gln Asp Leu Val Tyr
225                 230                 235                 240

Ile Asp Pro Ser Pro Asp Tyr Cys Val Arg Asn Glu Ser Thr Gly Ser
                    245                 250                 255

Leu Gly Thr Gln Gly Arg Leu Cys Asn Lys Thr Ser Glu Gly Met Asp
                260                 265                 270

Gly Cys Glu Leu Met Cys Cys Gly Arg Gly Tyr Asp Gln Phe Lys Thr
            275                 280                 285

Val Gln Thr Glu Arg Cys His Cys Lys Phe His Trp Cys Cys Tyr Val
290                 295                 300

Lys Cys Lys Lys Cys Thr Glu Ile Val Asp Gln Phe Val Cys Lys
305                 310                 315

<210> SEQ ID NO 18
<211> LENGTH: 342
<212> TYPE: PRT
<213> ORGANISM: Homo sapiens
<300> PUBLICATION INFORMATION:
<308> DATABASE ACCESSION NUMBER: Q9H1J7
<309> DATABASE ENTRY DATE: 2016-07-06
<313> RELEVANT RESIDUES IN SEQ ID NO: (18)..(359)

<400> SEQUENCE: 18

Gln Leu Leu Thr Asp Ala Asn Ser Trp Trp Ser Leu Ala Leu Asn Pro
1               5                   10                  15

Val Gln Arg Pro Glu Met Phe Ile Ile Gly Ala Gln Pro Val Cys Ser
            20                  25                  30

Gln Leu Pro Gly Leu Ser Pro Gly Gln Arg Lys Leu Cys Gln Leu Tyr
        35                  40                  45

Gln Glu His Met Ala Tyr Ile Gly Glu Gly Ala Lys Thr Gly Ile Lys
 50                  55                  60

```
Glu Cys Gln His Gln Phe Arg Gln Arg Arg Trp Asn Cys Ser Thr Ala
 65                  70                  75                  80

Asp Asn Ala Ser Val Phe Gly Arg Val Met Gln Ile Gly Ser Arg Glu
                 85                  90                  95

Thr Ala Phe Thr His Ala Val Ser Ala Ala Gly Val Val Asn Ala Ile
            100                 105                 110

Ser Arg Ala Cys Arg Glu Gly Glu Leu Ser Thr Cys Gly Cys Ser Arg
        115                 120                 125

Thr Ala Arg Pro Lys Asp Leu Pro Arg Asp Trp Leu Trp Gly Gly Cys
    130                 135                 140

Gly Asp Asn Val Glu Tyr Gly Tyr Arg Phe Ala Lys Glu Phe Val Asp
145                 150                 155                 160

Ala Arg Glu Arg Glu Lys Asn Phe Ala Lys Gly Ser Glu Glu Gln Gly
                165                 170                 175

Arg Val Leu Met Asn Leu Gln Asn Asn Glu Ala Gly Arg Arg Ala Val
            180                 185                 190

Tyr Lys Met Ala Asp Val Ala Cys Lys Cys His Gly Val Ser Gly Ser
        195                 200                 205

Cys Ser Leu Lys Thr Cys Trp Leu Gln Leu Ala Glu Phe Arg Lys Val
    210                 215                 220

Gly Asp Arg Leu Lys Glu Lys Tyr Asp Ser Ala Ala Ala Met Arg Val
225                 230                 235                 240

Thr Arg Lys Gly Arg Leu Glu Leu Val Asn Ser Arg Phe Thr Gln Pro
                245                 250                 255

Thr Pro Glu Asp Leu Val Tyr Val Asp Pro Ser Pro Asp Tyr Cys Leu
            260                 265                 270

Arg Asn Glu Ser Thr Gly Ser Leu Gly Thr Gln Gly Arg Leu Cys Asn
        275                 280                 285

Lys Thr Ser Glu Gly Met Asp Gly Cys Glu Leu Met Cys Cys Gly Arg
    290                 295                 300

Gly Tyr Asn Gln Phe Lys Ser Val Gln Val Glu Arg Cys His Cys Lys
305                 310                 315                 320

Phe His Trp Cys Cys Phe Val Arg Cys Lys Lys Cys Thr Glu Ile Val
                325                 330                 335

Asp Gln Tyr Ile Cys Lys
            340

<210> SEQ ID NO 19
<211> LENGTH: 341
<212> TYPE: PRT
<213> ORGANISM: Homo sapiens
<300> PUBLICATION INFORMATION:
<308> DATABASE ACCESSION NUMBER: Q9Y6F9
<309> DATABASE ENTRY DATE: 2016-07-06
<313> RELEVANT RESIDUES IN SEQ ID NO: (25)..(365)

<400> SEQUENCE: 19

Leu Trp Trp Ala Val Gly Ser Pro Leu Val Met Asp Pro Thr Ser Ile
  1               5                  10                  15

Cys Arg Lys Ala Arg Arg Leu Ala Gly Arg Gln Ala Glu Leu Cys Gln
                 20                  25                  30

Ala Glu Pro Glu Val Val Ala Glu Leu Ala Arg Gly Ala Arg Leu Gly
             35                  40                  45

Val Arg Glu Cys Gln Phe Gln Phe Arg Phe Arg Arg Trp Asn Cys Ser
         50                  55                  60

Ser His Ser Lys Ala Phe Gly Arg Ile Leu Gln Gln Asp Ile Arg Glu
```

```
                65                  70                  75                  80
        Thr Ala Phe Val Phe Ala Ile Thr Ala Ala Gly Ala Ser His Ala Val
                        85                  90                  95

Thr Gln Ala Cys Ser Met Gly Glu Leu Leu Gln Cys Gly Cys Gln Ala
                        100                 105                 110

Pro Arg Gly Arg Ala Pro Pro Arg Pro Ser Gly Leu Pro Gly Thr Pro
                        115                 120                 125

Gly Pro Pro Gly Pro Ala Gly Ser Pro Glu Gly Ser Ala Ala Trp Glu
                        130                 135                 140

Trp Gly Gly Cys Gly Asp Asp Val Asp Phe Gly Asp Glu Lys Ser Arg
        145                 150                 155                 160

Leu Phe Met Asp Ala Arg His Lys Arg Gly Arg Gly Asp Ile Arg Ala
                        165                 170                 175

Leu Val Gln Leu His Asn Asn Glu Ala Gly Arg Leu Ala Val Arg Ser
                        180                 185                 190

His Thr Arg Thr Glu Cys Lys Cys His Gly Leu Ser Gly Ser Cys Ala
                        195                 200                 205

Leu Arg Thr Cys Trp Gln Lys Leu Pro Pro Phe Arg Glu Val Gly Ala
                        210                 215                 220

Arg Leu Leu Glu Arg Phe His Gly Ala Ser Arg Val Met Gly Thr Asn
        225                 230                 235                 240

Asp Gly Lys Ala Leu Leu Pro Ala Val Arg Thr Leu Lys Pro Pro Gly
                        245                 250                 255

Arg Ala Asp Leu Leu Tyr Ala Ala Asp Ser Pro Asp Phe Cys Ala Pro
                        260                 265                 270

Asn Arg Arg Thr Gly Ser Pro Gly Thr Arg Gly Arg Ala Cys Asn Ser
                        275                 280                 285

Ser Ala Pro Asp Leu Ser Gly Cys Asp Leu Leu Cys Cys Gly Arg Gly
                        290                 295                 300

His Arg Gln Glu Ser Val Gln Leu Glu Glu Asn Cys Leu Cys Arg Phe
        305                 310                 315                 320

His Trp Cys Cys Val Val Gln Cys His Arg Cys Arg Val Arg Lys Glu
                        325                 330                 335

Leu Ser Leu Cys Leu
                        340

<210> SEQ ID NO 20
<211> LENGTH: 318
<212> TYPE: PRT
<213> ORGANISM: Homo sapiens
<300> PUBLICATION INFORMATION:
<308> DATABASE ACCESSION NUMBER: O00755
<309> DATABASE ENTRY DATE: 2016-07-06
<313> RELEVANT RESIDUES IN SEQ ID NO: (32)..(349)

<400> SEQUENCE: 20

Leu Gly Ala Ser Ile Ile Cys Asn Lys Ile Pro Gly Leu Ala Pro Arg
1               5                   10                  15

Gln Arg Ala Ile Cys Gln Ser Arg Pro Asp Ala Ile Ile Val Ile Gly
                20                  25                  30

Glu Gly Ser Gln Met Gly Leu Asp Glu Cys Gln Phe Gln Phe Arg Asn
                35                  40                  45

Gly Arg Trp Asn Cys Ser Ala Leu Gly Glu Arg Thr Val Phe Gly Lys
                50                  55                  60

Glu Leu Lys Val Gly Ser Arg Glu Ala Ala Phe Thr Tyr Ala Ile Ile
65              70                  75                  80
```

```
Ala Ala Gly Val Ala His Ala Ile Thr Ala Ala Cys Thr Gln Gly Asn
                85                  90                  95

Leu Ser Asp Cys Gly Cys Asp Lys Glu Lys Gln Gly Gln Tyr His Arg
            100                 105                 110

Asp Glu Gly Trp Lys Trp Gly Gly Cys Ser Ala Asp Ile Arg Tyr Gly
        115                 120                 125

Ile Gly Phe Ala Lys Val Phe Val Asp Ala Arg Glu Ile Lys Gln Asn
    130                 135                 140

Ala Arg Thr Leu Met Asn Leu His Asn Asn Glu Ala Gly Arg Lys Ile
145                 150                 155                 160

Leu Glu Glu Asn Met Lys Leu Glu Cys Lys Cys His Gly Val Ser Gly
                165                 170                 175

Ser Cys Thr Thr Lys Thr Cys Trp Thr Thr Leu Pro Gln Phe Arg Glu
            180                 185                 190

Leu Gly Tyr Val Leu Lys Asp Lys Tyr Asn Glu Ala Val His Val Glu
        195                 200                 205

Pro Val Arg Ala Ser Arg Asn Lys Arg Pro Thr Phe Leu Lys Ile Lys
    210                 215                 220

Lys Pro Leu Ser Tyr Arg Lys Pro Met Asp Thr Asp Leu Val Tyr Ile
225                 230                 235                 240

Glu Lys Ser Pro Asn Tyr Cys Glu Glu Asp Pro Val Thr Gly Ser Val
                245                 250                 255

Gly Thr Gln Gly Arg Ala Cys Asn Lys Thr Ala Pro Gln Ala Ser Gly
            260                 265                 270

Cys Asp Leu Met Cys Cys Gly Arg Gly Tyr Asn Thr His Gln Tyr Ala
        275                 280                 285

Arg Val Trp Gln Cys Asn Cys Lys Phe His Trp Cys Cys Tyr Val Lys
    290                 295                 300

Cys Asn Thr Cys Ser Glu Arg Thr Glu Met Tyr Thr Cys Lys
305                 310                 315

<210> SEQ ID NO 21
<211> LENGTH: 325
<212> TYPE: PRT
<213> ORGANISM: Homo sapiens
<300> PUBLICATION INFORMATION:
<308> DATABASE ACCESSION NUMBER: P56706
<309> DATABASE ENTRY DATE: 2016-07-06
<313> RELEVANT RESIDUES IN SEQ ID NO: (25)..(349)

<400> SEQUENCE: 21

Ala Leu Ser Ser Val Val Ala Leu Gly Ala Asn Ile Ile Cys Asn Lys
1               5                   10                  15

Ile Pro Gly Leu Ala Pro Arg Gln Arg Ala Ile Cys Gln Ser Arg Pro
            20                  25                  30

Asp Ala Ile Ile Val Ile Gly Glu Gly Ala Gln Met Gly Ile Asn Glu
        35                  40                  45

Cys Gln Tyr Gln Phe Arg Phe Gly Arg Trp Asn Cys Ser Ala Leu Gly
    50                  55                  60

Glu Lys Thr Val Phe Gly Gln Glu Leu Arg Val Gly Ser Arg Glu Ala
65                  70                  75                  80

Ala Phe Thr Tyr Ala Ile Thr Ala Ala Gly Val Ala His Ala Val Thr
                85                  90                  95

Ala Ala Cys Ser Gln Gly Asn Leu Ser Asn Cys Gly Cys Asp Arg Glu
            100                 105                 110
```

```
Lys Gln Gly Tyr Tyr Asn Gln Ala Glu Gly Trp Lys Trp Gly Gly Cys
            115                 120                 125

Ser Ala Asp Val Arg Tyr Gly Ile Asp Phe Ser Arg Arg Phe Val Asp
    130                 135                 140

Ala Arg Glu Ile Lys Lys Asn Ala Arg Arg Leu Met Asn Leu His Asn
145                 150                 155                 160

Asn Glu Ala Gly Arg Lys Val Leu Glu Asp Arg Met Gln Leu Glu Cys
                165                 170                 175

Lys Cys His Gly Val Ser Gly Ser Cys Thr Thr Lys Thr Cys Trp Thr
            180                 185                 190

Thr Leu Pro Lys Phe Arg Glu Val Gly His Leu Leu Lys Glu Lys Tyr
        195                 200                 205

Asn Ala Ala Val Gln Val Glu Val Val Arg Ala Ser Arg Leu Arg Gln
    210                 215                 220

Pro Thr Phe Leu Arg Ile Lys Gln Leu Arg Ser Tyr Gln Lys Pro Met
225                 230                 235                 240

Glu Thr Asp Leu Val Tyr Ile Glu Lys Ser Pro Asn Tyr Cys Glu Glu
                245                 250                 255

Asp Ala Ala Thr Gly Ser Val Gly Thr Gln Gly Arg Leu Cys Asn Arg
            260                 265                 270

Thr Ser Pro Gly Ala Asp Gly Cys Asp Thr Met Cys Cys Gly Arg Gly
        275                 280                 285

Tyr Asn Thr His Gln Tyr Thr Lys Val Trp Gln Cys Asn Cys Lys Phe
    290                 295                 300

His Trp Cys Cys Phe Val Lys Cys Asn Thr Cys Ser Glu Arg Thr Glu
305                 310                 315                 320

Val Phe Thr Cys Lys
                325

<210> SEQ ID NO 22
<211> LENGTH: 327
<212> TYPE: PRT
<213> ORGANISM: Homo sapiens
<300> PUBLICATION INFORMATION:
<308> DATABASE ACCESSION NUMBER: Q9H1J5
<309> DATABASE ENTRY DATE: 2016-07-06
<313> RELEVANT RESIDUES IN SEQ ID NO: (25)..(351)

<400> SEQUENCE: 22

Val Asn Asn Phe Leu Ile Thr Gly Pro Lys Ala Tyr Leu Thr Tyr Thr
1               5                   10                  15

Thr Ser Val Ala Leu Gly Ala Gln Ser Gly Ile Glu Glu Cys Lys Phe
            20                  25                  30

Gln Phe Ala Trp Glu Arg Trp Asn Cys Pro Glu Asn Ala Leu Gln Leu
        35                  40                  45

Ser Thr His Asn Arg Leu Arg Ser Ala Thr Arg Glu Thr Ser Phe Ile
    50                  55                  60

His Ala Ile Ser Ser Ala Gly Val Met Tyr Ile Ile Thr Lys Asn Cys
65                  70                  75                  80

Ser Met Gly Asp Phe Glu Asn Cys Gly Cys Asp Gly Ser Asn Asn Gly
                85                  90                  95

Lys Thr Gly Gly His Gly Trp Ile Trp Gly Gly Cys Ser Asp Asn Val
            100                 105                 110

Glu Phe Gly Glu Arg Ile Ser Lys Leu Phe Val Asp Ser Leu Glu Lys
        115                 120                 125

Gly Lys Asp Ala Arg Ala Leu Met Asn Leu His Asn Asn Arg Ala Gly
```

130                 135                 140

Arg Leu Ala Val Arg Ala Thr Met Lys Arg Thr Cys Lys Cys His Gly
145                 150                 155                 160

Ile Ser Gly Ser Cys Ser Ile Gln Thr Cys Trp Leu Gln Leu Ala Glu
                165                 170                 175

Phe Arg Glu Met Gly Asp Tyr Leu Lys Ala Lys Tyr Asp Gln Ala Leu
                180                 185                 190

Lys Ile Glu Met Asp Lys Arg Gln Leu Arg Ala Gly Asn Ser Ala Glu
                195                 200                 205

Gly His Trp Val Pro Ala Glu Ala Phe Leu Pro Ser Ala Glu Ala Glu
                210                 215                 220

Leu Ile Phe Leu Glu Glu Ser Pro Asp Tyr Cys Thr Cys Asn Ser Ser
225                 230                 235                 240

Leu Gly Ile Tyr Gly Thr Glu Gly Arg Glu Cys Leu Gln Asn Ser His
                245                 250                 255

Asn Thr Ser Arg Trp Glu Arg Arg Ser Cys Gly Arg Leu Cys Thr Glu
                260                 265                 270

Cys Gly Leu Gln Val Glu Glu Arg Lys Thr Glu Val Ile Ser Ser Cys
                275                 280                 285

Asn Cys Lys Phe Gln Trp Cys Cys Thr Val Lys Cys Asp Gln Cys Arg
                290                 295                 300

His Val Val Ser Lys Tyr Tyr Cys Ala Arg Ser Pro Gly Ser Ala Gln
305                 310                 315                 320

Ser Leu Gly Lys Gly Ser Ala
                325

<210> SEQ ID NO 23
<211> LENGTH: 329
<212> TYPE: PRT
<213> ORGANISM: Homo sapiens
<300> PUBLICATION INFORMATION:
<308> DATABASE ACCESSION NUMBER: Q93098
<309> DATABASE ENTRY DATE: 2016-07-06
<313> RELEVANT RESIDUES IN SEQ ID NO: (23)..(351)

<400> SEQUENCE: 23

Trp Ser Val Asn Asn Phe Leu Met Thr Gly Pro Lys Ala Tyr Leu Ile
1               5                   10                  15

Tyr Ser Ser Val Ala Ala Gly Ala Gln Ser Gly Ile Glu Glu Cys
                20                  25                  30

Lys Tyr Gln Phe Ala Trp Asp Arg Trp Asn Cys Pro Glu Arg Ala Leu
                35                  40                  45

Gln Leu Ser Ser His Gly Gly Leu Arg Ser Ala Asn Arg Glu Thr Ala
        50                  55                  60

Phe Val His Ala Ile Ser Ser Ala Gly Val Met Tyr Thr Leu Thr Arg
65                  70                  75                  80

Asn Cys Ser Leu Gly Asp Phe Asp Asn Cys Gly Cys Asp Asp Ser Arg
                85                  90                  95

Asn Gly Gln Leu Gly Gly Gln Gly Trp Leu Trp Gly Gly Cys Ser Asp
                100                 105                 110

Asn Val Gly Phe Gly Glu Ala Ile Ser Lys Gln Phe Val Asp Ala Leu
                115                 120                 125

Glu Thr Gly Gln Asp Ala Arg Ala Ala Met Asn Leu His Asn Asn Glu
                130                 135                 140

Ala Gly Arg Lys Ala Val Lys Gly Thr Met Lys Arg Thr Cys Lys Cys
145                 150                 155                 160

```
His Gly Val Ser Gly Ser Cys Thr Thr Gln Thr Cys Trp Leu Gln Leu
            165                 170                 175

Pro Glu Phe Arg Glu Val Gly Ala His Leu Lys Glu Lys Tyr His Ala
        180                 185                 190

Ala Leu Lys Val Asp Leu Leu Gln Gly Ala Gly Asn Ser Ala Ala Gly
            195                 200                 205

Arg Gly Ala Ile Ala Asp Thr Phe Arg Ser Ile Ser Thr Arg Glu Leu
        210                 215                 220

Val His Leu Glu Asp Ser Pro Asp Tyr Cys Leu Glu Asn Lys Thr Leu
225                 230                 235                 240

Gly Leu Leu Gly Thr Glu Gly Arg Glu Cys Leu Arg Arg Gly Arg Ala
            245                 250                 255

Leu Gly Arg Trp Glu Arg Arg Ser Cys Arg Arg Leu Cys Gly Asp Cys
            260                 265                 270

Gly Leu Ala Val Glu Glu Arg Ala Glu Thr Val Ser Ser Cys Asn
            275                 280                 285

Cys Lys Phe His Trp Cys Cys Ala Val Arg Cys Glu Gln Cys Arg Arg
            290                 295                 300

Arg Val Thr Lys Tyr Phe Cys Ser Arg Ala Glu Arg Pro Arg Gly Gly
305                 310                 315                 320

Ala Ala His Lys Pro Gly Arg Lys Pro
                325
```

<210> SEQ ID NO 24
<211> LENGTH: 336
<212> TYPE: PRT
<213> ORGANISM: Homo sapiens
<300> PUBLICATION INFORMATION:
<308> DATABASE ACCESSION NUMBER: O14904
<309> DATABASE ENTRY DATE: 2016-07-06
<313> RELEVANT RESIDUES IN SEQ ID NO: (30)..(365)

<400> SEQUENCE: 24

```
Tyr Phe Gly Leu Thr Gly Ser Glu Pro Leu Thr Ile Leu Pro Leu Thr
1               5                   10                  15

Leu Glu Pro Glu Ala Ala Ala Gln Ala His Tyr Lys Ala Cys Asp Arg
            20                  25                  30

Leu Lys Leu Glu Arg Lys Gln Arg Arg Met Cys Arg Arg Asp Pro Gly
        35                  40                  45

Val Ala Glu Thr Leu Val Glu Ala Val Ser Met Ser Ala Leu Glu Cys
    50                  55                  60

Gln Phe Gln Phe Arg Phe Glu Arg Trp Asn Cys Thr Leu Glu Gly Arg
65                  70                  75                  80

Tyr Arg Ala Ser Leu Leu Lys Arg Gly Phe Lys Glu Thr Ala Phe Leu
            85                  90                  95

Tyr Ala Ile Ser Ser Ala Gly Leu Thr His Ala Leu Ala Lys Ala Cys
        100                 105                 110

Ser Ala Gly Arg Met Glu Arg Cys Thr Cys Asp Glu Ala Pro Asp Leu
    115                 120                 125

Glu Asn Arg Glu Ala Trp Gln Trp Gly Cys Gly Asp Asn Leu Lys
130                 135                 140

Tyr Ser Ser Lys Phe Val Lys Glu Phe Leu Gly Arg Arg Ser Ser Lys
145                 150                 155                 160

Asp Leu Arg Ala Arg Val Asp Phe His Asn Asn Leu Val Gly Val Lys
            165                 170                 175
```

```
Val Ile Lys Ala Gly Val Glu Thr Thr Cys Lys Cys His Gly Val Ser
            180                 185                 190

Gly Ser Cys Thr Val Arg Thr Cys Trp Arg Gln Leu Ala Pro Phe His
        195                 200                 205

Glu Val Gly Lys His Leu Lys His Lys Tyr Glu Thr Ala Leu Lys Val
    210                 215                 220

Gly Ser Thr Thr Asn Glu Ala Gly Glu Ala Gly Ala Ile Ser Pro
225                 230                 235                 240

Pro Arg Gly Arg Ala Ser Gly Ala Gly Ser Asp Pro Leu Pro Arg
                245                 250                 255

Thr Pro Glu Leu Val His Leu Asp Asp Ser Pro Ser Phe Cys Leu Ala
            260                 265                 270

Gly Arg Phe Ser Pro Gly Thr Ala Gly Arg Arg Cys His Arg Glu Lys
        275                 280                 285

Asn Cys Glu Ser Ile Cys Cys Gly Arg Gly His Asn Thr Gln Ser Arg
    290                 295                 300

Val Val Thr Arg Pro Cys Gln Cys Gln Val Arg Trp Cys Cys Tyr Val
305                 310                 315                 320

Glu Cys Arg Gln Cys Thr Gln Arg Glu Val Tyr Thr Cys Lys Gly
                325                 330                 335

<210> SEQ ID NO 25
<211> LENGTH: 174
<212> TYPE: PRT
<213> ORGANISM: Homo sapiens
<300> PUBLICATION INFORMATION:
<308> DATABASE ACCESSION NUMBER: Q15465
<309> DATABASE ENTRY DATE: 2016-07-06
<313> RELEVANT RESIDUES IN SEQ ID NO: (24)..(197)

<400> SEQUENCE: 25

Cys Gly Pro Gly Arg Gly Phe Gly Lys Arg Arg His Pro Lys Lys Leu
1               5                   10                  15

Thr Pro Leu Ala Tyr Lys Gln Phe Ile Pro Asn Val Ala Glu Lys Thr
            20                  25                  30

Leu Gly Ala Ser Gly Arg Tyr Glu Gly Lys Ile Ser Arg Asn Ser Glu
        35                  40                  45

Arg Phe Lys Glu Leu Thr Pro Asn Tyr Asn Pro Asp Ile Ile Phe Lys
50                  55                  60

Asp Glu Glu Asn Thr Gly Ala Asp Arg Leu Met Thr Gln Arg Cys Lys
65                  70                  75                  80

Asp Lys Leu Asn Ala Leu Ala Ile Ser Val Met Asn Gln Trp Pro Gly
                85                  90                  95

Val Lys Leu Arg Val Thr Glu Gly Trp Asp Glu Asp Gly His His Ser
            100                 105                 110

Glu Glu Ser Leu His Tyr Glu Gly Arg Ala Val Asp Ile Thr Thr Ser
        115                 120                 125

Asp Arg Asp Arg Ser Lys Tyr Gly Met Leu Ala Arg Leu Ala Val Glu
130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly
                165                 170

<210> SEQ ID NO 26
<211> LENGTH: 176
<212> TYPE: PRT
```

<213> ORGANISM: Homo sapiens
<300> PUBLICATION INFORMATION:
<308> DATABASE ACCESSION NUMBER: O43323
<309> DATABASE ENTRY DATE: 2016-07-06
<313> RELEVANT RESIDUES IN SEQ ID NO: (23)..(198)

<400> SEQUENCE: 26

```
Cys Gly Pro Gly Arg Gly Pro Val Gly Arg Arg Tyr Ala Arg Lys
1               5                   10                  15

Gln Leu Val Pro Leu Leu Tyr Lys Gln Phe Val Pro Gly Val Pro Glu
            20                  25                  30

Arg Thr Leu Gly Ala Ser Gly Pro Ala Glu Gly Arg Val Ala Arg Gly
        35                  40                  45

Ser Glu Arg Phe Arg Asp Leu Val Pro Asn Tyr Asn Pro Asp Ile Ile
    50                  55                  60

Phe Lys Asp Glu Glu Asn Ser Gly Ala Asp Arg Leu Met Thr Glu Arg
65                  70                  75                  80

Cys Lys Glu Arg Val Asn Ala Leu Ala Ile Ala Val Met Asn Met Trp
                85                  90                  95

Pro Gly Val Arg Leu Arg Val Thr Glu Gly Trp Asp Glu Asp Gly His
            100                 105                 110

His Ala Gln Asp Ser Leu His Tyr Glu Gly Arg Ala Leu Asp Ile Thr
        115                 120                 125

Thr Ser Asp Arg Asp Arg Asn Lys Tyr Gly Leu Leu Ala Arg Leu Ala
    130                 135                 140

Val Glu Ala Gly Phe Asp Trp Val Tyr Tyr Glu Ser Arg Asn His Val
145                 150                 155                 160

His Val Ser Val Lys Ala Asp Asn Ser Leu Ala Val Arg Ala Gly Gly
                165                 170                 175
```

<210> SEQ ID NO 27
<211> LENGTH: 175
<212> TYPE: PRT
<213> ORGANISM: Homo sapiens
<300> PUBLICATION INFORMATION:
<308> DATABASE ACCESSION NUMBER: Q14623
<309> DATABASE ENTRY DATE: 2016-07-06
<313> RELEVANT RESIDUES IN SEQ ID NO: (28)..(202)

<400> SEQUENCE: 27

```
Cys Gly Pro Gly Arg Val Val Gly Ser Arg Arg Arg Pro Arg Lys
1               5                   10                  15

Leu Val Pro Leu Ala Tyr Lys Gln Phe Ser Pro Asn Val Pro Glu Lys
            20                  25                  30

Thr Leu Gly Ala Ser Gly Arg Tyr Glu Gly Lys Ile Ala Arg Ser Ser
        35                  40                  45

Glu Arg Phe Lys Glu Leu Thr Pro Asn Tyr Asn Pro Asp Ile Ile Phe
    50                  55                  60

Lys Asp Glu Glu Asn Thr Gly Ala Asp Arg Leu Met Thr Gln Arg Cys
65                  70                  75                  80

Lys Asp Arg Leu Asn Ser Leu Ala Ile Ser Val Met Asn Gln Trp Pro
                85                  90                  95

Gly Val Lys Leu Arg Val Thr Glu Gly Trp Asp Glu Asp Gly His His
            100                 105                 110

Ser Glu Glu Ser Leu His Tyr Glu Gly Arg Ala Val Asp Ile Thr Thr
        115                 120                 125

Ser Asp Arg Asp Arg Asn Lys Tyr Gly Leu Leu Ala Arg Leu Ala Val
    130                 135                 140
```

Glu Ala Gly Phe Asp Trp Val Tyr Tyr Glu Ser Lys Ala His Val His
145                 150                 155                 160

Cys Ser Val Lys Ser Glu His Ser Ala Ala Ala Lys Thr Gly Gly
                165                 170                 175

<210> SEQ ID NO 28
<211> LENGTH: 117
<212> TYPE: PRT
<213> ORGANISM: Homo sapiens
<300> PUBLICATION INFORMATION:
<308> DATABASE ACCESSION NUMBER: P23560
<309> DATABASE ENTRY DATE: 2016-07-06
<313> RELEVANT RESIDUES IN SEQ ID NO: (131)..(247)

<400> SEQUENCE: 28

Asp Pro Ala Arg Arg Gly Glu Leu Ser Val Cys Asp Ser Ile Ser Glu
1               5                   10                  15

Trp Val Thr Ala Ala Asp Lys Lys Thr Ala Val Asp Met Ser Gly Gly
                20                  25                  30

Thr Val Thr Val Leu Glu Lys Val Pro Val Ser Lys Gly Gln Leu Lys
                35                  40                  45

Gln Tyr Phe Tyr Glu Thr Lys Cys Asn Pro Met Gly Tyr Thr Lys Glu
    50                  55                  60

Gly Cys Arg Gly Ile Asp Lys Arg His Trp Asn Ser Gln Cys Arg Thr
65                  70                  75                  80

Thr Gln Ser Tyr Val Arg Ala Leu Thr Met Asp Ser Lys Lys Arg Ile
                85                  90                  95

Gly Trp Arg Phe Ile Arg Ile Asp Thr Ser Cys Val Cys Thr Leu Thr
                100                 105                 110

Ile Lys Arg Gly Arg
        115

<210> SEQ ID NO 29
<211> LENGTH: 118
<212> TYPE: PRT
<213> ORGANISM: Homo sapiens
<300> PUBLICATION INFORMATION:
<308> DATABASE ACCESSION NUMBER: P01138
<309> DATABASE ENTRY DATE: 2016-07-06
<313> RELEVANT RESIDUES IN SEQ ID NO: (124)..(241)

<400> SEQUENCE: 29

Ser His Pro Ile Phe His Arg Gly Glu Phe Ser Val Cys Asp Ser Val
1               5                   10                  15

Ser Val Trp Val Gly Asp Lys Thr Thr Ala Thr Asp Ile Lys Gly Lys
                20                  25                  30

Glu Val Met Val Leu Gly Glu Val Asn Ile Asn Asn Ser Val Phe Lys
                35                  40                  45

Gln Tyr Phe Phe Glu Thr Lys Cys Arg Asp Pro Asn Pro Val Asp Ser
    50                  55                  60

Gly Cys Arg Gly Ile Asp Ser Lys His Trp Asn Ser Tyr Cys Thr Thr
65                  70                  75                  80

Thr His Thr Phe Val Lys Ala Leu Thr Met Asp Gly Lys Gln Ala Ala
                85                  90                  95

Trp Arg Phe Ile Arg Ile Asp Thr Ala Cys Val Cys Val Leu Ser Arg
                100                 105                 110

Lys Ala Val Arg Arg Ala
        115

<210> SEQ ID NO 30
<211> LENGTH: 117
<212> TYPE: PRT
<213> ORGANISM: Homo sapiens
<300> PUBLICATION INFORMATION:
<308> DATABASE ACCESSION NUMBER: P20783
<309> DATABASE ENTRY DATE: 2016-07-06
<313> RELEVANT RESIDUES IN SEQ ID NO: (141)..(257)

<400> SEQUENCE: 30

Glu His Lys Ser His Arg Gly Glu Tyr Ser Val Cys Asp Ser Glu Ser
1               5                   10                  15

Leu Trp Val Thr Asp Lys Ser Ser Ala Ile Asp Ile Arg Gly His Gln
            20                  25                  30

Val Thr Val Leu Gly Glu Ile Lys Thr Gly Asn Ser Pro Val Lys Gln
        35                  40                  45

Tyr Phe Tyr Glu Thr Arg Cys Lys Glu Ala Arg Pro Val Lys Asn Gly
    50                  55                  60

Cys Arg Gly Ile Asp Asp Lys His Trp Asn Ser Gln Cys Lys Thr Ser
65                  70                  75                  80

Gln Thr Tyr Val Arg Ala Leu Thr Ser Glu Asn Asn Lys Leu Val Gly
                85                  90                  95

Trp Arg Trp Ile Arg Ile Asp Thr Ser Cys Val Cys Ala Leu Ser Arg
            100                 105                 110

Lys Ile Gly Arg Thr
        115

<210> SEQ ID NO 31
<211> LENGTH: 128
<212> TYPE: PRT
<213> ORGANISM: Homo sapiens
<300> PUBLICATION INFORMATION:
<308> DATABASE ACCESSION NUMBER: P34130
<309> DATABASE ENTRY DATE: 2016-07-06
<313> RELEVANT RESIDUES IN SEQ ID NO: (83)..(210)

<400> SEQUENCE: 31

Ser Glu Thr Ala Pro Ala Ser Arg Arg Gly Glu Leu Ala Val Cys Asp
1               5                   10                  15

Ala Val Ser Gly Trp Val Thr Asp Arg Arg Thr Ala Val Asp Leu Arg
            20                  25                  30

Gly Arg Glu Val Glu Val Leu Gly Glu Val Pro Ala Ala Gly Gly Ser
        35                  40                  45

Pro Leu Arg Gln Tyr Phe Phe Glu Thr Arg Cys Lys Ala Asp Asn Ala
    50                  55                  60

Glu Glu Gly Gly Pro Gly Ala Gly Gly Gly Gly Cys Arg Gly Val Asp
65                  70                  75                  80

Arg Arg His Trp Val Ser Glu Cys Lys Ala Lys Gln Ser Tyr Val Arg
                85                  90                  95

Ala Leu Thr Ala Asp Ala Gln Gly Arg Val Gly Trp Arg Trp Ile Arg
            100                 105                 110

Ile Asp Thr Ala Cys Val Cys Thr Leu Leu Ser Arg Thr Gly Arg Ala
        115                 120                 125

<210> SEQ ID NO 32
<211> LENGTH: 198
<212> TYPE: PRT
<213> ORGANISM: Homo sapiens
<300> PUBLICATION INFORMATION:
<308> DATABASE ACCESSION NUMBER: P26441

<309> DATABASE ENTRY DATE: 2016-07-06
<313> RELEVANT RESIDUES IN SEQ ID NO: (1)..(198)

<400> SEQUENCE: 32

```
Met Ala Phe Thr Glu His Ser Pro Leu Thr Pro His Arg Arg Asp Leu
1               5                   10                  15

Cys Ser Arg Ser Ile Trp Leu Ala Arg Lys Ile Arg Ser Asp Leu Thr
            20                  25                  30

Ala Leu Thr Glu Ser Tyr Val Lys His Gln Gly Leu Asn Lys Asn Ile
        35                  40                  45

Asn Leu Asp Ser Ala Asp Gly Met Pro Val Ala Ser Thr Asp Gln Trp
50                  55                  60

Ser Glu Leu Thr Glu Ala Glu Arg Leu Gln Glu Asn Leu Gln Ala Tyr
65                  70                  75                  80

Arg Thr Phe His Val Leu Leu Ala Arg Leu Leu Glu Asp Gln Gln Val
                85                  90                  95

His Phe Thr Pro Thr Glu Gly Asp Phe His Gln Ala Ile His Thr Leu
            100                 105                 110

Leu Leu Gln Val Ala Ala Phe Ala Tyr Gln Ile Glu Glu Leu Met Ile
        115                 120                 125

Leu Leu Glu Tyr Lys Ile Pro Arg Asn Glu Ala Asp Gly Met Pro Ile
130                 135                 140

Asn Val Gly Asp Gly Leu Phe Glu Lys Lys Leu Trp Gly Leu Lys
145                 150                 155                 160

Val Leu Gln Glu Leu Ser Gln Trp Thr Val Arg Ser Ile His Asp Leu
                165                 170                 175

Arg Phe Ile Ser Ser His Gln Thr Gly Ile Pro Ala Arg Gly Ser His
            180                 185                 190

Tyr Ile Ala Asn Asn Lys
        195
```

<210> SEQ ID NO 33
<211> LENGTH: 132
<212> TYPE: PRT
<213> ORGANISM: Homo sapiens
<300> PUBLICATION INFORMATION:
<308> DATABASE ACCESSION NUMBER: P39905
<309> DATABASE ENTRY DATE: 2016-07-06
<313> RELEVANT RESIDUES IN SEQ ID NO: (80)..(211)

<400> SEQUENCE: 33

```
Asp Lys Gln Met Ala Val Leu Pro Arg Arg Glu Arg Asn Arg Gln Ala
1               5                   10                  15

Ala Ala Ala Asn Pro Glu Asn Ser Arg Gly Lys Gly Arg Arg Gly Gln
            20                  25                  30

Arg Gly Lys Asn Arg Gly Cys Val Leu Thr Ala Ile His Leu Asn Val
        35                  40                  45

Thr Asp Leu Gly Leu Gly Tyr Glu Thr Lys Glu Glu Leu Ile Phe Arg
    50                  55                  60

Tyr Cys Ser Gly Ser Cys Asp Ala Ala Glu Thr Thr Tyr Asp Lys Ile
65                  70                  75                  80

Leu Lys Asn Leu Ser Arg Asn Arg Arg Leu Val Ser Asp Lys Val Gly
                85                  90                  95

Gln Ala Cys Cys Arg Pro Ile Ala Phe Asp Asp Asp Leu Ser Phe Leu
            100                 105                 110

Asp Asp Asn Leu Val Tyr His Ile Leu Arg Lys His Ser Ala Lys Arg
        115                 120                 125
```

Cys Gly Cys Ile
        130

<210> SEQ ID NO 34
<211> LENGTH: 111
<212> TYPE: PRT
<213> ORGANISM: Homo sapiens
<300> PUBLICATION INFORMATION:
<308> DATABASE ACCESSION NUMBER: Q5T4W7
<309> DATABASE ENTRY DATE: 2016-07-06
<313> RELEVANT RESIDUES IN SEQ ID NO: (110)..(220)

<400> SEQUENCE: 34

Gly Pro Gly Ser Arg Ala Arg Ala Gly Ala Arg Gly Cys Arg Leu
1               5                   10                  15

Arg Ser Gln Leu Val Pro Val Arg Ala Leu Gly Leu Gly His Arg Ser
            20                  25                  30

Asp Glu Leu Val Arg Phe Arg Phe Cys Ser Gly Ser Cys Arg Arg Ala
        35                  40                  45

Arg Ser Pro His Asp Leu Ser Leu Ala Ser Leu Leu Gly Ala Gly Ala
    50                  55                  60

Leu Arg Pro Pro Gly Ser Arg Pro Val Ser Gln Pro Cys Cys Arg
65                  70                  75                  80

Pro Thr Arg Tyr Glu Ala Val Ser Phe Met Asp Val Asn Ser Thr Trp
                85                  90                  95

Arg Thr Val Asp Arg Leu Ser Ala Thr Ala Cys Gly Cys Leu Gly
            100                 105                 110

<210> SEQ ID NO 35
<211> LENGTH: 100
<212> TYPE: PRT
<213> ORGANISM: Homo sapiens
<300> PUBLICATION INFORMATION:
<308> DATABASE ACCESSION NUMBER: Q99748
<309> DATABASE ENTRY DATE: 2016-07-06
<313> RELEVANT RESIDUES IN SEQ ID NO: (98)..(197)

<400> SEQUENCE: 35

Leu Gly Ala Arg Pro Cys Gly Leu Arg Glu Leu Glu Val Arg Val Ser
1               5                   10                  15

Glu Leu Gly Leu Gly Tyr Ala Ser Asp Glu Thr Val Leu Phe Arg Tyr
            20                  25                  30

Cys Ala Gly Ala Cys Glu Ala Ala Arg Val Tyr Asp Leu Gly Leu
        35                  40                  45

Arg Arg Leu Arg Gln Arg Arg Arg Leu Arg Arg Glu Arg Val Arg Ala
    50                  55                  60

Gln Pro Cys Cys Arg Pro Thr Ala Tyr Glu Asp Glu Val Ser Phe Leu
65                  70                  75                  80

Asp Ala His Ser Arg Tyr His Thr Val His Glu Leu Ser Ala Arg Glu
                85                  90                  95

Cys Ala Cys Val
            100

<210> SEQ ID NO 36
<211> LENGTH: 133
<212> TYPE: PRT
<213> ORGANISM: Homo sapiens
<300> PUBLICATION INFORMATION:
<308> DATABASE ACCESSION NUMBER: O60542
<309> DATABASE ENTRY DATE: 2016-07-06
<313> RELEVANT RESIDUES IN SEQ ID NO: (24)..(156)

<400> SEQUENCE: 36

Pro Asp Ala Arg Gly Val Pro Val Ala Asp Gly Glu Phe Ser Ser Glu
1               5                   10                  15

Gln Val Ala Lys Ala Gly Gly Thr Trp Leu Gly Thr His Arg Pro Leu
            20                  25                  30

Ala Arg Leu Arg Arg Ala Leu Ser Gly Pro Cys Gln Leu Trp Ser Leu
        35                  40                  45

Thr Leu Ser Val Ala Glu Leu Gly Leu Gly Tyr Ala Ser Glu Glu Lys
    50                  55                  60

Val Ile Phe Arg Tyr Cys Ala Gly Ser Cys Pro Arg Gly Ala Arg Thr
65              70                  75                  80

Gln His Gly Leu Ala Leu Ala Arg Leu Gln Gly Gln Gly Arg Ala His
                85                  90                  95

Gly Gly Pro Cys Cys Arg Pro Thr Arg Tyr Thr Asp Val Ala Phe Leu
            100                 105                 110

Asp Asp Arg His Arg Trp Gln Arg Leu Pro Gln Leu Ser Ala Ala Ala
        115                 120                 125

Cys Gly Cys Gly Gly
        130

<210> SEQ ID NO 37
<211> LENGTH: 178
<212> TYPE: PRT
<213> ORGANISM: Homo sapiens
<300> PUBLICATION INFORMATION:
<308> DATABASE ACCESSION NUMBER: P15018
<309> DATABASE ENTRY DATE: 2016-07-06
<313> RELEVANT RESIDUES IN SEQ ID NO: (25)..(202)

<400> SEQUENCE: 37

Leu Pro Ile Thr Pro Val Asn Ala Thr Cys Ala Ile Arg His Pro Cys
1               5                   10                  15

His Asn Asn Leu Met Asn Gln Ile Arg Ser Gln Leu Ala Gln Leu Asn
            20                  25                  30

Gly Ser Ala Asn Ala Leu Phe Ile Leu Tyr Tyr Thr Ala Gln Gly Glu
        35                  40                  45

Pro Phe Pro Asn Asn Leu Asp Lys Leu Cys Gly Pro Asn Val Thr Asp
    50                  55                  60

Phe Pro Pro Phe His Ala Asn Gly Thr Glu Lys Ala Lys Leu Val Glu
65              70                  75                  80

Leu Tyr Arg Ile Val Val Tyr Leu Gly Thr Ser Leu Gly Asn Ile Thr
                85                  90                  95

Arg Asp Gln Lys Ile Leu Asn Pro Ser Ala Leu Ser Leu His Ser Lys
            100                 105                 110

Leu Asn Ala Thr Ala Asp Ile Leu Arg Gly Leu Leu Ser Asn Val Leu
        115                 120                 125

Cys Arg Leu Cys Ser Lys Tyr His Val Gly His Val Asp Val Thr Tyr
    130                 135                 140

Gly Pro Asp Thr Ser Gly Lys Asp Val Phe Gln Lys Lys Lys Leu Gly
145                 150                 155                 160

Cys Gln Leu Leu Gly Lys Tyr Lys Gln Ile Ile Ala Val Leu Ala Gln
                165                 170                 175

Ala Phe

<210> SEQ ID NO 38

```
<211> LENGTH: 6
<212> TYPE: PRT
<213> ORGANISM: Homo sapiens
<300> PUBLICATION INFORMATION:
<308> DATABASE ACCESSION NUMBER: P01019
<309> DATABASE ENTRY DATE: 2016-07-06
<313> RELEVANT RESIDUES IN SEQ ID NO: (36)..(41)

<400> SEQUENCE: 38

Val Tyr Ile His Pro Phe
1               5

<210> SEQ ID NO 39
<211> LENGTH: 341
<212> TYPE: PRT
<213> ORGANISM: Homo sapiens
<300> PUBLICATION INFORMATION:
<308> DATABASE ACCESSION NUMBER: P04628
<309> DATABASE ENTRY DATE: 2016-07-06
<313> RELEVANT RESIDUES IN SEQ ID NO: (28)..(368)

<400> SEQUENCE: 39

Ala Asn Ser Ser Gly Arg Trp Trp Gly Ile Val Asn Val Ala Ser Ser
1               5                   10                  15

Thr Asn Leu Leu Thr Asp Ser Lys Ser Leu Gln Leu Val Leu Glu Pro
            20                  25                  30

Ser Leu Gln Leu Leu Ser Arg Lys Gln Arg Arg Leu Ile Arg Gln Asn
        35                  40                  45

Pro Gly Ile Leu His Ser Val Ser Gly Gly Leu Gln Ser Ala Val Arg
    50                  55                  60

Glu Cys Lys Trp Gln Phe Arg Asn Arg Arg Trp Asn Cys Pro Thr Ala
65                  70                  75                  80

Pro Gly Pro His Leu Phe Gly Lys Ile Val Asn Arg Gly Cys Arg Glu
                85                  90                  95

Thr Ala Phe Ile Phe Ala Ile Thr Ser Ala Gly Val Thr His Ser Val
            100                 105                 110

Ala Arg Ser Cys Ser Glu Gly Ser Ile Glu Ser Cys Thr Cys Asp Tyr
        115                 120                 125

Arg Arg Arg Gly Pro Gly Gly Pro Asp Trp His Trp Gly Gly Cys Ser
    130                 135                 140

Asp Asn Ile Asp Phe Gly Arg Leu Phe Gly Arg Glu Phe Val Asp Ser
145                 150                 155                 160

Gly Glu Lys Gly Arg Asp Leu Arg Phe Leu Met Asn Leu His Asn Asn
                165                 170                 175

Glu Ala Gly Arg Thr Thr Val Phe Ser Glu Met Arg Gln Glu Cys Lys
            180                 185                 190

Cys His Gly Met Ser Gly Ser Cys Thr Val Arg Thr Cys Trp Met Arg
        195                 200                 205

Leu Pro Thr Leu Arg Ala Val Gly Asp Val Leu Arg Asp Arg Phe Asp
    210                 215                 220

Gly Ala Ser Arg Val Leu Tyr Gly Asn Arg Gly Ser Asn Arg Ala Ser
225                 230                 235                 240

Arg Ala Glu Leu Leu Arg Leu Glu Pro Glu Asp Pro Ala His Lys Pro
                245                 250                 255

Pro Ser Pro His Asp Leu Val Tyr Phe Glu Lys Ser Pro Asn Phe Cys
            260                 265                 270

Thr Tyr Ser Gly Arg Leu Gly Thr Ala Gly Thr Ala Gly Arg Ala Cys
        275                 280                 285
```

```
Asn Ser Ser Pro Ala Leu Asp Gly Cys Glu Leu Leu Cys Cys Gly
    290                 295                 300

Arg Gly His Arg Thr Arg Thr Gln Arg Val Thr Glu Arg Cys Asn Cys
305                 310                 315                 320

Thr Phe His Trp Cys Cys His Val Ser Cys Arg Asn Cys Thr His Thr
                325                 330                 335

Arg Val Leu His Glu
            340

<210> SEQ ID NO 40
<211> LENGTH: 333
<212> TYPE: PRT
<213> ORGANISM: Homo sapiens
<300> PUBLICATION INFORMATION:
<308> DATABASE ACCESSION NUMBER: P09544
<309> DATABASE ENTRY DATE: 2016-07-06
<313> RELEVANT RESIDUES IN SEQ ID NO: (26)..(358)

<400> SEQUENCE: 40

Ser Trp Trp Tyr Met Arg Ala Thr Gly Gly Ser Ser Arg Val Met Cys
1               5                   10                  15

Asp Asn Val Pro Gly Leu Val Ser Ser Gln Arg Gln Leu Cys His Arg
            20                  25                  30

His Pro Asp Val Met Arg Ala Ile Ser Gln Gly Val Ala Glu Trp Thr
        35                  40                  45

Ala Glu Cys Gln His Gln Phe Arg Gln His Arg Trp Asn Cys Asn Thr
    50                  55                  60

Leu Asp Arg Asp His Ser Leu Phe Gly Arg Val Leu Leu Arg Ser Ser
65                  70                  75                  80

Arg Glu Ser Ala Phe Val Tyr Ala Ile Ser Ser Ala Gly Val Val Phe
                85                  90                  95

Ala Ile Thr Arg Ala Cys Ser Gln Gly Glu Val Lys Ser Cys Ser Cys
            100                 105                 110

Asp Pro Lys Lys Met Gly Ser Ala Lys Asp Ser Lys Gly Ile Phe Asp
        115                 120                 125

Trp Gly Gly Cys Ser Asp Asn Ile Asp Tyr Gly Ile Lys Phe Ala Arg
    130                 135                 140

Ala Phe Val Asp Ala Lys Glu Arg Lys Gly Lys Asp Ala Arg Ala Leu
145                 150                 155                 160

Met Asn Leu His Asn Asn Arg Ala Gly Arg Lys Ala Val Lys Arg Phe
                165                 170                 175

Leu Lys Gln Glu Cys Lys Cys His Gly Val Ser Gly Ser Cys Thr Leu
            180                 185                 190

Arg Thr Cys Trp Leu Ala Met Ala Asp Phe Arg Lys Thr Gly Asp Tyr
        195                 200                 205

Leu Trp Arg Lys Tyr Asn Gly Ala Ile Gln Val Val Met Asn Gln Asp
    210                 215                 220

Gly Thr Gly Phe Thr Val Ala Asn Glu Arg Phe Lys Lys Pro Thr Lys
225                 230                 235                 240

Asn Asp Leu Val Tyr Phe Glu Asn Ser Pro Asp Tyr Cys Ile Arg Asp
                245                 250                 255

Arg Glu Ala Gly Ser Leu Gly Thr Ala Gly Arg Val Cys Asn Leu Thr
            260                 265                 270

Ser Arg Gly Met Asp Ser Cys Glu Val Met Cys Cys Gly Arg Gly Tyr
        275                 280                 285

Asp Thr Ser His Val Thr Arg Met Thr Lys Cys Gly Cys Lys Phe His
```

```
                 290                 295                 300
Trp Cys Cys Ala Val Arg Cys Gln Asp Cys Leu Glu Ala Leu Asp Val
305                 310                 315                 320

His Thr Cys Lys Ala Pro Lys Asn Ala Asp Trp Thr Thr
                325                 330

<210> SEQ ID NO 41
<211> LENGTH: 350
<212> TYPE: PRT
<213> ORGANISM: Homo sapiens
<300> PUBLICATION INFORMATION:
<308> DATABASE ACCESSION NUMBER: Q93097
<309> DATABASE ENTRY DATE: 2016-07-06
<313> RELEVANT RESIDUES IN SEQ ID NO: (42)..(391)

<400> SEQUENCE: 41

Ala Cys Leu Leu Leu Leu Leu Leu Thr Leu Pro Ala Arg Val Asp
1               5                   10                  15

Thr Ser Trp Trp Tyr Ile Gly Ala Leu Gly Ala Arg Val Ile Cys Asp
                20                  25                  30

Asn Ile Pro Gly Leu Val Ser Arg Gln Arg Gln Leu Cys Gln Arg Tyr
            35                  40                  45

Pro Asp Ile Met Arg Ser Val Gly Glu Gly Ala Arg Glu Trp Ile Arg
50                  55                  60

Glu Cys Gln His Gln Phe Arg His His Arg Trp Asn Cys Thr Thr Leu
65                  70                  75                  80

Asp Arg Asp His Thr Val Phe Gly Arg Val Met Leu Arg Ser Ser Arg
                85                  90                  95

Glu Ala Ala Phe Val Tyr Ala Ile Ser Ser Ala Gly Val Val His Ala
            100                 105                 110

Ile Thr Arg Ala Cys Ser Gln Gly Glu Leu Ser Val Cys Ser Cys Asp
        115                 120                 125

Pro Tyr Thr Arg Gly Arg His His Asp Gln Arg Gly Asp Phe Asp Trp
130                 135                 140

Gly Gly Cys Ser Asp Asn Ile His Tyr Gly Val Arg Phe Ala Lys Ala
145                 150                 155                 160

Phe Val Asp Ala Lys Glu Lys Arg Leu Lys Asp Ala Arg Ala Leu Met
                165                 170                 175

Asn Leu His Asn Asn Arg Cys Gly Arg Thr Ala Val Arg Arg Phe Leu
            180                 185                 190

Lys Leu Glu Cys Lys Cys His Gly Val Ser Gly Ser Cys Thr Leu Arg
        195                 200                 205

Thr Cys Trp Arg Ala Leu Ser Asp Phe Arg Arg Thr Gly Asp Tyr Leu
210                 215                 220

Arg Arg Arg Tyr Asp Gly Ala Val Gln Val Met Ala Thr Gln Asp Gly
225                 230                 235                 240

Ala Asn Phe Thr Ala Ala Arg Gln Gly Tyr Arg Arg Ala Thr Arg Thr
                245                 250                 255

Asp Leu Val Tyr Phe Asp Asn Ser Pro Asp Tyr Cys Val Leu Asp Lys
            260                 265                 270

Ala Ala Gly Ser Leu Gly Thr Ala Gly Arg Val Cys Ser Lys Thr Ser
        275                 280                 285

Lys Gly Thr Asp Gly Cys Glu Ile Met Cys Cys Gly Arg Gly Tyr Asp
290                 295                 300

Thr Thr Arg Val Thr Arg Val Thr Gln Cys Glu Cys Lys Phe His Trp
305                 310                 315                 320
```

```
Cys Cys Ala Val Arg Cys Lys Glu Cys Arg Asn Thr Val Asp Val His
                325                 330                 335
Thr Cys Lys Ala Pro Lys Lys Ala Glu Trp Leu Asp Gln Thr
            340                 345                 350

<210> SEQ ID NO 42
<211> LENGTH: 332
<212> TYPE: PRT
<213> ORGANISM: Homo sapiens
<300> PUBLICATION INFORMATION:
<308> DATABASE ACCESSION NUMBER: P56703
<309> DATABASE ENTRY DATE: 2016-07-06
<313> RELEVANT RESIDUES IN SEQ ID NO: (22)..(353)

<400> SEQUENCE: 42

Gly Tyr Pro Ile Trp Trp Ser Leu Ala Leu Gly Gln Gln Tyr Thr Ser
1               5                   10                  15
Leu Gly Ser Gln Pro Leu Leu Cys Gly Ser Ile Pro Gly Leu Val Pro
                20                  25                  30
Lys Gln Leu Arg Phe Cys Arg Asn Tyr Ile Glu Ile Met Pro Ser Val
            35                  40                  45
Ala Glu Gly Val Lys Leu Gly Ile Gln Glu Cys Gln His Gln Phe Arg
        50                  55                  60
Gly Arg Arg Trp Asn Cys Thr Thr Ile Asp Asp Ser Leu Ala Ile Phe
65                  70                  75                  80
Gly Pro Val Leu Asp Lys Ala Thr Arg Glu Ser Ala Phe Val His Ala
                85                  90                  95
Ile Ala Ser Ala Gly Val Ala Phe Ala Val Thr Arg Ser Cys Ala Glu
            100                 105                 110
Gly Thr Ser Thr Ile Cys Gly Cys Asp Ser His His Lys Gly Pro Pro
        115                 120                 125
Gly Glu Gly Trp Lys Trp Gly Gly Cys Ser Glu Asp Ala Asp Phe Gly
130                 135                 140
Val Leu Val Ser Arg Glu Phe Ala Asp Ala Arg Glu Asn Arg Pro Asp
145                 150                 155                 160
Ala Arg Ser Ala Met Asn Lys His Asn Asn Glu Ala Gly Arg Thr Thr
                165                 170                 175
Ile Leu Asp His Met His Leu Lys Cys Lys Cys His Gly Leu Ser Gly
            180                 185                 190
Ser Cys Glu Val Lys Thr Cys Trp Trp Ala Gln Pro Asp Phe Arg Ala
        195                 200                 205
Ile Gly Asp Phe Leu Lys Asp Lys Tyr Asp Ser Ala Ser Glu Met Val
210                 215                 220
Val Glu Lys His Arg Glu Ser Arg Gly Trp Val Glu Thr Leu Arg Ala
225                 230                 235                 240
Lys Tyr Ser Leu Phe Lys Pro Pro Thr Glu Arg Asp Leu Val Tyr Tyr
                245                 250                 255
Glu Asn Ser Pro Asn Phe Cys Glu Pro Asn Pro Glu Thr Gly Ser Phe
            260                 265                 270
Gly Thr Arg Asp Arg Thr Cys Asn Val Thr Ser His Gly Ile Asp Gly
        275                 280                 285
Cys Asp Leu Leu Cys Cys Gly Arg Gly His Asn Thr Arg Thr Glu Lys
290                 295                 300
Arg Lys Glu Lys Cys His Cys Ile Phe His Trp Cys Cys Tyr Val Ser
305                 310                 315                 320
```

```
Cys Gln Glu Cys Ile Arg Ile Tyr Asp Val His Thr
                    325                 330
```

<210> SEQ ID NO 43
<211> LENGTH: 327
<212> TYPE: PRT
<213> ORGANISM: Homo sapiens
<300> PUBLICATION INFORMATION:
<308> DATABASE ACCESSION NUMBER: P56705
<309> DATABASE ENTRY DATE: 2016-07-06
<313> RELEVANT RESIDUES IN SEQ ID NO: (25)..(351)

<400> SEQUENCE: 43

```
Trp Leu Tyr Leu Ala Lys Leu Ser Ser Val Gly Ser Ile Ser Glu Glu
1               5                   10                  15

Glu Thr Cys Glu Lys Leu Lys Gly Leu Ile Gln Arg Gln Val Gln Met
            20                  25                  30

Cys Lys Arg Asn Leu Glu Val Met Asp Ser Val Arg Arg Gly Ala Gln
35                  40                  45

Leu Ala Ile Glu Glu Cys Gln Tyr Gln Phe Arg Asn Arg Arg Trp Asn
    50                  55                  60

Cys Ser Thr Leu Asp Ser Leu Pro Val Phe Gly Lys Val Val Thr Gln
65                  70                  75                  80

Gly Thr Arg Glu Ala Ala Phe Val Tyr Ala Ile Ser Ser Ala Gly Val
                85                  90                  95

Ala Phe Ala Val Thr Arg Ala Cys Ser Ser Gly Glu Leu Glu Lys Cys
            100                 105                 110

Gly Cys Asp Arg Thr Val His Gly Val Ser Pro Gln Gly Phe Gln Trp
        115                 120                 125

Ser Gly Cys Ser Asp Asn Ile Ala Tyr Gly Val Ala Phe Ser Gln Ser
    130                 135                 140

Phe Val Asp Val Arg Glu Arg Ser Lys Gly Ala Ser Ser Ser Arg Ala
145                 150                 155                 160

Leu Met Asn Leu His Asn Asn Glu Ala Gly Arg Lys Ala Ile Leu Thr
                165                 170                 175

His Met Arg Val Glu Cys Lys Cys His Gly Val Ser Gly Ser Cys Glu
            180                 185                 190

Val Lys Thr Cys Trp Arg Ala Val Pro Pro Phe Arg Gln Val Gly His
        195                 200                 205

Ala Leu Lys Glu Lys Phe Asp Gly Ala Thr Glu Val Glu Pro Arg Arg
    210                 215                 220

Val Gly Ser Ser Arg Ala Leu Val Pro Arg Asn Ala Gln Phe Lys Pro
225                 230                 235                 240

His Thr Asp Glu Asp Leu Val Tyr Leu Glu Pro Ser Pro Asp Phe Cys
                245                 250                 255

Glu Gln Asp Met Arg Ser Gly Val Leu Gly Thr Arg Gly Arg Thr Cys
            260                 265                 270

Asn Lys Thr Ser Lys Ala Ile Asp Gly Cys Glu Leu Leu Cys Cys Gly
        275                 280                 285

Arg Gly Phe His Thr Ala Gln Val Glu Leu Ala Glu Arg Cys Ser Cys
    290                 295                 300

Lys Phe His Trp Cys Cys Phe Val Lys Cys Arg Gln Cys Gln Arg Leu
305                 310                 315                 320

Val Glu Leu His Thr Cys Arg
                325
```

<210> SEQ ID NO 44
<211> LENGTH: 317
<212> TYPE: PRT
<213> ORGANISM: Homo sapiens
<300> PUBLICATION INFORMATION:
<308> DATABASE ACCESSION NUMBER: P41221
<309> DATABASE ENTRY DATE: 2016-07-06
<313> RELEVANT RESIDUES IN SEQ ID NO: (64)..(380)

<400> SEQUENCE: 44

```
Gly Ala Gln Pro Leu Cys Ser Gln Leu Ala Gly Leu Ser Gln Gly Gln
1               5                   10                  15

Lys Lys Leu Cys His Leu Tyr Gln Asp His Met Gln Tyr Ile Gly Glu
            20                  25                  30

Gly Ala Lys Thr Gly Ile Lys Glu Cys Gln Tyr Gln Phe Arg His Arg
        35                  40                  45

Arg Trp Asn Cys Ser Thr Val Asp Asn Thr Ser Val Phe Gly Arg Val
    50                  55                  60

Met Gln Ile Gly Ser Arg Glu Thr Ala Phe Thr Tyr Ala Val Ser Ala
65                  70                  75                  80

Ala Gly Val Val Asn Ala Met Ser Arg Ala Cys Arg Glu Gly Glu Leu
                85                  90                  95

Ser Thr Cys Gly Cys Ser Arg Ala Ala Arg Pro Lys Asp Leu Pro Arg
            100                 105                 110

Asp Trp Leu Trp Gly Gly Cys Gly Asp Asn Ile Asp Tyr Gly Tyr Arg
        115                 120                 125

Phe Ala Lys Glu Phe Val Asp Ala Arg Glu Arg Glu Arg Ile His Ala
    130                 135                 140

Lys Gly Ser Tyr Glu Ser Ala Arg Ile Leu Met Asn Leu His Asn Asn
145                 150                 155                 160

Glu Ala Gly Arg Arg Thr Val Tyr Asn Leu Ala Asp Val Ala Cys Lys
                165                 170                 175

Cys His Gly Val Ser Gly Ser Cys Ser Leu Lys Thr Cys Trp Leu Gln
            180                 185                 190

Leu Ala Asp Phe Arg Lys Val Gly Asp Ala Leu Lys Glu Lys Tyr Asp
        195                 200                 205

Ser Ala Ala Ala Met Arg Leu Asn Ser Arg Gly Lys Leu Val Gln Val
    210                 215                 220

Asn Ser Arg Phe Asn Ser Pro Thr Thr Gln Asp Leu Val Tyr Ile Asp
225                 230                 235                 240

Pro Ser Pro Asp Tyr Cys Val Arg Asn Glu Ser Thr Gly Ser Leu Gly
                245                 250                 255

Thr Gln Gly Arg Leu Cys Asn Lys Thr Ser Glu Gly Met Asp Gly Cys
            260                 265                 270

Glu Leu Met Cys Cys Gly Arg Gly Tyr Asp Gln Phe Lys Thr Val Gln
        275                 280                 285

Thr Glu Arg Cys His Cys Lys Phe His Trp Cys Cys Tyr Val Lys Cys
    290                 295                 300

Lys Lys Cys Thr Glu Ile Val Asp Gln Phe Val Cys Lys
305                 310                 315
```

<210> SEQ ID NO 45
<211> LENGTH: 340
<212> TYPE: PRT
<213> ORGANISM: Homo sapiens
<300> PUBLICATION INFORMATION:
<308> DATABASE ACCESSION NUMBER: Q9H1J7
<309> DATABASE ENTRY DATE: 2016-07-06

<313> RELEVANT RESIDUES IN SEQ ID NO: (20)..(359)

<400> SEQUENCE: 45

Leu Thr Asp Ala Asn Ser Trp Trp Ser Leu Ala Leu Asn Pro Val Gln
1               5                   10                  15
Arg Pro Glu Met Phe Ile Ile Gly Ala Gln Pro Val Cys Ser Gln Leu
            20                  25                  30
Pro Gly Leu Ser Pro Gly Gln Arg Lys Leu Cys Gln Leu Tyr Gln Glu
        35                  40                  45
His Met Ala Tyr Ile Gly Gly Ala Lys Thr Gly Ile Lys Glu Cys
    50                  55                  60
Gln His Gln Phe Arg Gln Arg Trp Asn Cys Ser Thr Ala Asp Asn
65                  70                  75                  80
Ala Ser Val Phe Gly Arg Val Met Gln Ile Gly Ser Arg Glu Thr Ala
                85                  90                  95
Phe Thr His Ala Val Ser Ala Ala Gly Val Val Asn Ala Ile Ser Arg
            100                 105                 110
Ala Cys Arg Glu Gly Glu Leu Ser Thr Cys Gly Cys Ser Arg Thr Ala
        115                 120                 125
Arg Pro Lys Asp Leu Pro Arg Asp Trp Leu Trp Gly Gly Cys Gly Asp
    130                 135                 140
Asn Val Glu Tyr Gly Tyr Arg Phe Ala Lys Glu Phe Val Asp Ala Arg
145                 150                 155                 160
Glu Arg Glu Lys Asn Phe Ala Lys Gly Ser Glu Glu Gln Gly Arg Val
                165                 170                 175
Leu Met Asn Leu Gln Asn Asn Glu Ala Gly Arg Arg Ala Val Tyr Lys
            180                 185                 190
Met Ala Asp Val Ala Cys Lys Cys His Gly Val Ser Gly Ser Cys Ser
        195                 200                 205
Leu Lys Thr Cys Trp Leu Gln Leu Ala Glu Phe Arg Lys Val Gly Asp
    210                 215                 220
Arg Leu Lys Glu Lys Tyr Asp Ser Ala Ala Met Arg Val Thr Arg
225                 230                 235                 240
Lys Gly Arg Leu Glu Leu Val Asn Ser Arg Phe Thr Gln Pro Thr Pro
                245                 250                 255
Glu Asp Leu Val Tyr Val Asp Pro Ser Pro Asp Tyr Cys Leu Arg Asn
            260                 265                 270
Glu Ser Thr Gly Ser Leu Gly Thr Gln Gly Arg Leu Cys Asn Lys Thr
        275                 280                 285
Ser Glu Gly Met Asp Gly Cys Glu Leu Met Cys Cys Gly Arg Gly Tyr
    290                 295                 300
Asn Gln Phe Lys Ser Val Gln Val Glu Arg Cys His Cys Lys Phe His
305                 310                 315                 320
Trp Cys Cys Phe Val Arg Cys Lys Lys Cys Thr Glu Ile Val Asp Gln
                325                 330                 335
Tyr Ile Cys Lys
            340

<210> SEQ ID NO 46
<211> LENGTH: 339
<212> TYPE: PRT
<213> ORGANISM: Homo sapiens
<300> PUBLICATION INFORMATION:
<308> DATABASE ACCESSION NUMBER: Q9Y6F9
<309> DATABASE ENTRY DATE: 2016-07-06
<313> RELEVANT RESIDUES IN SEQ ID NO: (25)..(363)

<400> SEQUENCE: 46

```
Leu Trp Trp Ala Val Gly Ser Pro Leu Val Met Asp Pro Thr Ser Ile
1               5                   10                  15

Cys Arg Lys Ala Arg Arg Leu Ala Gly Arg Gln Ala Glu Leu Cys Gln
            20                  25                  30

Ala Glu Pro Glu Val Val Ala Glu Leu Ala Arg Gly Ala Arg Leu Gly
            35                  40                  45

Val Arg Glu Cys Gln Phe Gln Phe Arg Phe Arg Trp Asn Cys Ser
50                  55                  60

Ser His Ser Lys Ala Phe Gly Arg Ile Leu Gln Gln Asp Ile Arg Glu
65                  70                  75                  80

Thr Ala Phe Val Phe Ala Ile Thr Ala Ala Gly Ala Ser His Ala Val
                85                  90                  95

Thr Gln Ala Cys Ser Met Gly Glu Leu Leu Gln Cys Gly Cys Gln Ala
            100                 105                 110

Pro Arg Gly Arg Ala Pro Pro Arg Pro Ser Gly Leu Pro Gly Thr Pro
            115                 120                 125

Gly Pro Pro Gly Pro Ala Gly Ser Pro Glu Gly Ser Ala Ala Trp Glu
130                 135                 140

Trp Gly Gly Cys Gly Asp Asp Val Asp Phe Gly Asp Glu Lys Ser Arg
145                 150                 155                 160

Leu Phe Met Asp Ala Arg His Lys Arg Gly Arg Gly Asp Ile Arg Ala
                165                 170                 175

Leu Val Gln Leu His Asn Asn Glu Ala Gly Arg Leu Ala Val Arg Ser
            180                 185                 190

His Thr Arg Thr Glu Cys Lys Cys His Gly Leu Ser Gly Ser Cys Ala
            195                 200                 205

Leu Arg Thr Cys Trp Gln Lys Leu Pro Pro Phe Arg Glu Val Gly Ala
210                 215                 220

Arg Leu Leu Glu Arg Phe His Gly Ala Ser Arg Val Met Gly Thr Asn
225                 230                 235                 240

Asp Gly Lys Ala Leu Leu Pro Ala Val Arg Thr Leu Lys Pro Pro Gly
                245                 250                 255

Arg Ala Asp Leu Leu Tyr Ala Ala Asp Ser Pro Asp Phe Cys Ala Pro
            260                 265                 270

Asn Arg Arg Thr Gly Ser Pro Gly Thr Arg Gly Arg Ala Cys Asn Ser
            275                 280                 285

Ser Ala Pro Asp Leu Ser Gly Cys Asp Leu Leu Cys Cys Gly Arg Gly
290                 295                 300

His Arg Gln Glu Ser Val Gln Leu Glu Glu Asn Cys Leu Cys Arg Phe
305                 310                 315                 320

His Trp Cys Cys Val Val Gln Cys His Arg Cys Arg Val Arg Lys Glu
                325                 330                 335

Leu Ser Leu
```

<210> SEQ ID NO 47
<211> LENGTH: 316
<212> TYPE: PRT
<213> ORGANISM: Homo sapiens
<300> PUBLICATION INFORMATION:
<308> DATABASE ACCESSION NUMBER: O00755
<309> DATABASE ENTRY DATE: 2016-07-06
<313> RELEVANT RESIDUES IN SEQ ID NO: (34)..(349)

<400> SEQUENCE: 47

```
Ala Ser Ile Ile Cys Asn Lys Ile Pro Gly Leu Ala Pro Arg Gln Arg
1               5                   10                  15

Ala Ile Cys Gln Ser Arg Pro Asp Ala Ile Ile Val Ile Gly Glu Gly
            20                  25                  30

Ser Gln Met Gly Leu Asp Glu Cys Gln Phe Gln Phe Arg Asn Gly Arg
        35                  40                  45

Trp Asn Cys Ser Ala Leu Gly Glu Arg Thr Val Phe Gly Lys Glu Leu
    50                  55                  60

Lys Val Gly Ser Arg Glu Ala Ala Phe Thr Tyr Ala Ile Ile Ala Ala
65                  70                  75                  80

Gly Val Ala His Ala Ile Thr Ala Ala Cys Thr Gln Gly Asn Leu Ser
                85                  90                  95

Asp Cys Gly Cys Asp Lys Glu Lys Gln Gly Gln Tyr His Arg Asp Glu
            100                 105                 110

Gly Trp Lys Trp Gly Gly Cys Ser Ala Asp Ile Arg Tyr Gly Ile Gly
            115                 120                 125

Phe Ala Lys Val Phe Val Asp Ala Arg Glu Ile Lys Gln Asn Ala Arg
    130                 135                 140

Thr Leu Met Asn Leu His Asn Asn Glu Ala Gly Arg Lys Ile Leu Glu
145                 150                 155                 160

Glu Asn Met Lys Leu Glu Cys Lys Cys His Gly Val Ser Gly Ser Cys
                165                 170                 175

Thr Thr Lys Thr Cys Trp Thr Thr Leu Pro Gln Phe Arg Glu Leu Gly
            180                 185                 190

Tyr Val Leu Lys Asp Lys Tyr Asn Glu Ala Val His Val Glu Pro Val
        195                 200                 205

Arg Ala Ser Arg Asn Lys Arg Pro Thr Phe Leu Lys Ile Lys Lys Pro
    210                 215                 220

Leu Ser Tyr Arg Lys Pro Met Asp Thr Asp Leu Val Tyr Ile Glu Lys
225                 230                 235                 240

Ser Pro Asn Tyr Cys Glu Glu Asp Pro Val Thr Gly Ser Val Gly Thr
                245                 250                 255

Gln Gly Arg Ala Cys Asn Lys Thr Ala Pro Gln Ala Ser Gly Cys Asp
            260                 265                 270

Leu Met Cys Cys Gly Arg Gly Tyr Asn Thr His Gln Tyr Ala Arg Val
            275                 280                 285

Trp Gln Cys Asn Cys Lys Phe His Trp Cys Tyr Val Lys Cys Asn
            290                 295                 300

Thr Cys Ser Glu Arg Thr Glu Met Tyr Thr Cys Lys
305                 310                 315

<210> SEQ ID NO 48
<211> LENGTH: 323
<212> TYPE: PRT
<213> ORGANISM: Homo sapiens
<300> PUBLICATION INFORMATION:
<308> DATABASE ACCESSION NUMBER: P56706
<309> DATABASE ENTRY DATE: 2016-07-06
<313> RELEVANT RESIDUES IN SEQ ID NO: (27)..(349)

<400> SEQUENCE: 48

Ser Ser Val Val Ala Leu Gly Ala Asn Ile Ile Cys Asn Lys Ile Pro
1               5                   10                  15

Gly Leu Ala Pro Arg Gln Arg Ala Ile Cys Gln Ser Arg Pro Asp Ala
            20                  25                  30
```

```
Ile Ile Val Ile Gly Glu Gly Ala Gln Met Gly Ile Asn Glu Cys Gln
            35                  40                  45

Tyr Gln Phe Arg Phe Gly Arg Trp Asn Cys Ser Ala Leu Gly Glu Lys
    50                  55                  60

Thr Val Phe Gly Gln Glu Leu Arg Val Gly Ser Arg Glu Ala Ala Phe
65                  70                  75                  80

Thr Tyr Ala Ile Thr Ala Ala Gly Val Ala His Ala Val Thr Ala Ala
                85                  90                  95

Cys Ser Gln Gly Asn Leu Ser Asn Cys Gly Cys Asp Arg Glu Lys Gln
                100                 105                 110

Gly Tyr Tyr Asn Gln Ala Glu Gly Trp Lys Trp Gly Gly Cys Ser Ala
            115                 120                 125

Asp Val Arg Tyr Gly Ile Asp Phe Ser Arg Arg Phe Val Asp Ala Arg
        130                 135                 140

Glu Ile Lys Lys Asn Ala Arg Arg Leu Met Asn Leu His Asn Asn Glu
145                 150                 155                 160

Ala Gly Arg Lys Val Leu Glu Asp Arg Met Gln Leu Glu Cys Lys Cys
                165                 170                 175

His Gly Val Ser Gly Ser Cys Thr Thr Lys Thr Cys Trp Thr Thr Leu
                180                 185                 190

Pro Lys Phe Arg Glu Val Gly His Leu Leu Lys Glu Lys Tyr Asn Ala
            195                 200                 205

Ala Val Gln Val Glu Val Val Arg Ala Ser Arg Leu Arg Gln Pro Thr
        210                 215                 220

Phe Leu Arg Ile Lys Gln Leu Arg Ser Tyr Gln Lys Pro Met Glu Thr
225                 230                 235                 240

Asp Leu Val Tyr Ile Glu Lys Ser Pro Asn Tyr Cys Glu Glu Asp Ala
                245                 250                 255

Ala Thr Gly Ser Val Gly Thr Gln Gly Arg Leu Cys Asn Arg Thr Ser
                260                 265                 270

Pro Gly Ala Asp Gly Cys Asp Thr Met Cys Cys Gly Arg Gly Tyr Asn
            275                 280                 285

Thr His Gln Tyr Thr Lys Val Trp Gln Cys Asn Cys Lys Phe His Trp
        290                 295                 300

Cys Cys Phe Val Lys Cys Asn Thr Cys Ser Glu Arg Thr Glu Val Phe
305                 310                 315                 320

Thr Cys Lys

<210> SEQ ID NO 49
<211> LENGTH: 325
<212> TYPE: PRT
<213> ORGANISM: Homo sapiens
<300> PUBLICATION INFORMATION:
<308> DATABASE ACCESSION NUMBER: Q9H1J5
<309> DATABASE ENTRY DATE: 2016-07-06
<313> RELEVANT RESIDUES IN SEQ ID NO: (27)..(351)

<400> SEQUENCE: 49

Asn Phe Leu Ile Thr Gly Pro Lys Ala Tyr Leu Thr Tyr Thr Thr Ser
1               5                   10                  15

Val Ala Leu Gly Ala Gln Ser Gly Ile Glu Glu Cys Lys Phe Gln Phe
                20                  25                  30

Ala Trp Glu Arg Trp Asn Cys Pro Glu Asn Ala Leu Gln Leu Ser Thr
            35                  40                  45

His Asn Arg Leu Arg Ser Ala Thr Arg Glu Thr Ser Phe Ile His Ala
        50                  55                  60
```

```
Ile Ser Ser Ala Gly Val Met Tyr Ile Ile Thr Lys Asn Cys Ser Met
 65                  70                  75                  80

Gly Asp Phe Glu Asn Cys Gly Cys Asp Gly Ser Asn Asn Gly Lys Thr
                 85                  90                  95

Gly Gly His Gly Trp Ile Trp Gly Gly Cys Ser Asp Asn Val Glu Phe
            100                 105                 110

Gly Glu Arg Ile Ser Lys Leu Phe Val Asp Ser Leu Glu Lys Gly Lys
            115                 120                 125

Asp Ala Arg Ala Leu Met Asn Leu His Asn Asn Arg Ala Gly Arg Leu
130                 135                 140

Ala Val Arg Ala Thr Met Lys Arg Thr Cys Lys Cys His Gly Ile Ser
145                 150                 155                 160

Gly Ser Cys Ser Ile Gln Thr Cys Trp Leu Gln Leu Ala Glu Phe Arg
                165                 170                 175

Glu Met Gly Asp Tyr Leu Lys Ala Lys Tyr Asp Gln Ala Leu Lys Ile
            180                 185                 190

Glu Met Asp Lys Arg Gln Leu Arg Ala Gly Asn Ser Ala Glu Gly His
            195                 200                 205

Trp Val Pro Ala Glu Ala Phe Leu Pro Ser Ala Glu Ala Glu Leu Ile
210                 215                 220

Phe Leu Glu Glu Ser Pro Asp Tyr Cys Thr Cys Asn Ser Ser Leu Gly
225                 230                 235                 240

Ile Tyr Gly Thr Glu Gly Arg Glu Cys Leu Gln Asn Ser His Asn Thr
                245                 250                 255

Ser Arg Trp Glu Arg Arg Ser Cys Gly Arg Leu Cys Thr Glu Cys Gly
            260                 265                 270

Leu Gln Val Glu Glu Arg Lys Thr Glu Val Ile Ser Ser Cys Asn Cys
            275                 280                 285

Lys Phe Gln Trp Cys Cys Thr Val Lys Cys Asp Gln Cys Arg His Val
            290                 295                 300

Val Ser Lys Tyr Tyr Cys Ala Arg Ser Pro Gly Ser Ala Gln Ser Leu
305                 310                 315                 320

Gly Lys Gly Ser Ala
                325

<210> SEQ ID NO 50
<211> LENGTH: 327
<212> TYPE: PRT
<213> ORGANISM: Homo sapiens
<300> PUBLICATION INFORMATION:
<308> DATABASE ACCESSION NUMBER: Q93098
<309> DATABASE ENTRY DATE: 2016-07-06
<313> RELEVANT RESIDUES IN SEQ ID NO: (25)..(351)

<400> SEQUENCE: 50

Val Asn Asn Phe Leu Met Thr Gly Pro Lys Ala Tyr Leu Ile Tyr Ser
1               5                   10                  15

Ser Ser Val Ala Ala Gly Ala Gln Ser Gly Ile Glu Glu Cys Lys Tyr
                20                  25                  30

Gln Phe Ala Trp Asp Arg Trp Asn Cys Pro Glu Arg Ala Leu Gln Leu
            35                  40                  45

Ser Ser His Gly Gly Leu Arg Ser Ala Asn Arg Glu Thr Ala Phe Val
        50                  55                  60

His Ala Ile Ser Ser Ala Gly Val Met Tyr Thr Leu Thr Arg Asn Cys
 65                 70                  75                  80
```

Ser Leu Gly Asp Phe Asp Asn Cys Gly Cys Asp Asp Ser Arg Asn Gly
            85                  90                  95

Gln Leu Gly Gly Gln Gly Trp Leu Trp Gly Gly Cys Ser Asp Asn Val
        100                 105                 110

Gly Phe Gly Glu Ala Ile Ser Lys Gln Phe Val Asp Ala Leu Glu Thr
        115                 120                 125

Gly Gln Asp Ala Arg Ala Ala Met Asn Leu His Asn Asn Glu Ala Gly
    130                 135                 140

Arg Lys Ala Val Lys Gly Thr Met Lys Arg Thr Cys Lys Cys His Gly
145                 150                 155                 160

Val Ser Gly Ser Cys Thr Thr Gln Thr Cys Trp Leu Gln Leu Pro Glu
                165                 170                 175

Phe Arg Glu Val Gly Ala His Leu Lys Glu Lys Tyr His Ala Ala Leu
            180                 185                 190

Lys Val Asp Leu Leu Gln Gly Ala Gly Asn Ser Ala Ala Gly Arg Gly
        195                 200                 205

Ala Ile Ala Asp Thr Phe Arg Ser Ile Ser Thr Arg Glu Leu Val His
    210                 215                 220

Leu Glu Asp Ser Pro Asp Tyr Cys Leu Glu Asn Lys Thr Leu Gly Leu
225                 230                 235                 240

Leu Gly Thr Glu Gly Arg Glu Cys Leu Arg Arg Gly Arg Ala Leu Gly
                245                 250                 255

Arg Trp Glu Arg Arg Ser Cys Arg Arg Leu Cys Gly Asp Cys Gly Leu
            260                 265                 270

Ala Val Glu Glu Arg Arg Ala Glu Thr Val Ser Ser Cys Asn Cys Lys
        275                 280                 285

Phe His Trp Cys Cys Ala Val Arg Cys Glu Gln Cys Arg Arg Arg Val
    290                 295                 300

Thr Lys Tyr Phe Cys Ser Arg Ala Glu Arg Pro Gly Gly Ala Ala
305                 310                 315                 320

His Lys Pro Gly Arg Lys Pro
                325

<210> SEQ ID NO 51
<211> LENGTH: 334
<212> TYPE: PRT
<213> ORGANISM: Homo sapiens
<300> PUBLICATION INFORMATION:
<308> DATABASE ACCESSION NUMBER: O14904
<309> DATABASE ENTRY DATE: 2016-07-06
<313> RELEVANT RESIDUES IN SEQ ID NO: (32)..(365)

<400> SEQUENCE: 51

Gly Leu Thr Gly Ser Glu Pro Leu Thr Ile Leu Pro Leu Thr Leu Glu
1               5                   10                  15

Pro Glu Ala Ala Ala Gln Ala His Tyr Lys Ala Cys Asp Arg Leu Lys
            20                  25                  30

Leu Glu Arg Lys Gln Arg Arg Met Cys Arg Arg Asp Pro Gly Val Ala
        35                  40                  45

Glu Thr Leu Val Glu Ala Val Ser Met Ser Ala Leu Glu Cys Gln Phe
    50                  55                  60

Gln Phe Arg Phe Glu Arg Trp Asn Cys Thr Leu Glu Gly Arg Tyr Arg
65                  70                  75                  80

Ala Ser Leu Leu Lys Arg Gly Phe Lys Glu Thr Ala Phe Leu Tyr Ala
                85                  90                  95

Ile Ser Ser Ala Gly Leu Thr His Ala Leu Ala Lys Ala Cys Ser Ala

```
            100                 105                 110
Gly Arg Met Glu Arg Cys Thr Cys Asp Glu Ala Pro Asp Leu Glu Asn
            115                 120                 125

Arg Glu Ala Trp Gln Trp Gly Gly Cys Gly Asp Asn Leu Lys Tyr Ser
    130                 135                 140

Ser Lys Phe Val Lys Glu Phe Leu Gly Arg Ser Ser Lys Asp Leu
145                 150                 155                 160

Arg Ala Arg Val Asp Phe His Asn Asn Leu Val Gly Val Lys Val Ile
                165                 170                 175

Lys Ala Gly Val Glu Thr Thr Cys Lys Cys His Gly Val Ser Gly Ser
            180                 185                 190

Cys Thr Val Arg Thr Cys Trp Arg Gln Leu Ala Pro Phe His Glu Val
        195                 200                 205

Gly Lys His Leu Lys His Lys Tyr Glu Thr Ala Leu Lys Val Gly Ser
    210                 215                 220

Thr Thr Asn Glu Ala Ala Gly Glu Ala Gly Ala Ile Ser Pro Pro Arg
225                 230                 235                 240

Gly Arg Ala Ser Gly Ala Gly Gly Ser Asp Pro Leu Pro Arg Thr Pro
                245                 250                 255

Glu Leu Val His Leu Asp Asp Ser Pro Ser Phe Cys Leu Ala Gly Arg
                260                 265                 270

Phe Ser Pro Gly Thr Ala Gly Arg Arg Cys His Arg Glu Lys Asn Cys
            275                 280                 285

Glu Ser Ile Cys Cys Gly Arg Gly His Asn Thr Gln Ser Arg Val Val
        290                 295                 300

Thr Arg Pro Cys Gln Cys Gln Val Arg Trp Cys Cys Tyr Val Glu Cys
305                 310                 315                 320

Arg Gln Cys Thr Gln Arg Glu Glu Val Tyr Thr Cys Lys Gly
                325                 330

<210> SEQ ID NO 52
<211> LENGTH: 172
<212> TYPE: PRT
<213> ORGANISM: Homo sapiens
<300> PUBLICATION INFORMATION:
<308> DATABASE ACCESSION NUMBER: Q15465
<309> DATABASE ENTRY DATE: 2016-07-06
<313> RELEVANT RESIDUES IN SEQ ID NO: (24)..(195)

<400> SEQUENCE: 52

Cys Gly Pro Gly Arg Gly Phe Gly Lys Arg Arg His Pro Lys Lys Leu
1               5                   10                  15

Thr Pro Leu Ala Tyr Lys Gln Phe Ile Pro Asn Val Ala Glu Lys Thr
            20                  25                  30

Leu Gly Ala Ser Gly Arg Tyr Glu Gly Lys Ile Ser Arg Asn Ser Glu
        35                  40                  45

Arg Phe Lys Glu Leu Thr Pro Asn Tyr Asn Pro Asp Ile Ile Phe Lys
    50                  55                  60

Asp Glu Glu Asn Thr Gly Ala Asp Arg Leu Met Thr Gln Arg Cys Lys
65                  70                  75                  80

Asp Lys Leu Asn Ala Leu Ala Ile Ser Val Met Asn Gln Trp Pro Gly
                85                  90                  95

Val Lys Leu Arg Val Thr Glu Gly Trp Asp Glu Asp Gly His His Ser
            100                 105                 110

Glu Glu Ser Leu His Tyr Glu Gly Arg Ala Val Asp Ile Thr Thr Ser
        115                 120                 125
```

Asp Arg Asp Arg Ser Lys Tyr Gly Met Leu Ala Arg Leu Ala Val Glu
            130                 135                 140

Ala Gly Phe Asp Trp Val Tyr Glu Ser Lys Ala His Ile His Cys
145                 150                 155                 160

Ser Val Lys Ala Glu Asn Ser Val Ala Ala Lys Ser
                165                 170

<210> SEQ ID NO 53
<211> LENGTH: 174
<212> TYPE: PRT
<213> ORGANISM: Homo sapiens
<300> PUBLICATION INFORMATION:
<308> DATABASE ACCESSION NUMBER: O43323
<309> DATABASE ENTRY DATE: 2016-07-06
<313> RELEVANT RESIDUES IN SEQ ID NO: (23)..(196)

<400> SEQUENCE: 53

Cys Gly Pro Gly Arg Gly Pro Val Gly Arg Arg Arg Tyr Ala Arg Lys
1               5                   10                  15

Gln Leu Val Pro Leu Leu Tyr Lys Gln Phe Val Pro Gly Val Pro Glu
            20                  25                  30

Arg Thr Leu Gly Ala Ser Gly Pro Ala Glu Gly Arg Val Ala Arg Gly
        35                  40                  45

Ser Glu Arg Phe Arg Asp Leu Val Pro Asn Tyr Asn Pro Asp Ile Ile
50                  55                  60

Phe Lys Asp Glu Glu Asn Ser Gly Ala Asp Arg Leu Met Thr Glu Arg
65                  70                  75                  80

Cys Lys Glu Arg Val Asn Ala Leu Ala Ile Ala Val Met Asn Met Trp
                85                  90                  95

Pro Gly Val Arg Leu Arg Val Thr Glu Gly Trp Asp Glu Asp Gly His
            100                 105                 110

His Ala Gln Asp Ser Leu His Tyr Glu Gly Arg Ala Leu Asp Ile Thr
        115                 120                 125

Thr Ser Asp Arg Asp Arg Asn Lys Tyr Gly Leu Leu Ala Arg Leu Ala
130                 135                 140

Val Glu Ala Gly Phe Asp Trp Val Tyr Tyr Glu Ser Arg Asn His Val
145                 150                 155                 160

His Val Ser Val Lys Ala Asp Asn Ser Leu Ala Val Arg Ala
                165                 170

<210> SEQ ID NO 54
<211> LENGTH: 173
<212> TYPE: PRT
<213> ORGANISM: Homo sapiens
<300> PUBLICATION INFORMATION:
<308> DATABASE ACCESSION NUMBER: Q14623
<309> DATABASE ENTRY DATE: 2016-07-06
<313> RELEVANT RESIDUES IN SEQ ID NO: (28)..(200)

<400> SEQUENCE: 54

Cys Gly Pro Gly Arg Val Val Gly Ser Arg Arg Arg Pro Pro Arg Lys
1               5                   10                  15

Leu Val Pro Leu Ala Tyr Lys Gln Phe Ser Pro Asn Val Pro Glu Lys
            20                  25                  30

Thr Leu Gly Ala Ser Gly Arg Tyr Glu Gly Lys Ile Ala Arg Ser Ser
        35                  40                  45

Glu Arg Phe Lys Glu Leu Thr Pro Asn Tyr Asn Pro Asp Ile Ile Phe
50                  55                  60

```
Lys Asp Glu Glu Asn Thr Gly Ala Asp Arg Leu Met Thr Gln Arg Cys
 65                  70                  75                  80

Lys Asp Arg Leu Asn Ser Leu Ala Ile Ser Val Met Asn Gln Trp Pro
                 85                  90                  95

Gly Val Lys Leu Arg Val Thr Glu Gly Trp Asp Glu Asp Gly His His
            100                 105                 110

Ser Glu Glu Ser Leu His Tyr Glu Gly Arg Ala Val Asp Ile Thr Thr
        115                 120                 125

Ser Asp Arg Asp Arg Asn Lys Tyr Gly Leu Leu Ala Arg Leu Ala Val
    130                 135                 140

Glu Ala Gly Phe Asp Trp Val Tyr Tyr Glu Ser Lys Ala His Val His
145                 150                 155                 160

Cys Ser Val Lys Ser Glu His Ser Ala Ala Ala Lys Thr
            165                 170
```

METHOD OF TREATING PAIN USING AGENTS THAT PROMOTE NEURONAL DIFFERENTIATION

CROSS REFERENCE TO RELATED APPLICATIONS

This application is based on and claims priority to U.S. Provisional Application Ser. No. 62/365,615, filed Jun. 30, 2016, herein incorporated in its entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

SEQUENCE LISTING

The instant application contains a Sequence Listing, which has been submitted in ASCII format via EFS-Web and is hereby incorporated by reference in its entirety. Said ASCII copy, created on Aug. 21, 2016, is named PRODIF_ST25.txt and is 112882 bytes in size.

STATEMENT REGARDING PRIOR DISCLOSURES BY THE INVENTOR OR A JOINT INVENTOR

Not Applicable

BACKGROUND OF THE INVENTION (1) Field of the Invention

The presently disclosed subject matter generally relates to the treatment of disorders in a subject, including but not limited to pain. More particularly, the methods of the presently disclosed subject matter relate to using promoters of neuronal differentiation to induce the differentiation and maturation of immature neuron cells, for the purpose of reducing pain and the susceptibility to pain.

(2) Description of Related Art

Not Applicable

TABLE OF ABREVIATIONS

| | |
|---|---|
| AAV | adeno-associated virus |
| ARTN | artemin |
| AV | adenovirus |
| BDNF | brain-derived neurotrophic factor |
| BSA | bovine serum albumin |
| CCI | chronic constriction injury model of chronic pain, in which a ligature is tied to the sciatic nerve, inflicting chronic pain |
| cDNA | complementary DNA |
| Cl | chloride |
| CNTF | ciliary neurotrophic factor |
| Contra | Contralateral, on the opposite side |
| DCX | Doublecortin |
| Dhh | Desert hedgehog |
| DNA | deoxyribonucleic acid |
| E. coli | Escherichia coli |
| EdU | ethynyl-deoxyuridine |
| EGF | epidermal growth factor |
| EPO | erythropoietin |
| FGF2 | fibroblast growth factor 2 |
| FZD | frizzled receptor |
| GABA | gamma-aminobutiric acid |
| GDL | GDNF family of ligands |
| GDNF | glial cell derived neurotrophic factor |
| GF | growth factors |
| HGF | hepatocyte growth factor |
| Hh | Hedgehog |
| Ihh | Indian hedgehog |
| INH | inhibitors |
| iPSCs | induced pluripotent stem cells |
| Ipsi | ipsilateral, on the same side |
| IUPAC | International Union of Pure and Applied Chemistry |
| K | potassium |
| ko | gene knock-out |
| LIF | leukemia inhibitory factor |
| Mash1 | mammalian achaete-scute homolog 1 |
| ml | milliliter |
| N3 | Notch3 |
| Na | sodium |
| NCC2 | sodium-chloride cotransporter 2 |
| NGF | nerve growth factor |
| NKCC1 | sodium-potassium-chloride cotransporter 1 |
| NRTN | neurturin |
| NT3 | neurotrophin 3 |
| NT4 | neurotrophin 4 |
| PBS | phosphate buffer saline |
| PSPN | persephin |
| PTCH | Patched receptor |
| Shh | Sonic hedgehog |
| SMO | Smoothened receptor |
| TetO | tetracycline operator sequence |
| TrkA | tropomyosin receptor kinase A |
| TrkB | tropomyosin receptor kinase B |
| TrkC | tropomyosin receptor kinase C |
| Veh | saline vehicle solution |
| Wnt | Wingless |
| WT | wild-type |

All amino-acid symbols used herein, including the Sequence Listing, are the three-letter abbreviations commonly used in the field of the invention.

BACKGROUND

Pain is an animal sensorial perception that indicates the presence of dangerous environmental conditions, prompting the organism to withdraw and adopt a protective stance in order to avoid injury, or to help heal an existing injury. The skin (epidermis and dermis) contains several types of receptors specialized in responses to mechanical, thermal and chemical (inflammation) stimuli, as well as poly-modal receptors. These receptors send nerve projections to the spinal cord, where the painful stimuli are processed, and a conscious or unconscious avoidance reaction is initiated.

The sensorial perception generated by specialized skin receptors and transmitted through nerves to the spinal cord is referred to as "nociception". The processing of nociceptive information in the brain and its interaction with other cognitive and affective processes is referred to as "pain". Since pain typically requires the input of nociceptive information, herein pain and nociception will be used interchangeably.

Pain can be classified as acute or chronic. Acute pain usually recedes after the elimination of the stimulus or healing of the injury. Chronic pain is often associated with chronic diseases, such as cancer or neurodegenerative disorders, but in many cases chronic pain can persist after the healing of the injury or disorder that have initiated it. Sometimes chronic pain can exist in the absence of any initiating conditions, such as fibromyalgia. Such cases are assumed to derive from genetic conditions. While acute pain is helpful in protecting the organism against injury, chronic pain has no benefit and interferes with normal activity. As a result, many classes of medication have been generated for the purpose of reducing or eliminating chronic pain.

All types of pain medication currently in use are targeted either against inflammation, or to reduce neuronal excitability by activating inhibitory receptors, such as GABA or opioid receptors, or by blocking the activation of excitatory sodium channels. Because of their mechanism of action, such medication is inevitably short-acting, effective only for as long as the active compound in the medication is bound to the receptor or ion channel, usually for several hours. Therefore, to maintain an analgesic effect, currently existing pain medication needs to be administered chronically throughout the duration of pain. Since such medication only addresses the symptoms of pain, not its cause, pain medication in general is considered to be "palliative", not curative.

Chronic administration of a drug will inevitably lead to an increased expression of the receptor or ion channel which it targets, in order to compensate for the inhibition of its activity. This will require a continually increasing dose of medication in order to maintain the same level of analgesia, gradually leading to addiction. Addiction to analgesics is a frequent and serious health and social problem. Analgesics overdose can often lead to death.

Chronic pain caused by genetic factors often does not respond to any type of analgesic medication. In most cases, the genetic factors leading to chronic pain are unknown. Several transgenic mouse lines exist that show increased nociceptive sensitivity, including c-kit (Milenkovic, et al., Neuron 56: 893-906 (2007)), aldehyde dehydrogenase-2 (Zambelli, et al., Sci Transl Med. 6: 251ra118 (2014)), Notch3 ko (Rusanescu, et al., J Cell Mol Med. 18: 2103-16 (2014)) and Shp2 (Vegunta, et al., Am J Med Genet A. 167A: 2998-3005 (2015)).

Immature spinal cord neurons play a key role in the perception of pain (Rusanescu, et al., J Cell Mol Med. 19: 2352-2364 (2015)). Adult neurogenesis occurs in the spinal cord under normal conditions (Schechter, et al., Stem Cells. 25: 2277-2282 (2007); Horner, et al., J Neurosci. 20: 2218-28(2000); Hugnot, et al., Frontiers Biosci. 16, 1044-59 (2011)), and is often amplified under pathological conditions such as injury (Rusanescu, et al., J Cell Mol Med. 19: 2352-2364 (2015)) or neurodegenerative disorders (Chi, et al., Stem Cells, 24: 34-43 (2006); Danilov, et al. Eur J Neurosci. 23, 394-400 (2006)). In one example, experimental chronic constriction injury of the sciatic nerve (CCI) induces significant cell proliferation in the spinal cord half ipsilateral to the injured nerve (FIG. 1). As a result, immature neurons are constantly generated and accumulate in the upper layers of the spinal cord dorsal horn (layers I-IV), responsible for nociceptive signaling (Rusanescu, et al., J Cell Mol Med. 19: 2352-2364 (2015)).

Immature neurons have high intracellular [$Cl^-$] concentration because of an increased expression of the Na+K+ 2Cl-cotransporter NKCC1 (Yamada et al., J Physiol. 557: 829-41 (2004)), and therefore depolarize in response to GABA during their early development (LoTurco et al., Neuron 15: 1287-1298 (1995)). In addition, immature neurons have higher resting membrane potential (−50 mV) and higher excitability (Belleau et al., J Neurophysiol. 84: 2204-16 (2000); Ben-Ari et al., Physiol Rev. 87, 1215-84 (2007)). Upon maturation, changes in the relative expression of NKCC1/KCC2 cotransporters result in decreased intracellular $Cl^-$ concentration and a hyperpolarizing response to GABA (Yamada et al., J Physiol. 557: 829-41 (2004)). A similar NKCC1/NCC2 expression reversal occurs in spinal cord dorsal horns after peripheral nerve injury (Price et al., Curr Top Med Chem. 5: 547-55 (2005); Lu et al, 2008), suggesting that these cells are immature neurons (Rusanescu, et al., J Cell Mol Med. 19: 2352-2364 (2015)).

Neurotrophins, including nerve growth factor (NGF), brain-derived neurotrophic factor (BDNF), neurotrophin 3 (NT3) and neurotrophin 4 (NT4), have very similar neurotrophic and neuronal differentiation effects. Neurotrophins have been considered since their discovery to be promoters of nociception (Lewin et al., Trends Neurosci. 16: 353-359 (1993); Jankovski et al., Transl Pain Res. Chapter 2 (2010); Khan et al., Molecules. 20: 10657-88 (2015)). Although this increased nociception only occurs in the short term (hours to days), the pro-nociceptive role of neurotrophins is generally accepted as a scientific standard. Based on this idea, pain therapies currently under development are focusing on the inhibition of neurotrophin signaling (Shelton, J Peripher Nery Syst. 19 Suppl 2:S12-3 (2014)).

Ciliary neurotrophic factor (CNTF) has a similar neurotrophic and differentiating function to neurotrophins, and has been considered to have a similar role in pain physiology. Current attempts to treat pain have included the inhibition of CNTF signaling (Yang et al., Curr Gene Ther. 14:377-88 (2014)).

The glial-derived neurotrophic factor family of ligands (GDL), including glial cell-derived neurotrophic factor (GDNF), artemin (ARTN), neurturin (NRTN) and persephin (PSPN), have a similar neurotrophic and differentiating function to neurotrophins, and are considered to have a pain-inducing effect similar to neurotrophins. As a result, current strategies in pain treatment include the inhibition of GDL signaling (Merighi, Expert Opin Ther Targets 20:193-208 (2016); Lippoldt et al., Proc Natl Acad Sci USA 113:4506-11 (2016)).

The leukemia inhibitory factor (LIF) is considered to be a promoter of pain, in conjunction with, or independently of neurotrophins (Thompson et al., Neuroscience 71:1091-94 (1996); Engert et al., Neuropeptides 42:193-7 (2008)). At the same time, LIF is also a promoter of neuronal differentiation (Majumder et al., Stem Cells 30:2387-99 (2012)).

Angiotensin is known to be a promoter of pain (Marion et al., Cell 157:1565-76 (2014)), and at the same time it is an inducer of neuronal differentiation (Li et al., Mol Endocrinol. 21:499-511(2007)).

Wnt is known to be a promoter of pain (Shi et al., Mol Pain 8:47 (2012); Liu et al., Pain 156:2572-84 (2015)), and at the same time it is an inducer of neuronal differentiation (Inestrosa et al., Cell Tissue Res. 359:215-23 (2015)).

Hh is known to be a promoter of pain (Babcock et al., Curr Biol. 21:1525-33 (2011)), and at the same time it is an inducer of neuronal differentiation (Dessaud et al., Development 135:2489-502 (2008)).

BRIEF SUMMARY OF THE INVENTION

The increase in nociceptive sensitivity after experimental spinal nerve injury (Bennett et al., Pain. 33: 87-107 (1988)) correlates with the increase in the number of spinal cord dorsal horn immature neurons (Rusanescu, et al., J Cell Mol Med. 19: 2352-2364 (2015)). This suggests that sensitivity to pain is determined by the number of highly excitable immature neurons in the dorsal horn. As a result, according to this model, any treatments that induce the differentiation of the hyper-excitable spinal cord immature neurons into mature neurons with low excitability would have an analgesic effect.

The idea that the level of pain is regulated by the number of immature spinal cord neurons is supported by the observation that all the proteins implicated in genetic models of pain, as described in paragraph [0009], are also coincidentally involved in neuronal differentiation: c-kit (Zhang, et al., Dev Neurosci. 31: 202-11 (2009)), aldehyde dehydrogenase-2 (Wallen A, et al., Exp Cell Res. 253, 737-46 (1999)), Notch3 (Rusanescu, et al., J Cell Mol Med. 18: 2103-16 (2014)), and Shp2 (Hadari Y R, et al., Mol Cell Biol. 18: 3966-73 (1998)). This idea was suggested by the correlation between the increased number of spinal cord immature neurons and increased pain sensitivity in Notch3 ko mice (Rusanescu, et al., J Cell Mol Med. 18: 2103-16 (2014)).

The present invention describes the use of agents that promote neuronal differentiation as a new class of analgesic drugs, the action of which is based on inducing the long-term differentiation of the highly excitable spinal cord immature neurons and thus reducing pain sensitivity. In the examples shown in this application, the said compounds reduce or eliminate pain in the long term. This effect is only apparently in contradiction with current knowledge that the same agents produce short-term pain.

The invention includes the use of polypeptides identical or similar to human neurotrophins, including BDNF (SEQ ID NO:1), NGF (SEQ ID NO:2), NT3 (SEQ ID NO:3), and NT4 (SEQ ID NO:4), in the treatment of pain. Another embodiment of this invention comprises the use of synthetic, semi-synthetic or natural molecules, which maintain functional similarity with human BDNF, NGF, NT3, or NT4, in activating members of the Trk family of receptors, for the purpose of treating pain.

Another embodiment of the invention includes the use of polypeptides identical or similar to the human CNTF (SEQ ID NO:5) in the treatment of pain. Another embodiment of this invention comprises the use of synthetic, semi-synthetic or natural molecules, which maintain functional similarity with human CNTF in activating the CNTF receptor, for the purpose of pain treatment.

Another embodiment of the invention includes the use of polypeptides identical or similar to the human GDNF family of ligands (GDL), including GDNF (SEQ ID NO:6), artemin (ARTN) (SEQ ID NO:7), neurturin (NRTN) (SEQ ID NO:8), and persephin (PSPN) (SEQ ID NO:9) in the treatment of pain. Another embodiment of this invention comprises the use of synthetic, semi-synthetic or natural molecules, which maintain functional similarity with human GDNF, ARTN, NRTN, or PSPN, in activating the RET receptor for the purpose of pain treatment.

Another embodiment of the present invention includes the use of a polypeptide identical or similar to the human leukemia inhibitory factor (LIF) (SEQ ID NO:10), in the treatment of pain. Another embodiment of this invention comprises the use of synthetic, semi-synthetic or natural molecules which maintain functional similarity with human LIF in activating the LIF receptor for the purpose of pain treatment.

Another embodiment of the present invention includes the use of a polypeptide identical or similar to the human angiotensin II (SEQ ID NO:11), in the treatment of pain. Another embodiment of this invention comprises the use of synthetic or natural molecules which maintain functional similarity with human angiotensin II in activating the angiotensin receptors, for the purpose of pain treatment.

Another embodiment of the present invention comprises the use of synthetic or natural molecules which promote directly or indirectly the activation of the c-Met receptor, for the purpose of pain treatment.

Another embodiment of the present invention includes the use of polypeptides identical or similar to the human Wnt, including Wnt1 (SEQ ID NO:12), Wnt2 (SEQ ID NO:13), Wnt2b (SEQ ID NO:14), Wnt3 (SEQ ID NO:15), Wnt4 (SEQ ID NO:16), Wnt5a (SEQ ID NO:17), Wnt5b (SEQ ID NO:18), Wnt6 (SEQ ID NO:19), Wnt7a (SEQ ID NO:20), Wnt7b (SEQ ID NO:21), Wnt8a (SEQ ID NO:22), Wnt8b (SEQ ID NO:23), and Wnt9a (SEQ ID NO:24), in the treatment of pain. Another embodiment of this invention comprises the use of synthetic, semi-synthetic or natural molecules which have functional similarity with human Wnt in promoting the activation of the frizzled (FZD) receptors for the purpose of pain treatment.

Another embodiment of the present invention includes the use of polypeptides identical or similar to the human Hh, including Shh (SEQ ID NO:25), Dhh (SEQ ID NO:26), and Ihh (SEQ ID NO:27) in the treatment of pain. Another embodiment of this invention comprises the use of synthetic or natural molecules which maintain functional similarity with human Hh in promoting the activation of the Smoothened (SMO) receptor for the purpose of pain treatment.

BRIEF DESCRIPTION OF THE FIGURES

FIG. 1 depicts the quantification of immunofluorescence staining of cell proliferation marker EdU in rat spinal cord slices, before (week 0) and at 2, 4 weeks after unilateral CCI. EdU staining was quantified as a percentage of the grey matter area, in the ipsilateral and contralateral halves of rat spinal cord. EdU staining is substantially increased ipsilaterally four weeks after CCI, at a time when inflammation-induced gliosis is reduced back to background level. This suggests that at least part of the EdU-stained proliferating cells reflect adult neurogenesis.

FIG. 2 depicts the quantification of nestin expression in rat spinal cord dorsal horns, before (week 0) and at 2, 4, 6 weeks after unilateral CCI. Nestin expression was quantified by immunofluorescence, as a percentage of ipsilateral and contralateral dorsal horn areas, respectively. Nestin is a marker for neuron precursor cells.

FIG. 3 depicts the quantification of Mash1 expression in rat spinal cord gray matter, before (week 0) and at 2, 4, 6 weeks after unilateral CCI. Mash1 expression was quantified by immunofluorescence, as a percentage of the ipsilateral and contralateral halves of the spinal cord gray matter area. Mash1 expression peaks at week 4 after CCI, which coincides with the time required for the newly generated neural progenitor cells to migrate from the central canal of the spinal cord to the upper dorsal horn. The contralateral increase in Mash1 expression is localized for the most part in the ventral horn and therefore is irrelevant for pain perception. Mash1 is a marker for neuron precursor cells.

FIG. 4 depicts the quantification of doublecortin (DCX) expression in rat spinal cord gray matter, before (week 0) and at 2, 4, 6 weeks after unilateral CCI. Doublecortin expression was quantified by immunofluorescence, as a percentage of the ipsilateral and contralateral halves of the spinal cord gray matter area. Doublecortin is a marker for immature neurons.

FIG. 5 depicts the quantification of Notch3 expression in rat spinal cord gray matter, before (week 0) and at 2, 4, 6 weeks after unilateral CCI. Notch3 expression was quantified by immunofluorescence, as a percentage of the ipsilateral and contralateral halves of the spinal cord gray matter area. Notch3 is a marker for neuron progenitor cells and immature neurons.

FIG. 6 depicts the increase in the number of NeuN-positive mature neurons in the ipsilateral spinal cord dorsal horn layers I and II, six weeks after unilateral CCI. NeuN expression, which is a marker for mature neurons, was quantified by immunofluorescence.

FIG. 7 depicts the weekly variation of nociceptive sensitivity on the ipsilateral (Ipsi, A and B) and contralateral hind paws (Contra, C and D) of rats subjected to unilateral CCI. Mechanical nociceptive sensitivity shown in A and C was measured using a von Frey series of filaments calibrated in grams. Thermal nociceptive sensitivity shown in B and D was measured in seconds as the withdrawal time after a beam of radiant light was applied to the paw. Arrows shown in A, B and C indicate inflexion points in the graph, which suggest a change in mechanism. The CCI graphs are depicted in comparison to reference graphs (Sham), which represent nociceptive sensitivity in rats subjected to sham surgery (surgery was performed as in CCI rats, but without performing nerve constriction). Asterisks indicate the statistical probability that the inflection points are a random occurrence. Using a generally accepted convention, "*" indicates a statistical probability $0.01 \leq P \leq 0.05$, "" indicates a statistical probability $0.001 \leq P \leq 0.01$ and "*" indicates a statistical probability $P<0.001$. Error bars indicate standard error.

FIG. 8 depicts the correlation between the number of immature neurons present in the spinal cord and the changes in nociceptive sensitivity. (A) depicts the variation in the expression of immature neuron markers Mash1, doublecortin and Notch3 in rat spinal cord ipsilateral and contralateral gray matter halves, 4 weeks after the rats were subjected to CCI and treated either with spinal (intrathecal) injections of saline (CCI+Veh), of inhibitors for EGF and FGF2 (CCI+INH), or of recombinant EGF and FGF2 (CCI+GF). Marker expression was quantified by immunofluorescence, as a percentage of the areas of the ipsilateral and contralateral gray matter halves, respectively. (B) depicts the weekly variation of the mechanical nociceptive sensitivity, measured in grams of pressure, on the paw ipsilateral to CCI, after injection with Veh or INH. (C) depicts the weekly variation of the thermal nociceptive sensitivity, measured in seconds of withdrawal latency, on the paw ipsilateral to CCI, after injection with Veh or INH. (D) depicts the weekly variation of the mechanical nociceptive sensitivity, measured in grams of pressure, on the paw ipsilateral to CCI, after injection with Veh or GF. (E) depicts the weekly variation of the thermal nociceptive sensitivity, measured in seconds of withdrawal latency, on the paw ipsilateral to CCI, after injection with Veh or GF. Statistical analysis is depicted as in FIG. 7.

FIG. 9 depicts the effect of BDNF treatment on the number of spinal cord immature neurons in parallel with its effect on nociceptive sensitivity. (A) depicts the variations in the expression of immature neuron markers Mash1, doublecortin and Notch3 in rat spinal cord ipsilateral and contralateral gray matter halves, 6 weeks after the rats were subjected to CCI and treated with intrathecal injections of saline (CCI+Veh) or BDNF (CCI+BDNF). Marker expression is quantified by immunofluorescence, as a percentage of the areas of the ipsilateral and contralateral gray matter halves, respectively. (B) depicts the weekly variation of the mechanical nociceptive sensitivity on the paw ipsilateral to CCI after injection with Veh or BDNF, measured in grams of pressure. (C) depicts the weekly variation of the thermal nociceptive sensitivity on the paw ipsilateral to CCI, measured in seconds of withdrawal latency, after injection with Veh or BDNF. (D) depicts the weekly variation of the mechanical nociceptive sensitivity on the paw ipsilateral to CCI, measured in grams of pressure, when the BDNF treatment was delayed for 3 weeks after CCI. (E) depicts the weekly variation of the thermal nociceptive sensitivity on the paw ipsilateral to CCI, measured as seconds of withdrawal latency, when the BDNF treatment was delayed for 3 weeks after CCI.

FIG. 10 depicts the effect of 7,8-dixydroxyflavone (DHF) treatment on the number of spinal cord immature neurons in parallel with its effect on nociceptive sensitivity. (A) depicts the variations in the expression of immature neuron markers Mash1, doublecortin and Notch3 in rat spinal cord ipsilateral and contralateral gray matter halves, 6 weeks after the rats were subjected to CCI and treated with intraperitoneal injections of saline (CCI+Veh) or 7,8-dihydroxyflavone (CCI+DHF). Marker expression is quantified by immunofluorescence, as a percentage of the areas of the ipsilateral and contralateral gray matter halves, respectively. (B) depicts the weekly variation of the mechanical nociceptive sensitivity on the paw ipsilateral to CCI after injection with Veh or DHF, measured in grams of pressure. (C) depicts the weekly variation of the thermal nociceptive sensitivity on the paw ipsilateral to CCI after injection with Veh or DHF, measured in seconds of withdrawal latency. (D) depicts the weekly variation of the mechanical nociceptive sensitivity on the paw ipsilateral to CCI, measured in grams of pressure, when the DHF treatment was delayed for 3 weeks after CCI. (E) depicts the weekly variation of the thermal nociceptive sensitivity on the paw ipsilateral to CCI, measured as seconds of withdrawal latency, when the DHF treatment was delayed for 3 weeks after CCI.

DETAILED DESCRIPTION

In subjects with injuries, disabilities, disorders or diseases, including but not limited to neurological, sensory disorders, psychiatric disorders, diabetes, rheumatism, cancer, and other diseases, alterations in cellular numbers and/or activity can occur. Some of these alterations may involve an increase in the number of adult neural stem cells. During the differentiation process, before becoming mature neurons, the neural stem cells transit a stage of immature neurons, characterized by increased excitability. This invention is based on the idea that, when immature neurons integrate into neuron networks responsible for pain perception and processing, their increased excitability is perceived as pain. Accordingly, by providing subjects suffering from such disorders with a method of treatment that accelerates the neuronal differentiation process and reduces the number of hyper-excitable immature neurons, the symptoms of pain can be alleviated or eliminated. As disclosed for the first time herein, many classes of promoters of neuronal differentiation have a long-term analgesic effect, by reducing the number of immature neurons present in the neural circuits responsible for pain perception and processing.

Another embodiment of the present invention includes the use of promoters of neuronal differentiation in the treatment of pain resulting from incomplete or defective cellular differentiation due to genetic variations. In such patients, a large number of hyper-excitable immature neurons is always present even in the absence of any noticeable injury or disease, contributing to a chronically increased pain sensitivity. As a result of this increased pain sensitivity, the affected individual perceives as painful stimuli which are not normally perceived as painful in a normal individual. Promoters of neuronal differentiation can alleviate or eliminate pain in such cases, for which no alternative treatment exists.

All publications mentioned herein are incorporated by reference to the extent allowed by the law for the purpose of describing and disclosing the proteins, peptides, chemical molecules, vectors, cells and methodologies reported therein that might be used with the present invention. However, nothing herein is to be construed as an admission that the invention is not entitled to antedate such disclosure by virtue of prior invention.

Definitions

This invention is not limited to the methods, protocols, molecules, cell lines, vectors or reagents described herein because they may vary. Furthermore, the terminology used herein is for the purpose of describing particular embodiments only and is not intended to limit the reach of the present invention. Although any materials and methods similar or equivalent to those described herein can be used in the practice of the present invention, representative materials and methods are described herein.

Following patent law convention, the terms "a", "an", and "the" refer to "one or more", e.g. reference to "a compound" includes a plurality of compounds. Unless defined otherwise, all technical and scientific terms used herein have the same meanings as commonly understood by one of ordinary skill in the art in the field of the invention.

Unless otherwise indicated, all numbers expressing quantities of ingredients, conditions, and so forth used in the specification and claims are to be understood as being modified in all instances by the term "about". Accordingly, the numerical parameters set forth in the current specification are approximations that can vary depending on the desired properties sought by the presently disclosed subject matter. Furthermore, Applicants desire that the following terms be given the particular definition as defined below.

The term "agent" shall be construed to include proteins, polypeptides, peptides, chemical molecules and compounds that are capable of promoting or inducing neuronal differentiation, for the purpose of pain treatment.

The term "sequence" shall be construed to include any natural or synthetic amino-acid or nucleotide sequence that maintains, fully or partially, functional similarity with the human molecules indicated herein. Because of the degeneracy of the genetic code, a multitude of nucleotide sequences encoding these proteins, or fragments thereof, may be used. Nucleotide sequences may vary by selecting nucleotide combinations based on possible codon choices, in accordance with standard triplet genetic codes.

The term "sequence homology" shall be construed as meaning the percentage of the amino-acid residues in the candidate sequence that are similar with the residues of a corresponding sequence to which it is compared, after aligning the sequences and introducing gaps if necessary to achieve the maximum percentage identity for the entire sequence. Amino-acid similarity shall be determined according to one of several published physicochemical criteria, selected from the group comprising hydrophobicity, aromaticity, basicity, acidity, and polarity, well known to those of ordinary skill in the art in the field of the invention.

The term "functional similarity" with respect to the amino-acid sequence of a ligand shall be construed to include any natural or synthetic molecule that maintains, fully or partially, the ability to bind to, to activate, or both, specific cellular receptors in a manner similar to its natural ligand, and leading to a similar cellular outcome, including but not limited to neuronal differentiation. Because of the similarity in physicochemical properties between amino-acids, several amino-acids may be used interchangeably for each position in the sequence of a protein to generate alternate sequences that maintain similar function to the natural protein, as commonly understood by one of ordinary skill in the art in the field of the invention. The term shall not be construed to be limited to specific percentage ranges of sequence identity or similarity with the proteins indicated herein, as the introduction of gaps, insertions, substitutions or extensions in an amino-acid or nucleotide sequence may substantially change the percentage of sequence identity or homology, but may maintain the same functionality as the original protein sequence.

The term "neuronal differentiation" shall be construed to represent the process of converting stem cells, neuronal stem cells, immature neurons, or any other type of incompletely differentiated neuron progenitors, into fully functional and physiologically integrated neurons, as commonly understood by one of ordinary skill in the art in the field of the invention. A completely or fully differentiated neuron is a cell that has reached a state characterized by a maximal, final functional role in comparison to the other cells with a similar phenotype present in an organism. For example, a fully differentiated neuron is a cell that expresses a typical set of genes, has a typical electrophysiological response and performs a typical physiological function, usually as part of a cellular network, as understood by those of ordinary skill in the art. The neuronal differentiation activity of a candidate agent (polypeptide, molecule or chemical compound) can be measured in cell culture, in an organism or tissue, by comparing the neuronal differentiation level between cells treated with the candidate agent, cells treated with a known agent inducer of neuronal differentiation (for example BDNF), and cells treated with inactive molecules used as control or reference. The neuronal differentiation level can be determined through any method commonly known to one of ordinary skill in the art in the field of the invention, including but not limited to the measurement of neurite length, electrophysiological recording, immunofluorescence staining of specific markers, cell sorting, gene expression, spectroscopic measurement of bound ligands, radioactive labeling, cell secretion, imaging, organism behavior, etc.

A cell may present various degrees or levels of differentiation, which is a continuous, not a punctual process. For example, progenitor cells display some degree of differentiation relative to stem cells, as progenitor cells can produce by differentiation only a subset of the cells that stem cells can produce. However, progenitor cells maintain the ability to divide into identical daughter cells, similar to stem cells. Immature cells are construed as including cells that are characterized by an incomplete degree of differentiation. In addition, immature cells may display some phenotypical and physiological characteristics similar to the characteristics of un-differentiated cells, some characteristics similar to the characteristics of fully differentiated cells, as well as some unique characteristics that are different from both un-differentiated and fully differentiated cells. For example, immature neurons are neurons that express a subset of the genes typically expressed in neural progenitor cells, as well as some of the genes expressed in fully differentiated neurons, and a set of genes that are expressed neither in neural progenitor cells, nor in fully differentiated neurons. In addition, immature neurons display unique electrophysiological properties, including increased excitability, as commonly known to those of ordinary skill in the art. For example immature neurons produce an electric response when stimulated with the amino acid gamma-aminobutiric acid (GABA), which reflects the presence of GABA receptors and ion channel proteins similar to neurons, however this electric response produced has the opposite sign relative to the electric response produced by fully differentiated or mature neurons.

The term "ligand" as used herein shall be construed to include natural or artificial molecules, including but not limited to proteins, polypeptides, peptides, animal or plant-made molecules or semi-synthetic molecules, which bind, directly or indirectly, to a specific human cellular receptor, selected from the group consisting of: TrkA, TrkB, TrkC, CNTF receptor, GDL family of receptors, Ret receptor, LIF receptor, c-Met receptor, angiotensin receptor, erythropoietin receptor, frizzled (FZD), patched (PTCH), TNF-alpha receptor, and other receptors, and initiate or promote a physiological process, including but not limited to neuronal differentiation. For example, the term "ligand" will also include molecules that bind to a receptor indirectly, by mediation of another molecule or molecules, and promote the physiological function of that receptor through a physico-chemical process selected from a group which includes promoting ligand-receptor binding, post-translational modification of the ligand or receptor, and allosteric modulation of ligand-receptor binding. The term "ligand" will also include antibodies generated against a specific human receptor described herein, and which induce receptor activation. Furthermore, the term "ligand" shall include polypeptides that have 90%-100%, 80%-90%, or 70%-80% homology to a poly-peptide selected from the group consisting of: NGF, BDNF, NT3, NT4, CNTF, GDNF, ARTN, NRTN, PSPN, LIF, angiotensin, erythropoietin, HGF, Wnt, and Hh.

The term "neurotrophin" shall be construed as a protein selected from a group that includes: NGF, BDNF, NT3, and NT4. Neurotrophins bind to, and activate the Trk family of receptor tyrosine kinases, which includes TrkA, TrkB, TrkC and the low-affinity receptor p75trk. Trk receptors activate multiple down-stream signaling pathways, including but not limited to: Ras, PI3-kinase and Ral. Each said pathway can be modulated independently, leading to a variety of biological effects, selected from a group which includes neuronal survival, neuronal differentiation, oncogenesis, neuronal apoptosis, gene regulation, neuronal communication, and many others. Due to the multiple signaling pathways induced by neurotrophins through the activation of Trk receptors, said biological effects can be regulated independently of each other, in conjunction with other additional cellular signals, although some of these biological effects may occur concurrently. For example, neurotrophins may induce at the same time neuronal differentiation and neuronal survival, however these two processes are regulated by different combinations of Trk-dependent pathways, and in conjunction with other, distinct Trk-independent pathways. As a consequence of such differences, neuronal differentiation and neuronal survival are distinct biological processes, and their potential correlation in time does not imply an interdependence with one another.

The terms "promote" and "promotion" used in reference to neuronal differentiation shall be construed as a cellular action selected from the group consisting of: initiation, acceleration, contribution, assistance, induction, and stimulation, of neuronal differentiation.

The terms "promoter" and "inducer" used in reference to neuronal differentiation shall be construed as an agent selected from the group consisting of: a polypeptide, a molecule and a chemical compound, having the property of promoting, inducing, initiating, or accelerating neuronal differentiation. This action can be performed by activating a receptor, a signaling pathway or both, including but not limited to TrkA, TrkB, TrkC, a CNTF receptor, a GDL receptor, a LIF receptor, an angiotensin receptor, an EPO receptor, a FZD receptor, and a SMO receptor.

The term "BDNF" shall be construed as including natural and artificial polypeptides that maintain sequence or functional similarity, or both, to human BDNF, as typically understood by those of ordinary skill in the art, regardless of whether the candidate protein is named "BDNF" or not. Functional similarity to BDNF comprises the ability of an agent to bind to, and activate the TrkB receptor, and to promote neuronal differentiation. While a key receptor binding site is located between amino-acids 173-178 of human BDNF (Obianyo et al., Biochim Biophys Acta 1834:2213-2218 (2013)), other domains of BDNF also contribute to ligand specificity and activity, and will therefore contribute to the activation of the TrkB receptor. Therefore BDNF fragments that retain only some of the functional domains present in full-length BDNF may still activate the TrkB receptor and induce neuronal differentiation. Several natural forms of BDNF exist, generated within the organism by cleavage from the endogenously synthesized full length BDNF precursor. For example, the human precursor BDNF (32 kDa) is a polypeptide 247 amino-acids long. Enzymatic cleavage of precursor BDNF between amino-acids 57-58 generates one form of BDNF (28 kDa) (Mowla et al., J Biol Chem. 276:12660-12666 (2001)). A different cleavage of precursor BDNF between amino-acids 128-129 generates "mature" BDNF (14 kDa) (Seidah et al., J Biol Chem. 379:247-50 (1996)). For example, a polypeptide depicted in the amino-acid sequence "BDNF_FD" (SEQ ID NO:1), located between amino-acids 129-247 of human BDNF precursor, may be used to promote neuronal differentiation for the purpose of pain treatment. This sequence is highly conserved, having 96%-100% homology among animal species, including Homo sapiens, Rattus norvegicus, Mus musculus, Gallus gallus and Xenopus laevis. Many other amino-acid sequences derived from BDNF_FD (SEQ ID NO:1) may be generated, which maintain functional similarity with BDNF and may be used in the treatment of pain. For example, the removal or exchange of 1, 2, 3, 4, 5, 6, 7, 8, 9, 10, or more amino-acid residues from BDNF_FD, may generate polypeptides with functional similarity to BDNF, which may be used in the treatment of pain. In another example, a chemically modified peptide comprising only two amino-acid residues can maintain the ability to activate the TrkB receptor (Obianyo et al., Biochim Biophys Acta 1834:2213-2218 (2013)). These examples indicate that peptides of any length that maintain 90%-100% homology with BDNF_FD may maintain the ability to activate the TrkB receptor even in the absence of some of the functional domains present in BDNF, and therefore may be used in the treatment of pain. For example the polypeptide BDNF_FD1 (SEQ ID NO:28), obtained by removing 2 amino-acids from BDNF_FD, maintains functional similarity with BDNF and may be used for the activation of TrkB and for the treatment of pain. Furthermore, the term "BDNF" shall be construed to also include nucleic acid sequences, including DNA and RNA sequences equivalent to the amino-acid sequence of BDNF_FD or BDNF_FD1. For example a polypeptide having the BDNF_FD sequence can be synthesized using synthetic chemistry or can be generated by a cell in-vitro, or it can be produced within an organism from the equivalent oligonucleotide sequence (cDNA).

The term "NGF" shall be construed as including natural and artificial polypeptides that maintain sequence or functional similarity, or both, to human NGF, as typically understood by those of ordinary skill in the art, regardless of whether the candidate protein is named "NGF" or not. Functional similarity to NGF comprises the ability of an agent to bind to, and activate, fully or partially, the TrkA receptor, and to promote neuronal differentiation. Several natural forms of NGF exist, generated within the organism by cleavage from the endogenously synthesized full length NGF precursor. For example, the human precursor of NGF (pre-proNGF) is a polypeptide 241 amino-acids long. Enzymatic cleavage of precursor NGF between amino-acids 121-122 generates "mature" NGF (beta-NGF, 13.5 kDa) (Seidah et al., Biochem J. 314, 951-960 (1996)). For example, a polypeptide comprising the amino-acid sequence "NGF_FD" (SEQ ID NO:2), located between amino-acids 122-241 of human NGF precursor, may be used to promote neuronal differentiation for the purpose of pain treatment. This sequence is highly conserved, having 92%-100% homology among animal species, including *Homo sapiens, Rattus norvegicus, Mus musculus, Gallus gallus* and *Lipotes vexillifer*. Many other amino-acid sequences derived from NGF_FD may be generated, which maintain functional similarity with NGF and may be used in the treatment of pain. For example, the removal or exchange of 1, 2, 3, 4, 5, 6, 7, 8, 9, 10, or more amino-acid residues from NGF_FD, may generate polypeptides with functional similarity to NGF, which may be used in the treatment of pain. These examples indicate that polypeptides of any length that maintain at least 90% homology with NGF_FD, may also maintain the ability to activate the TrkA receptor, and may be used in the treatment of pain. For example the polypeptide NGF_FD1 (SEQ ID NO:29), obtained by removing 2 N-terminal amino-acids from NGF_FD, maintains all the functional domains present in NGF_FD and may be used for the activation of TrkA and for the treatment of pain. Furthermore, the term "NGF" shall be construed to also include nucleic acid sequences, including DNA and RNA sequences equivalent to the amino-acid sequence of NGF_FD or NGF_FD1.

The term "NT3" shall be construed as including natural and artificial polypeptides that maintain sequence or functional similarity, or both, to human neurotrophin-3 (NT3), as typically understood by those of ordinary skill in the art, regardless of whether the candidate protein is named "NT3" or not. Functional similarity to NT3 comprises the ability of an agent to bind to, and activate, fully or partially, the TrkC or TrkB receptors, and to promote neuronal differentiation. The endogenously synthesized human NT3 (pre-NT3) comprises two precursor protein isoforms 270 and 257 amino-acids long, respectively. Enzymatic cleavage of pre-NT3 (between amino-acids 138-139 in the case of isoform 2) generates "mature" NT3 (Seidah et al., FEBS Lett. 379:247-250 (1996)). For example, a polypeptide comprising the amino-acid sequence "NT3_FD" (SEQ ID NO:3), located between amino-acids 139-257 of human NT3 precursor isoform 2, may be used to promote neuronal differentiation for the purpose of pain treatment. This sequence is highly conserved, having 99%-100% identity among animal species, including *Homo sapiens, Rattus norvegicus, Mus musculus, Gallus gallus* and *Xenopus tropicalis*. Many other polypeptides derived from NT3_FD may be generated, which maintain functional similarity with NT3 and may be used in the treatment of pain. For example, the removal or exchange of 1, 2, 3, 4, 5, 6, 7, 8, 9, 10, or more amino-acid residues from NT3_FD, may generate agents with functional similarity to NT3, which may be used in the treatment of pain. These examples indicate that polypeptides of any length that maintain at least 90% homology with SEQ ID NO:3, may also maintain the ability to activate the TrkC or TrkB receptor, and may be used in the treatment of pain. For example the polypeptide NT3_FD1 (SEQ ID NO:30), obtained by removing 2 N-terminal amino-acid residues from NT3_FD, maintains all the functional domains present in NT3_FD and may be used for the activation of TrkC or TrkB, and for the treatment of pain. Furthermore, the term "NT3" shall be construed to also include nucleic acid sequences, including DNA and RNA sequences equivalent to the amino-acid sequence of NT3_FD or NT3_FD1.

The term "NT4" shall be construed as including natural and artificial polypeptides that maintain sequence or functional similarity, or both, to human neurotrophin-4 (NT4), as typically understood by those of ordinary skill in the art, regardless of whether the candidate protein is named "NT4" or not. Functional similarity to NT4 comprises the ability of an agent to bind to, and to activate, fully or partially, the TrkB receptor, and to promote neuronal differentiation for the purpose of treating pain. The endogenously synthesized human NT4 (pre-NT4) comprises two precursor protein isoforms X1, 220 amino-acids long, and X2, 210 amino-acids long. Enzymatic cleavage of pre-NT4 (between amino-acids 80-81 in the case of isoform X2) generates "mature" NT4, which is considered the biologically active form of NT4. For example, a polypeptide comprising the amino-acid sequence "NT4 FD" (SEQ ID NO:4), located between amino-acids 81-210 of human NT4, may be used to promote neuronal differentiation for the purpose of pain treatment. This sequence is highly conserved, having 98%-100% homology among animal species, including *Homo sapiens, Rattus norvegicus, Mus musculus, Lipotes vexillifer,* and *Sus scrofa*. Many other polypeptides derived from NT4_FD can be generated, which may maintain functional similarity with NT4 and may be used in the treatment of pain. For example, the removal or exchange of 1, 2, 3, 4, 5, 6, 7, 8, 9, 10, or more amino-acid residues from NT4_FD, may generate polypeptides with functional similarity to NT4, which may be used in the treatment of pain. These examples suggest that polypeptides of any length that maintain at least 90% homology with SEQ ID NO:4, may also maintain the ability to activate the TrkB receptor, and may be used in the treatment of pain. For example the polypeptide NT4_FD1 (SEQ ID NO:31), obtained by removing 2 N-terminal amino-acids from NT4_FD, maintains all the functional domains present in NT4_FD and may be used for the activation of TrkB, and for the treatment of pain. Furthermore, the term "NT4" shall be construed to also include nucleic acid sequences, including DNA and RNA sequences equivalent to the amino-acid sequences of NT4_FD or NT4_FD1.

The term "CNTF" shall be construed as including natural and artificial amino-acid sequences that maintain sequence or functional similarity, or both, to human CNTF, as typically understood by those of ordinary skill in the art, regardless of whether the candidate protein is named "CNTF" or not. Functional similarity to CNTF comprises the ability of an agent to bind to, and activate, fully or partially, the CNTF receptor, and to promote neuronal differentiation. For example, a polypeptide comprising the amino-acid sequence "CNTF_FD" (SEQ ID NO:5), located between amino-acids 1-200 of human CNTF, may be used to promote neuronal differentiation for the purpose of treating pain. This sequence is highly conserved, having 93%-100% homology among animal species, including *Homo sapiens, Rattus norvegicus, Mus musculus, Lipotes vexillifer,* and *Sus scrofa*. Many other polypeptides derived from CNTF_FD can be generated, which may maintain functional similarity with CNTF, and may therefore be used in the treatment of pain. For example, the removal or exchange of 1, 2, 3, 4, 5, 6, 7, 8, 9, 10, or more amino-acid residues from CNTF_FD, may generate polypeptides with functional similarity to CNTF, which may be used in the treatment of pain. These examples suggest that polypeptides of any length that maintain at least 90% homology with SEQ ID NO:5, may also maintain the ability to activate the CNTF receptor, and may be used in the treatment of pain. For example the polypeptide CNTF_FD1 (SEQ ID NO:32), obtained by removing 2 amino-acid residues from CNTF_FD, maintains the functional similarity with CNTF and may be used for the activation of the CNTF receptor, and for the treatment of pain. In another example, cintrophin, a polypeptide comprising amino-acid residues 148-161 of human CNTF, maintains functional similarity with CNTF (turn et al., J Neurosci Res. 44:133-41 (1996)). Furthermore, the term "CNTF" shall be construed to also include nucleic acid sequences, including DNA and RNA sequences equivalent to the amino-acid sequences of CNTF_FD or CNTF_FD1.

The term "GDNF" shall be construed as including natural and artificial polypeptides that maintain sequence or functional similarity, or both, to human GDNF, as typically understood by those of ordinary skill in the art, regardless of whether the candidate protein is named "GDNF" or not. Functional similarity to GDNF comprises the ability of an agent to bind to, and activate the GDNF family receptor alpha-1 and the Ret receptor, and to promote neuronal differentiation. Human GDNF comprises at least 5 isoforms, ranging from 159 to 228 amino-acids. For example, a polypeptide comprising the amino-acid sequence "GDNF_FD" (SEQ ID NO:6), located between amino-acids 78-211 of human GDNF precursor isoform 1, may be used to promote neuronal differentiation for the purpose of pain treatment. This sequence is highly conserved, having 95%-100% homology among animal species, including *Homo sapiens, Rattus norvegicus, Mus musculus, Lipotes vexillifer,* and *Canis lupus*. Many other polypeptides derived from GDNF_FD can be generated, which may maintain functional similarity with GDNF, and may therefore be used in the treatment of pain. For example, the removal or exchange of 1, 2, 3, 4, 5, 6, 7, 8, 9, 10, or more amino-acid residues from GDNF_FD, may generate polypeptides with functional similarity to GDNF, which may be used in the treatment of pain. These examples suggest that polypeptides of any length that maintain at least 90% homology with GDNF_FD, may also maintain the ability to activate the GDNF family receptor alpha-1, and may therefore be used in the treatment of pain. For example the polypeptide GDNF_FD1 (SEQ ID NO:33), obtained by removing 2 amino-acid residues from GDNF_FD, maintains functional similarity GDNF and may be used for the activation of the GDNF family receptor alpha-1, and for the treatment of pain. In another example, gliafin, a polypeptide comprising amino-acid residues 153-167 of GDNF, maintains functional similarity with GDNF (turn et al., J Neurosci Res. 44:133-41 (1996)). Furthermore, the term "GDNF" shall be construed to also include nucleic acid sequences, including DNA and RNA sequences equivalent to the amino-acid sequence of GDNF_FD.

The term "ARTN" shall be construed as including natural and artificial polypeptides that maintain sequence or functional similarity, or both, to human ARTN, as typically understood by those of ordinary skill in the art, regardless of whether the candidate protein is named "ARTN" or not. Functional similarity to ARTN shall be construed as the ability of an agent to bind to, and activate the GDNF family receptor alpha-3 and the Ret receptor, and to promote neuronal differentiation. Human ARTN comprises at least 3 isoforms. For example, a polypeptide comprising the amino-acid sequence "ARTN_FD" (SEQ ID NO:7), located between amino-acids 108-220 of human ARTN precursor isoform 1, may be used to promote neuronal differentiation for the purpose of pain treatment. This sequence is highly conserved, having 95%-100% homology among animal species, including *Homo sapiens, Rattus norvegicus, Mus musculus, Lipotes vexillifer,* and *Sus scrofa*. Many other polypeptides derived from ARTN_FD can be generated, which may maintain functional similarity with ARTN, and may therefore be used in the treatment of pain. For example, the removal or exchange of 1, 2, 3, 4, 5, 6, 7, 8, 9, 10, or more amino-acid residues from ARTN_FD, may generate polypeptides with functional similarity to ARTN, which may be used in the treatment of pain. These examples suggest that peptides of any length that maintain at least 90% homology with ARTN_FD, may also maintain the ability to activate the GDNF family receptor alpha-3, and may therefore be used in the treatment of pain. For example the polypeptide ARTN_FD1 (SEQ ID NO:34), obtained by removing 2 amino-acid residues from ARTN_FD, maintains functional similarity with ARTN and may be used for the activation of the GDNF family receptor alpha-3, and for the treatment of pain. Furthermore, the term "ARTN" shall be construed to also include nucleic acid sequences, including DNA and RNA sequences equivalent to the amino-acid sequence of ARTN_FD.

The term "NRTN" shall be construed as including natural and artificial polypeptides that maintain sequence or functional similarity, or both, to human NRTN, as typically understood by those of ordinary skill in the art, regardless of whether the candidate protein is named "NRTN" or not. Functional similarity to NRTN shall be construed as the ability of an agent to bind to, and activate the GDNF family receptor alpha-2 and the Ret receptor, and to induce neuronal differentiation. For example, a polypeptide comprising the amino-acid sequence NRTN_FD (SEQ ID NO:8), located between amino-acids 96-197 of human NRTN, may be used to promote neuronal differentiation for the purpose of pain treatment. This sequence is highly conserved, having 98%-100% homology among animal species, including *Homo sapiens, Rattus norvegicus, Mus musculus, Canis lupus,* and *Tursiops truncatus*. Many other polypeptides derived from NRTN_FD can be generated, which may maintain functional similarity with NRTN, and may therefore be used in the treatment of pain. For example, the removal or exchange of 1, 2, 3, 4, 5, 6, 7, 8, 9, 10, or more amino-acid residues from NRTN_FD, may generate polypeptides with functional similarity to NRTN, which may be used in the treatment of pain. These examples suggest that peptides of any length that maintain at least 90% homology with NRTN_FD, may also maintain the ability to activate the GDNF family receptor alpha-2, and may therefore be used in the treatment of pain. For example the polypeptide NRTN_FD1 (SEQ ID NO:35), obtained by removing 2 amino-acid residues from NRTN_FD, maintains functional similarity with NRTN and may be used for the activation of the GDNF family receptor alpha-2, and for the treatment of pain. Furthermore, the term "NRTN" shall be construed to also include nucleic acid sequences, including DNA and RNA sequences equivalent to the amino-acid sequence of NRTN_FD.

The term "PSPN" shall be construed as including natural and artificial polypeptides that maintain sequence or functional similarity, or both, to human PSPN, as typically understood by those of ordinary skill in the art, regardless of whether the candidate protein is named "PSPN" or not. Functional similarity to PSPN shall be construed as the ability of an agent to bind to, and to activate the GDNF family receptor alpha-4 and the Ret receptor, and to induce neuronal differentiation. For example, a polypeptide comprising the amino-acid sequence "PSPN_FD" (SEQ ID NO:9), located between amino-acids 22-156 of human PSPN, may be used to promote neuronal differentiation for the purpose of pain treatment. This sequence is highly conserved, having 92%-100% homology among animal species, including *Homo sapiens, Rattus norvegicus, Mus musculus, Canis lupus*, and *Sus scrofa*. Many other amino-acid sequences derived from PSPN_FD can be generated, which may maintain functional similarity with PSPN, and may therefore be used in the treatment of pain. For example, the removal or exchange of 1, 2, 3, 4, 5, 6, 7, 8, 9, 10, or more amino-acid residues from PSPN_FD, may generate polypeptides with functional similarity to PSPN, which may be used in the treatment of pain. These examples suggest that peptides of any length that maintain at least 90% homology with PSPN_FD, may also maintain the ability to activate the GDNF family receptor alpha-4, and may therefore be used in the treatment of pain. For example amino-acid sequence PSPN_FD1 (SEQ ID NO:36), obtained by removing 2 amino-acid residues from PSPN_FD, maintains functional similarity with PSPN and may be used for the activation of the GDNF family receptor alpha-4, and for the treatment of pain. Furthermore, the term "PSPN" shall be construed to also include nucleic acid sequences, including DNA and RNA sequences equivalent to the amino-acid sequence of PSPN_FD.

The term "LIF" shall be construed as including natural and artificial polypeptides that maintain sequence or functional similarity, or both, to human LIF functional domains, as typically understood by those of ordinary skill in the art, regardless of whether the candidate protein is named "LIF" or not. Functional similarity to LIF comprises the ability of an agent to bind to, and activate the LIF receptor, and to promote neuronal differentiation. Human LIF comprises at least 2 isoforms. For example, a LIF sequence comprising the amino-acid sequence LIF_FD (SEQ ID NO:10), located between amino-acids 23-202 of human LIF isoform 1, may be used to promote neuronal differentiation for the purpose of treating pain. This sequence is highly conserved, having at least 93% homology among animal species, including *Homo sapiens, Rattus norvegicus, Mus musculus, Lipotes vexillifer*, and *Canis lupus*. Many other amino-acid sequences derived from LIF_FD can be generated, which may maintain functional similarity with LIF, and may therefore be used in the treatment of pain. For example, the removal or exchange of 1, 2, 3, 4, 5, 6, 7, 8, 9, 10, or more amino-acid residues from LIF_FD, may generate amino-acid sequences with functional similarity to LIF, which may be used in the treatment of pain. These examples suggest that polypeptides of any length that maintain at least 90% homology with LIF_FD, may also maintain the ability to activate the LIF receptor, and may therefore be used in the treatment of pain. For example amino-acid sequence LIF_FD1 (SEQ ID NO:37), obtained by removing 2 amino-acid residues from LIF_FD, maintains functional similarity with LIF and may be used for the activation of the LIF receptor, and for the treatment of pain. Furthermore, the term "LIF" shall be construed to also include nucleic acid sequences, including DNA and RNA sequences equivalent to the amino-acid sequence of LIF_FD.

The term "angiotensin" shall be construed as including natural and artificial peptides that maintain sequence similarity to human angiotensin II, as typically understood by those of ordinary skill in the art, regardless of whether the candidate protein is named "angiotensin II" or not. Functional similarity to angiotensin II shall be determined by the ability of an agent to bind to, and activate the angiotensin receptors, and to promote neuronal differentiation. For example angiotensin III and angiotensin IV retain some of the ability of angiotensin II to activate at least some of the angiotensin receptors. In one embodiment, an angiotensin sequence consisting of the amino-acid sequence "ANG" (SEQ ID NO:11), located between amino-acids 34-41 of human angiotensinogen, may be used to promote neuronal differentiation for the purpose of treating pain. This sequence is highly conserved, having at least 95% homology among animal species, including *Homo sapiens, Rattus norvegicus, Mus musculus, Lipotes vexillifer, Gallus gallus* and *Canis lupus*. In another embodiment, other amino-acid sequences derived from ANG can be generated, which may maintain functional similarity with angiotensin, and may therefore be used in the treatment of pain. For example, the removal or exchange of 1, 2, 3, 4, 5, or 6 amino-acid residues from ANG, may generate amino-acid sequences with functional similarity to angiotensin, which may be used in the treatment of pain. For example, angiotensin IV (ANG1, SEQ ID NO:38) retains functional similarity with angiotensin, and may be used in the treatment of pain. These examples suggest that polypeptides of any length that maintain at least 80% homology with ANG, may also maintain the ability to activate the angiotensin receptors, and may therefore be used in the treatment of pain. Furthermore, the term "angiotensin" shall be construed to also include nucleic acid sequences, including DNA and RNA sequences equivalent to the amino-acid sequence of angiotensin.

The term "Wnt" shall be construed as including natural and artificial polypepties that maintain sequence or functional similarity, or both, to any member of human Wnt family of ligands, comprising Wnt1, Wnt2, Wnt2b, Wnt3, Wnt3a, Wnt4, Wnt5a, Wnt5b, Wnt6, Wnt7a, Wnt7b, Wnt8a, Wnt8b and Wnt9a, as typically understood by those of ordinary skill in the art, regardless of whether the candidate protein is named "Wnt" or not. Functional similarity to Wnt shall be construed as the property of an agent to bind to, and activate a FZD receptor, and to promote neuronal differentiation. In one embodiment, a polypeptide selected from the group comprising the amino-acid sequences WNT1_FD (SEQ ID NO:12) comprising amino-acids 28-370 of human Wnt1, WNT2_FD (SEQ ID NO:13) comprising amino-acids 26-360 of human Wnt2, Wnt2b_FD (SEQ ID NO:14) comprising amino-acids 40-391 of human Wnt2b isoform 2, Wnt3_FD (SEQ ID NO:15) comprising amino-acids 22-355 of human Wnt3, Wnt4_FD (SEQ ID NO:16) comprising amino-acids 23-351 of human Wnt4, Wnt5a_FD (SEQ ID NO:17) comprising amino-acids 62-380 of human Wnt5a, Wnt5b_FD (SEQ ID NO:18) comprising amino-acids 18-359 of human Wnt5b, Wnt6_FD (SEQ ID NO:19) comprising amino-acids 25-365 of human Wnt6, Wnt7a_FD (SEQ ID NO:20) comprising amino-acids 32-349 of human Wnt7a, Wnt7b_FD (SEQ ID NO:21) comprising amino-acids 25-349 of human Wnt7b, Wnt8a_FD (SEQ ID NO:22) comprising amino-acids 25-351 of human Wnt8a isoform 3, Wnt8b_FD (SEQ ID NO:23) comprising amino-acids 23-351 of human Wnt8b, and Wnt9a_FD (SEQ ID NO:24) comprising amino-acids 30-365 of human Wnt9a, may be used to promote neuronal differentiation for the purpose of treating pain. Sequences Wnt1_FD, Wnt2_FD, Wnt2b_FD, Wnt3_FD, Wnt4_FD, Wnt5a_FD, Wnt5b_FD, Wnt6_FD, Wnt7a_FD, Wnt7b_FD, Wnt8a_FD, Wnt8b_FD, and Wnt9a_FD are highly conserved, having at least 93% homology among animal species, including Homo sapiens, Rattus norvegicus, Mus musculus, Lipotes vexillifer, and Gallus gallus. In a different embodiment, many other polypeptides derived from a sequence selected from the group consisting of Wnt1_FD, Wnt2_FD, Wnt2b_FD, Wnt3_FD, Wnt4_FD, Wnt5a_FD, Wnt5b_FD, Wnt6_FD, Wnt7a_FD, Wnt7b_FD, Wnt8a_FD, Wnt8b_FD and Wnt9a_FD, can be generated that maintain functional similarity with Wnt. For example, the removal or exchange of 1, 2, 3, 4, 5, 6, 7, 8, 9, 10, or more amino-acid residues from an amino-acid sequence selected from the group consisting of: Wnt1_FD, Wnt2_FD, Wnt2b_FD, Wnt3_FD, Wnt4_FD, Wnt5a_FD, Wnt5b_FD, Wnt6_FD, Wnt7a_FD, Wnt7b_FD, Wnt8a_FD, Wnt8b_FD or Wnt9a_FD, may generate polypeptides with functional similarity to Wnt, which may be used in the treatment of pain. These examples suggest that polypeptides of any length that maintain at least 90% homology with Wnt, may also maintain the ability to activate the frizzled receptors, and may therefore be used in the treatment of pain. For example amino-acid sequences Wnt1_FD1 (SEQ ID NO:39), obtained by removing 2 amino-acid residues from Wnt1_FD, Wnt2_FD1 (SEQ ID NO:40), obtained by removing 2 amino-acid residues from Wnt2_FD, Wnt2b_FD1 (SEQ ID NO:41), obtained by removing 2 amino-acid residues from Wnt2b_FD, Wnt3_FD1 (SEQ ID NO:42), obtained by removing 2 amino-acid residues from Wnt3_FD, Wnt4_FD1 (SEQ ID NO:43), obtained by removing 2 amino-acid residues from Wnt4_FD, Wn5a_FD1 (SEQ ID NO:44), obtained by removing 2 amino-acid residues from Wnt5a_FD, Wnt5b_FD1 (SEQ ID NO:45), obtained by removing 2 amino-acid residues from Wnt5b_FD, Wnt6_FD1 (SEQ ID NO:46), obtained by removing 2 amino-acid residues from Wnt6_FD, Wnt7a_FD1 (SEQ ID NO:47), obtained by removing 2 amino-acid residues from Wnt7a_FD, Wnt7b_FD1 (SEQ ID NO:48), obtained by removing 2 amino-acid residues from Wnt7b_FD, Wnt8a_FD1 (SEQ ID NO:49), obtained by removing 2 amino-acid residues from Wnt8a_FD, Wnt8b_FD1 (SEQ ID NO:50), obtained by removing 2 amino-acid residues from Wnt8b_FD, Wnt9a_FD1 (SEQ ID NO:51), obtained by removing 2 amino-acid residues from Wnt9a_FD, maintain functional similarity with Wnt and may be used for the activation of the FZD receptors, and for the treatment of pain.

In another embodiment, the compound N-Formyl-Met-Asp-Gly-Cys-Glu-Leu (FOXY-5), comprising amino-acids 332-337 of human Wnt5a, maintains functional similarity with Wnt, and may be used in pain treatment. Furthermore, the term "Wnt" shall be construed to also include nucleic acid sequences, including DNA and RNA sequences equivalent to the amino-acid sequence of any Wnt isoform.

The term "Hh" shall be construed to include natural and artificial polypeptides that maintain sequence or functional similarity, or both, to any member of human Hedgehog family of ligands, including Shh, Dhh and Ihh, as typically understood by those of ordinary skill in the art, regardless of whether the candidate protein is named "Hh" or not. Functional similarity to Hh shall be construed as the property of an agent to bind to, and inhibit a Patched (PTCH) receptor, to activate a Smoothened (SMO) receptor, and to promote neuronal differentiation. For example, a polypeptide selected from the group consisting of SHH_FD (SEQ ID NO:25) comprising amino-acids 24-197 of human Shh, DHH_FD (SEQ ID NO:26) comprising amino-acids 23-198 of human Dhh, and IHH_FD (SEQ ID NO:27) comprising amino-acids 28-202 of human Ihh, may be used to promote neuronal differentiation for the purpose of treating pain. These sequences are highly conserved, having at least 95% homology among animal species, including Homo sapiens, Rattus norvegicus, Mus musculus, Lipotes vexillifer, and Gallus gallus. Many other polypeptides derived from SHH_FD, DHH_FD or IHH_FD can be generated, which may maintain functional similarity with Hh, and may therefore be used in the treatment of pain. For example, the removal or exchange of 1, 2, 3, 4, 5, 6, 7, 8, 9, 10, or more amino-acid residues from Shh_FD, Dhh_FD or Ihh_FD, may generate polypeptides with functional similarity to Hh, which may be used in the treatment of pain. These examples suggest that polypeptides of any length that maintain at least 95% homology with Hh, may also maintain the ability to activate a SMO receptor, and may therefore be used in the treatment of pain. For example the polypeptides SHH_FD1 (SEQ ID NO:52), DHH_FD1 (SEQ ID NO:53), and IHH_FD1 (SEQ ID NO:54), obtained by removing 2 amino-acid residues from SHH_FD, DHH_FD, and IHH_FD, respectively, maintain functional similarity to Hh, and may be used to promote neuronal differentiation for the purpose of treating pain. Furthermore, the term "Hh" shall be construed to also include nucleic acid sequences, including DNA and RNA sequences equivalent to the amino-acid sequence of Hh.

The term "TrkA" shall be construed as including proteins that maintain sequence or functional similarity, or both, to the human TrkA receptor, as typically understood by those of ordinary skill in the art. For example the term "TrkA" shall be construed to include all isoforms and variants of the human TrkA protein.

The term "TrkB" shall be construed as including proteins that maintain sequence or functional similarity, or both, to the human TrkB receptor, as typically understood by those of ordinary skill in the art. For example the term "TrkB" shall be construed to include all isoforms and variants of the human TrkB protein.

The term "TrkC" shall be construed as including proteins that maintain sequence or functional similarity, or both, to the human TrkC receptor, as typically understood by those of ordinary skill in the art. For example the term "TrkC" shall be construed to include all isoforms and variants of the human TrkC protein.

The term "CNTF receptor" shall be construed as including proteins that maintain sequence or functional similarity, or both, to the human CNTF receptor, as typically understood by those of ordinary skill in the art. For example the term "CNTF receptor" shall be construed to include all isoforms and variants of the human CNTF receptor.

The term "Ret receptor" shall be construed as including proteins that maintain sequence or functional similarity, or both, to the human Ret receptor, as typically understood by those of ordinary skill in the art. For example the term "Ret receptor" shall be construed to include all isoforms and variants of the human Ret receptor.

The term "GDL receptor" shall be construed as including proteins that maintain sequence or functional similarity, or both, to the human GDNF receptor family, as typically understood by those of ordinary skill in the art. For example the term "GDL receptor" shall be construed to include all isoforms and variants of the human GDNF family receptor alpha-1, human GDNF family receptor alpha-2, human GDNF family receptor alpha-3, and human GDNF family receptor alpha-4.

The term "LIF receptor" shall be construed as including proteins that maintain sequence or functional similarity, or both, to the human LIF receptor alpha, as typically understood by those of ordinary skill in the art. For example the term "LIF receptor" shall be construed to include all isoforms and variants of the human LIF receptor.

The term "erythropoietin receptor" shall be construed as including proteins that maintain sequence or functional similarity, or both, to the human erythropoietin (EPO) receptor, as typically understood by those of ordinary skill in the art. For example the term "erythropoietin receptor" shall be construed to include all isoforms and variants of the human erythropoietin receptor.

The term "c-Met" shall be construed as including proteins that maintain sequence or functional similarity, or both, to the human c-Met receptor, as typically understood by those of ordinary skill in the art. For example the term "c-Met receptor" shall be construed to include all isoforms and variants of the human c-Met receptor.

The term "angiotensin receptor" shall be construed as including proteins that maintain sequence or functional similarity, or both, to the human angiotensin II receptor, as typically understood by those of ordinary skill in the art. For example the term "angiotensin receptor" shall be construed to include human angiotensin receptor type-1, human angiotensin receptor type-1b, human angiotensin receptor type-2, other types of angiotensin receptors, and all their human isoforms and splice variants.

The term "frizzled" shall be construed as including proteins that maintain sequence or functional similarity, or both, to the human frizzled receptor, as typically understood by those of ordinary skill in the art. For example the term "frizzled" shall be construed to include human Frizzled-1, human Frizzled-2, human Frizzled-3, human Frizzled-4, human Frizzled-5, human Frizzled-6, human Frizzled-6, human Frizzled-7, human Frizzled-8, human Frizzled-9, human Frizzled-10, other frizzled domain-containing proteins, and their splice variants in humans.

The term "Patched" shall be construed as including proteins that maintain sequence or functional similarity, or both, to the human Patched-1 receptor (PTCH), as typically understood by those of ordinary skill in the art. For example the term "Patched" shall be construed to include human Patched-1 isoform S, human Patched-1 isoform M, human Patched-1 isoform L, human Patched-1 isoform L', human Patched-2 isoform 1, human Patched 2 isoform 2, other Patched domain-containing proteins, and their splice variants in humans.

The term "Smoothened" shall be construed as including proteins that maintain sequence or functional similarity, or both, to the human Smoothened (SMO) receptor, including its isoforms, as typically understood by those of ordinary skill in the art.

The terms "cell", "cell line" and "cell culture" include progeny. It is understood that all progeny may not be precisely identical in DNA or protein content, due to deliberate or accidental mutations. Variant progeny that have the same function or biological property as determined in the originally characterized cell, are included. The cells used in the present invention are generally eukaryotic or prokaryotic cells.

The term "vector" shall be construed as meaning a DNA or RNA sequence which is functionally linked to a suitable polynucleotide control sequence capable of producing the expression of the DNA in a cell. Such control sequences include a promoter to initiate transcription, an optional operator sequence to control transcription, an origin of replication, a cloning site, selectable markers, a sequence encoding RNA ribosome binding sites, and sequences that control the termination of transcription and translation. The vector may be a plasmid, a phage or virus particle, a cosmid, an artificial chromosome, or a genomic insert. After introduction in a cell, the vector may replicate and function independently of the cell genome, or may in some cases integrate into the genome itself. In the present specification, "vector" and "plasmid" may be used interchangeably, as the plasmid is the most commonly used form of vector. However, the invention is intended to include other forms of vectors which serve equivalent function and which are known in the art.

Alternatively, a vector may include, in addition to the elements described above, an inducible promoter, which activates gene expression only under specific, controllable conditions. Such controllable conditions include a specific temperature (e.g. heat shock promoter), a specific chemical (e.g. doxycycline, dexamethasone, etc.), or other conditions.

The terms "transformation", "transfection" and "infection" shall be construed as meaning the introduction of a vector containing a polynucleotide sequence of interest into a suitable cell, whether or not any coding sequences of that vector are expressed. The cell where the vector is introduced is termed "host cell". The introduced polynucleotide sequence may be from the same species as the host cell, from a different species, or may be a hybrid polynucleotide sequence containing sequences from both the same species and a different species than the host cell. Methods of transfection include electroporation, calcium phosphate, liposome, DEAE-dextran, microinjection, polybrene, and others. The term "infection" shall be construed as meaning a transfection by use of a viral vector. Examples of viral vectors include adenovirus (AV), adeno-associated virus (AAV), lentivirus (LV), herpes simplex virus (HSV), simian immunodeficiency virus (SIV), human immunodeficiency virus (HIV) and others.

In addition to the above definition, the term "transfection" shall be construed to also include the introduction of a protein into a host cell. Protein transfection may be achieved using a variety of commercially available reagents and kits, e.g. cationic lipid mixtures, peptides, etc.

The term "stem cell" shall be construed as including cells that maintain the ability to become any type of cell that is present in an organism. Examples of stem cells include embryonic stem cells, mesenchymal stem cells, amniotic stem cells, dental pulp stem cells, induced pluripotent stem cells (iPSCs), and others. The term "progenitor cell" is construed as including cells that maintain the capability of becoming a subset of all the cell types present in an organism. For example, a neural progenitor cell is a progenitor cell that can become one of several types of cells present in the nervous system. In the present specification, "stem cell" and "progenitor cell" may be used interchangeably, as the progenitor cell is a type of stem cell that has acquired some individual characteristics that differentiate it from a stem cell. For example, a neural progenitor cell may express a partially different subset of genes than a stem cell, which limit the ability of the neural progenitor cell to become only a cell type present in the nervous system. However, it is understood that both stem cells and progenitor cells are continuously dividing cells, and produce through division daughter cells identical to the dividing parent cell, over a large number of divisions. Alternatively, cells with stem cell properties may be derived from natural sources (e.g. cancer cells).

The term "pain" shall be construed to include the perception of pain, as commonly understood in medical practice and/or human communication. Pain symptoms may include acute or chronic pain, following an injury, neurodegenerative disease, cancer, diabetes, rheumatism, genetic variation, pain of unknown origin, etc. The pain threshold is a minimum value of the stimulus at which the stimulation is perceived as pain. The pain threshold does not have a specific value, and may vary in different people, or in the same person at different times. Stimuli that are considered normal for the average individual may become abnormal and cross above the pain threshold in specific individuals, or in the average individual under specific conditions. Pain sensitivity varies inversely to the pain threshold, for example a higher pain threshold is equivalent to a lower pain sensitivity.

The terms "pain level" and "pain intensity" shall be construed to represent a numerical or symbolic value assigned to pain through a measurement or evaluation method selected from a group which includes, but is not limited to a Wong-Baker FACES pain rating scale, a numeric pain rating scale, a pain quality assessment scale, a multi-dimensional pain questionnaire, a verbal descriptor scale, a visual analogue scale, the FLACC scale, the CRIES scale, the COMFORT scale, an MRI scan, a heart rate measurement, an electrocardiogram scan, a dolorimeter, an algesiometer, a von Frey filament scale, a measurement of withdrawal latency (in seconds) from radiant heat (Hargreaves method, the tail flick test, the tail withdrawal test, the hot plate test), ultrasound, lasers, etc. A multitude of subjective evaluations, physiological measurements, or combinations thereof can be used to determine pain level and variations thereof.

The term "pain sensitivity" shall be construed to represent the ability of a subject to perceive pain. Some subjects may perceive as painful stimuli which are not normally perceived as painful in an average subject. Such increase in pain sensitivity may be the result of an injury, disease, disorder, or genetic condition. Pain sensitivity varies inversely to the pain threshold.

The term "nociception" shall be construed to include the response of sensory neurons to external stimuli, including mechanical, thermal, and chemical stimuli, and the transmission of said response to the spinal cord. Because nociception typically results in a perception of pain, herein the terms "pain" and "nociception" are used interchangeably.

The term "flavone" shall be construed to represent the compound known as 2-phenylchromen-4-one (2-phenyl-1-benzopyran-4-one) under IUPAC rules.

The description of a new mechanism of pain

A new model of pain regulation is described, wherein pain is determined by the number of hyper-excitable immature neurons present in the spinal cord dorsal horns (Rusanescu et al., J Cell Mol Med. 19:2352-2364 (2015)). According to this model, an increase in the number of spinal cord dorsal horn immature neurons results in an increased pain and pain sensitivity, whereas a reduction of the number of spinal cord dorsal horn immature neurons results in a reduction of pain and pain sensitivity.

Spinal nerve injury is typically followed by a period of 2-3 months of chronic pain. In experimental animals subjected to unilateral chronic constriction injury of the sciatic nerve (CCI), this extended period of pain has been considered to be similar to human cases of chronic pain (Bennett et al., Pain 33, 87-107 (1988)), and the CCI method is therefore used in an experimental setting to simulate human pain.

In experimental mice and rats, CCI leads to an induction of adult neurogenesis (Rusanescu et al., J Cell Mol Med. 19, 2352-2364 (2015)). FIG. 1 depicts the increase in EdU staining, specific for proliferating cells, measured by immunofluorescence and quantified in the spinal cord ipsilateral to CCI, four weeks after CCI. Since EdU stains non-specifically all proliferating cells, a neuron-specific marker, nestin, is depicted in FIG. 2 as having a similar variation in time and ipsilateral location with EdU. Nestin is a marker specific for neural stem cells (Schechter et al., Stem Cells 25, 2277-2282 (2007)). The largest increase in nestin expression is reached only 6 weeks after CCI. The delayed increase in EdU and nestin staining, explained by the limited rate of adult neurogenesis, and by the time necessary for these neuron progenitors to migrate to the dorsal horn, is essential for the understanding of the extended symptoms of chronic pain.

Subsequent to nestin expression, the process of neuronal differentiation continues in neuron progenitor cells by transiting sequential stages of neuronal differentiation characterized by the expression of Mash1 (Bertrand et al., Nat Rev Neurosci. 3:517-30 (2002)), doublecortin (Brown et al., J Comp Neurol. 467:1-10 (2003)) and Notch3 (Rusanescu et al., J Cell Mol Med. 18:2103-2016 (2014)). FIG. 3, FIG. 4 and FIG. 5 show the gradual increase in Mash1, doublecortin and Notch3 expression, respectively, over six weeks after CCI. The increases in Mash1, doublecortin and Notch3 expression are significantly larger on the side ipsilateral to the injured nerve, indicating the increased presence of immature neurons.

The presence of neuron progenitor cells in the spinal cord has been demonstrated before, however the complete differentiation of said cells into mature functional neurons, which are integrated into spinal cord circuits, has never been demonstrated. FIG. 6 depicts a 21% increase in the number of neurons in the ipsilateral spinal cord dorsal horn layers I and II, relative to the contralateral side, six weeks after CCI. This excess of neurons on the ipsilateral side can be observed for up to 4 months after CCI (Rusanescu et al., J Cell Mol Med. 19:2352-2364 (20015)), which indicates that these neurons are integrated into the spinal cord circuits, otherwise these neurons would be unable to survive for several months. The integration of these newly generated neurons while in an immature and hyper-excitable state, into spinal cord neuronal circuits that process pain signals results in increased spinal cord excitability and a chronic perception of pain for as long as said neurons are in an immature state. In the case of CCI, the presence of immature neurons can last for several months, until such neurons mature and become less excitable. In the case of genetic conditions which prevent neuronal maturation (Rusanescu et al., J Cell Mol Med. 18:2103-2016 (2014)), or which constantly generate new immature neurons, increased spinal cord excitability and pain can be life-long conditions.

The representation of the minimal mechanical stimulus capable of inflicting pain after CCI (mechanical threshold) versus time on a semi-log graph (FIG. 7, A) demonstrates the presence of at least two distinct mechanisms responsible for pain. The arrows in FIG. 7 indicate an inflexion point at weeks 4-5, which indicates a change in the mechanism of pain. The early phase of pain (weeks 1-4) was due to an inflammatory mechanism triggered by the immune system (Ren et al., Nat Med. 16:1267-76 (2010)). By week 4 after CCI, the gliosis associated with the inflammatory response decreased to control levels (Rusanescu et al., J Cell Mol Med. 19:2352-2364 (20015)), indicating that inflammation is not a cause for pain after week 4. During weeks 4-8, equivalent to chronic (long-term) pain, the main cause of pain is the increase in the number of spinal cord immature neurons, as depicted in FIGS. 1-6. FIG. 7 (B) depicts the variation in sensitivity to heat-induced pain, which shows a similar inflexion point at week 4. The response to mechanical stimuli on the contralateral paw depicted in FIG. 7 (C) was less intense and the inflexion point was shifted to week 5, which reflects the smaller number of immature neurons that reach the contralateral spinal cord. The response to radiant heat on the contralateral paw depicted in FIG. 7 (D) was similar to Sham animals.

The idea that the immature neurons generated by adult neurogenesis contribute to pain was tested by demonstrating the effects of artificially increasing or decreasing neurogenesis on pain sensitivity (Rusanescu et al., J Cell Mol Med. 19:2352-2364 (20015)). The level of neurogenesis is regulated by EGF and FGF2 concentrations (Vescovi et al., Neuron 11:951-66 (1993)). FIG. 8 (A) depicts the changes in the expression of neuron progenitor markers Mash1, doublecortin and Notch3 after CCI, when experimental rats are treated with intrathecal injections of either control saline (CCI+Veh), or inhibitors of EGF and FGF2 signaling (CCI+INH), or EGF and FGF2 active growth factors (CCI+GF). All three markers undergo an increase after GF treatment and a decrease after treatment with inhibitors of EGF and FGF2 (INH). FIG. 8 (B-E) depicts changes in pain sensitivity occurring after the same treatments as in (A). FIG. 8 (B) depicts a decrease in mechanical pain sensitivity after treatment with INH, both in CCI-treated rats and in control rats. FIG. 8 (C) depicts a decrease in thermal pain sensitivity, after treatment with INH. FIG. 8 (D) depicts an increase in mechanical pain after treatment with GF. FIG. 8 (E) depicts an increase in thermal pain sensitivity after treatment with GF. Overall, FIG. 8 indicates that there is a strong correlation between the number of spinal cord immature neurons and the level of pain sensitivity.

A Method of Using Promoters of Neuronal Differentiation for the Purpose of Reducing Pain A reduction of the number of spinal cord dorsal horn immature neurons, for the purpose of reducing pain, is achieved by treatment with a compound that induces or promotes the differentiation of highly excitable immature neurons into mature neurons with low excitability. Many of the mature neurons generated through said treatment may be inhibitory neurons, which may contribute to the overall effect of reducing pain.

Any type of compound that promotes neuronal differentiation may be used in the treatment of pain. This invention describes the use of protein families having the well-established property of inducing neuronal differentiation by binding to, and activating a specific receptor, as typically understood by those of ordinary skill in the art in the field of the invention. This invention also describes the use of other compounds which are effective in treating pain by inducing neuronal differentiation. These molecules typically induce neuronal differentiation by binding to a specific receptor and activating down-stream signaling pathways and the transcription of neuron-specific genes in a manner similar to the natural ligands.

The specific receptors described herein that have the ability to induce neuronal differentiation, and therefore may be targeted by ligands intended to treat pain, include but are not limited to, TrkA, TrkB, TrkC, CNTF, GDNF family receptor alpha-1, GDNF family receptor alpha-2, GDNF family receptor alpha-3, GDNF family receptor alpha-4, Ret, LIF receptor, c-Met, angiotensin receptor, erythropoietin receptor, FZD, PTCH, and SMO. It is understood that some of these receptors use co-receptors to perform some or all of their physiological functions. This list is included as an example, and is not intended to limit the applicability and range of this invention, as other receptors or cell signaling pathways may also directly or indirectly promote neuronal differentiation and may therefore be used in treating pain.

The activation of the TrkB receptor induces a long-term reduction in pain and pain sensitivity, contrary to existing concepts known to those of ordinary skill in the art in the field of the invention. The activation of the TrkB receptor can be achieved using an agent (ligand) selected from a group comprising BDNF, and other TrkB ligands. For example, BDNF treatment of an animal subjected to CCI results in a long-term reduction of pain in treated animals (FIG. 9). The reduction in the expression of Mash1, DCX and Notch3 after BDNF treatment (FIG. 9, A) correlates with the reduction in mechanical pain susceptibility (increased pain threshold), depicted in FIG. 9 (B). The similarity of BDNF effects in CCI-treated and Sham-treated animals is an indication that BDNF reduces pain by inducing the differentiation of immature neurons, which are present in both CCI and Sham-treated animals. Said similarity between CCI and Sham-treated animals is an indication that the action of BDNF is not mediated through alternative mechanisms for pain, such as preventing neuronal death or reducing inflammation, because these processes are absent in Sham or control animals. BDNF treatment may increase long-term sensitivity to thermal pain by reducing the number of inhibitory neurons generated in the spinal cord (FIG. 9,C). The introduction of a 3-week delay in the administration of BDNF treatment after CCI allows the initial production of a large number of neuron precursor cells (depicted in FIGS. 1-5). BDNF administration induces a short-term, brief increase in pain, followed by a long-term reduction in pain and pain susceptibility (FIG. 9 (D)). A delayed BDNF treatment also reduced thermal pain susceptibility (FIG. 9 (E)), by increasing the number of inhibitory neurons in the spinal cord.

In a different embodiment, agents that activate the TrkB receptors also include chemical compounds (Obianyo et al., Biochim Biophys Acta 1834:2213-2218 (2013)). Some TrkB ligands have a flavone structure, for example the 7,8-dihidroxyflavone (DHF) (Jang et al., Proc Natl Acad Sci USA. 107: 2687-92 (2010)). FIG. 10 depicts the effects of DHF administration on neuronal differentiation and pain, which are very similar to the effects of BDNF. DHF promotes the differentiation of immature neurons and reduces the expression of Mash1, DCX and Notch3 (FIG. 10, A). Concurrently, DHF also reduces long-term mechanical pain susceptibility (FIG. 10, B), but not thermal pain susceptibility (FIG. 10, C). A 3-week delay in DHF administration after CCI produces a brief short-term increase, followed by an extended long-term decrease in mechanical and thermal pain susceptibility (FIG. 10, D,E), similar to BDNF. The similarity between the effects of DHF and the effects of BDNF on pain levels is an indication that DHF and BDNF act through the same cellular mechanism, by activating the TrkB receptors and inducing neuronal differentiation, but not through other mechanisms proposed in the scientific literature in the field of the invention.

In another embodiment, many other natural and synthetic agents with the property of activating TrkB are known, which may be used in treating pain. These include, but are not limited to: deoxygedunin, dihydro-deoxygedunin, alpha-dihydrogedunol (Jang et al., PLOS One 5:e11528 (2010)), 7,8,3'-trihydroxyflavone (Yu et al., Biochem Biophys Res Comm. 422:387-92 (2012)), 7,8,2'-trihydroxyflavone, 7,8,3'-tridydroxyflavone, 5,7,8-trihydroxyflavone, 7,3'-dihydroxyflavone, 5,7,8,2'-tetrahydroxyflavone, 3,7-dihydroxyflavone, 4'-dimethylamino-7,8-dihydroxyflavone, 4'-dimethylamino-8-hydroxy-7-methoxyflavone (Liu et al., J Med Chem. 53:8274-86 (2010)), N-acetyl-serotonin, N-[2-(5-hydroxy-1H-indol-3-yl)ethyl]-2-oxopiperidine-3-carboxamide (Shen et al., Proc Natl Acad Sci USA. 109:3540-45 (2012)), 5-oxo-L-prolil-L-histidyl-L-tryptophan-methyl ester (LM22A-1), 2-[2,7-bis[[(2-hydroxyethyl)amino]sulfonyl]-9H-fluoren-9-ylidene]-hydrazinecarboxamide (LM22A-2), N-[4-[2'[5-amino-4-cyano-1-(2-hydroxyethyl)-1H-pyrazol-3-yl]-2-cyanoethenyl]phenyl]-acetamide (LM22A-3), and N,N',N''-tris(2-hydroxyethyl)-1,3,5-benzenetricarboxamide (LM22A-4) (Massa et al., J Clin Invest. 120:1774-85 (2010)). Many other compounds derived by substitution from flavone, flavanone (2,3-dihydroflavone; 2-phenyl-4-chromanone), flavanonol (3-hydroxy-2,3-dihydro-2-phenylchromen-4-one, 3-hydroxyflavanone), flavanol (2-phenyl-3,4-dihydro-2H-chromen-3-ol), or chalcone (1,3-diphenyl-1-propen-3-one) may have the ability to activate the TrkB receptor and induce neuronal differentiation, and may therefore be used to treat pain.

In another embodiment, many other natural or synthetic compounds are known, or may be derived through chemical reactions from known compounds, which may have the ability to activate TrkB, directly or indirectly, and which as a result may be used in promoting neuronal differentiation and in treating pain.

In addition to polypeptides identical or similar to NGF, other agents with the property of activating TrkA are known, which may be used in treating pain. These include, but are not limited to gambogic amide. In addition to these examples, many other natural or synthetic compounds are known, or may be derived through chemical reactions from known compounds, which may have the ability to activate TrkA, directly or indirectly, and which as a result may be used in promoting neuronal differentiation and in treating pain.

In addition to polypeptides identical or similar to NT3, other natural or synthetic compounds are known, or may be derived through chemical reactions from known compounds, which may have the ability to activate TrkC, directly or indirectly, and which may as a result be used in promoting neuronal differentiation and in treating pain.

In addition to polypeptides identical or similar to CNTF, other natural or synthetic compounds are known, or may be derived through chemical reactions from known compounds, which may have the ability to activate the CNTF receptor, directly or indirectly, and which may be used in promoting neuronal differentiation and in treating pain.

In addition to polypeptides identical or similar to GDL, other natural or synthetic compounds are known, or may be derived through chemical reactions from known compounds, which may have the ability to activate Ret, directly or indirectly, and which may be used in promoting neuronal differentiation and in treating pain.

In addition to polypeptides identical or similar to LIF, other natural or synthetic compounds are known, or may be derived through chemical reactions from known compounds, which may have the ability to activate the LIF receptor, directly or indirectly, and which may be used in promoting neuronal differentiation and in treating pain.

In addition to polypeptides identical or similar to angiotensin, other agents with the property of being ligands for the angiotensin receptors are known, which may be used in treating pain. For example, 5,7-dimethyl-2-ethyl-3-[[4-[2 (N-butyloxycarbonyl sulfonamido)-5-isobutyl-3-thienyl] phenyl]methyl]imidazo[4,5-b]-pyridine (L-162, 313) is a ligand for the angiotensin receptor type-1, and N(alpha)-nicotinoyl-Tyr-(N(alpha)-carboxybenzoyl-arginine)-Lys-His-Pro-Ile (GCP-42112A) is a ligand for angiotensin receptor type-2.

In addition to polypeptides identical or similar to EPO, other natural or synthetic compounds are known, or may be derived through chemical reactions from known compounds, which may have the ability to activate EPO receptors, directly or indirectly, and which may be used in promoting neuronal differentiation and in treating pain. For example, Epotris, a polypeptide comprising amino-acids 92-111 of human EPO, can induce neurite growth (Pankratova et al., Brain 133:2281-94 (2010)), which suggests that it may be used in treating pain.

In addition to polypeptides identical or similar to HGF, other natural or synthetic compounds are known, or may be derived through chemical reactions from known compounds, which may have the ability to activate c-Met receptors, directly or indirectly, and which may be used in promoting neuronal differentiation and in treating pain. For example, N-hexanoic-Tyr-Ile-(6)aminohexanoic amide (Dihexa) is a compound that binds to HGF and potentiates its ligand activity, inducing neuronal differentiation, and may therefore be used in treating pain.

In addition to polypeptides identical or similar to Hh, other agents with the ability to activate the SMO receptor and the Hh signaling pathway are known, which may be used in treating pain. For example, N-methyl-N'-(3-pyridinylbenzyl)-N'-(3-chlorobenzo[b]thiophene-2-carbonyl)-1,4-diaminocyclohehane (SAG) (Bragina et al., Neurosci Lett. 482:81-5 (2010)), and 2-(1-naphthoxy-6-(4-morpholinoanilino)-9-cyclohexylpurine (Wu et al., Chem Biol. 11:1229-1238 (2004)) are ligands for SMO, activate the Hh pathway and may promote neuronal differentiation, therefore may be used in the treatment of pain. In addition to these examples, many other natural or synthetic compounds are known, or may be derived through chemical reactions from known compounds, which may have the ability to activate SMO directly or indirectly, and which may be used in promoting neuronal differentiation and in treating pain.

In addition to polypeptides identical or similar to Wnt, other natural or synthetic compounds are known, or may be derived through chemical reactions from known compounds, which may have the ability to activate FZD receptors, directly or indirectly, and which may be used in promoting neuronal differentiation and in treating pain.

A limited number of individual flavones have been empirically known to have analgesic effects, which include flavone (Thirugnanasambantham et al., Clin Exp Pharmacol Physiol. 20:59-63 (1993)), procyanidin, rutin, hyperoside (Rylski et al., Acta Physiol Pol. 30:385-8 (1979)), isoliquiritigenin (Shi et al., Phytother Res. 26:1410-7 (2012)), gossypin (Viswanathan et al., Eur J Pharmacol. 98:289-91 (1984)), 3,3'-dihydroxyflavone, 5,6-dihydroxyflavone, 3,7-dihydroxyflavone, 6,3'-dihydroxyflavone (Vidyalakshmi et al., Pharmacol Biochem Behav. 96:1-6 (2010)), 7,2'-dimethoxy flavone, 7,3'-dimethoxyflavone, 7,4'-dimethoxyflavone, 7,8-dimethoxy flavone (Pandurangan et al., Eur J Pharmacol. 727:148-57 (2014)), 0-(beta-hydroxyethyl rutoside (Ramaswamy et al., Indian J Exp Biol. 23:219-20 (1985)), 5-hydroxyflavone, 7-hydroxyflavone, 2'-hydroxyflavone, 5,7-dihydroxyflavone (Thirugnanasambantham et al., J Ethnopharmacol. 28:207-14 (1990)), 3,6-dihydroxyflavone, 3,2'-dihydroxyflavone, 3,4'-dihydroxyflavone, 6,7- dihydroxyflavone, 3',4'-dihydroxyflavone, 7,2'-dihydroxyflavone (Girija et al., Indian J Exp Biol. 40:1314-6 (2002)), myricetin, myricitrin, linarin, baicalin, baicalein, luteolin, hesperidin, and wogonin. The analgesic action of said flavones has been thought to occur by activating opioid or GABA receptors (Viswanathan et al., Eur J Pharmacol. 98:289-91 (1984); Girija et al., Indian J Exp Biol. 40:1314-6 (2002)), through anti-inflammatory action (Burnett et al., J Med Food. 10:442-451 (2007), or through the modulation of ion channels (Hagenacker et al., Eur J Pain. 14:992-8 (2010)). These actions activate cellular mechanisms that are distinct from the activation of TrkB and the induction of neuronal differentiation. The ability of said compounds to induce TrkB activation and neuronal differentiation in relation with their analgesic properties was not tested, therefore said compounds do not constitute prior art for the purpose of identifying new related compounds with analgesic properties based on their neuronal differentiation ability. In fact, until the date of this application, TrkB agonists have been universally considered to have the opposite effect, of promoting pain.

Methods for Screening and Identifying Compounds which can Reduce Pain

The idea of this invention, that agents with the ability to promote neuronal differentiation can also reduce pain, can be used to screen for, and identify new candidate treatments for pain. Because immature neurons contribute to the perception of pain, new candidate agents for treating pain may be identified by screening libraries of chemical compounds for the ability to induce neuronal differentiation. Many methods for testing the ability of a compound to induce neuronal differentiation may be used, which are well-known to those of ordinary skill in the art in the field of the invention. Examples of screening methods include, but are not limited to: the measurement of neurite growth, immunofluorescence measurement of neuronal marker expression, binding of labeled ligands to neuron-specific receptors, secretion of neuron-specific molecules, changes in cell morphology, and other methods.

Chemical compounds identified as candidate agents for pain treatment by screening for neuronal differentiation may be further tested in animals, developed by chemical modification to generate other candidate compounds, or developed by pharmacological formulation for various routes of administration.

Pharmaceutical Formulation

Therapeutic formulations of the agents described herein as promoters of neuronal differentiation may be prepared for the purpose of administration to an individual as injections, perfusions, patches, by mouth (tablets, capsules, solutions, suspensions), by inhalation, by nanoparticles, by infusion pumps, as viral particles or as cell transplants.

Therapeutic formulations of the agents described herein as promoters of neuronal differentiation may be prepared for storage or administration as lyophilized formulations, aqueous solutions, powders, tablets, capsules, or plasmids, by mixing the purified agent with optional carriers, excipients or stabilizers commonly used in the art, all of which are termed "excipients". Excipients include buffers, stabilizing agents, anti-oxidants, preservatives, detergents, salts, and other additives. Such additives must be nontoxic to cells or recipients at the dosages and concentrations used.

In another embodiment, therapeutic formulations may include cells or viruses modified to express the polypeptides described herein as promoters of neuronal differentiation.

Buffering agents maintain the pH of the agent formulation in a range which approximates physiological conditions. Suitable buffering agents for use with the current invention include organic and inorganic acids and salts thereof, such as citrate buffers (e.g. monosodium citrate-disodium citrate mixture, citric acid-trisodium citrate mixture, etc.), succinate buffers (e.g. succinic acid-monosodium succinate mixture, succinic acid-sodium hydroxide mixture, etc.), fumarate buffers (e.g. fumaric acid-sodium hydroxide mixture, fumaric acid-disodium fumarate mixture, etc.), gluconate buffers (e.g. gluconic acid-sodium gluconate mixture, gluconic acid-sodium hydroxide mixture, etc.), acetate buffers (e.g. acetic acid-sodium acetate mixture, acetic acid-sodium hydroxide mixture, etc.), phosphate buffers (e.g. monosodium phosphate-disodium phosphate mixture, etc.), trimethylamine salts (e.g. Tris), and other buffers.

Preservatives may be used to inhibit microbial growth in the formulation. Suitable preservatives for use with the current invention include phenol, benzyl alcohol, meta-cresol, methyl paraben, propyl paraben, benzalkonium halides, catechol, resorcinol, cyclohexanol, and others typically used in the art.

Stabilizers may be used to increase solubility, provide isotonicity, prevent denaturation, or prevent adherence to container of the agent. Suitable stabilizers for use with the current invention include polyhydric alcohols and sugars (e.g. glycerin, polyethylene-glycol, erythritol, xylitol, mannitol, sorbitol, inositol, trehalose, lactose, etc.), amino-acids (e.g. arginine, glycine, histidine, polypeptides, etc.), proteins (e.g. albumin, gelatin, etc), reducing agents (e.g. urea, glutathione, thioglycerol, sodium thioglycolate, sodium thiosulfate, etc.), and others commonly used in the art.

Detergents may be used to increase solubility and prevent aggregation of the formulation. Suitable detergents for use with the current invention include polysorbates (e.g. 20, 80, etc.), polyoxyethylene sorbitan ethers (TWEEN-20, TWEEN-80), polyoxamers and others commonly used in the art.

The formulations for in-vivo use must be sterile. This can be achieved by filtration through sterile filtration membranes.

Articles of Manufacture

In another embodiment of the invention, an article of manufacture is provided, containing materials useful for the treatment of pain, as described in the invention. The article of manufacture comprises a label and a container. Suitable containers include vials, bottles, syringes, and test tubes. The containers may be formed from a variety of materials, such as glass or plastic. The container holds a composition which is effective in treating pain or in modifying cells used to treat pain. The active component in the composition is the agent, in the form of a polypeptide, chemical compound or vector. The label attached to the container indicates that the composition is used to treat pain. The article of manufacture may further include a second container comprising a pharmaceutically acceptable buffer, such as phosphate-buffered saline, dextrose solution or Ringer's solution. The article of manufacture may further include a third container comprising a pharmaceutically acceptable cell transfection system (e.g. liposomes, etc.). The article of manufacture may further include other materials necessary for the user, including other buffers, antibiotics, filters, syringes, and instructions for use.

Therapeutic uses of agents that promote neuronal differentiation

It is intended that the agents described in the current invention may be used to treat a human or an animal. In one embodiment, the agent may be administered to a human or to an animal to treat pain. The present invention is directed to promote the differentiation of neurons in order to reduce their excitability and to reduce pain and pain sensitivity.

In another embodiment, the agent may be administered to treat chronic pain, that lasts for more than 3 months.

In another embodiment, the agent may be administered to treat medium term pain, that lasts between 3 weeks-3 months.

In another embodiment, the agent may be administered directly to the spinal cord as an epidural or intradural (intrathecal, spinal) injection. The injection may be repeated as needed, or may be administered by catheter, infusion pump, or both, over a period of time.

In another embodiment, the agent may be administered by mouth in the form of tablets, capsules, solutions or suspensions, until the elimination of pain is achieved, usually over a period of 3-5 weeks.

In another embodiment, if no pain symptom improvement is achieved within 2 weeks, the agent may be replaced with another agent with ligand properties for a different receptor family, as disclosed herein. Alternatively, two or more agents acting as ligands on different receptor families described herein may be administered simultaneously to treat pain.

The administration route for the agent shall be selected with the purpose of obtaining the optimal therapeutic concentration for the optimal period of time adequate for each individual. Concentration increases over the optimal therapeutic dose and duration shall be avoided in order to prevent adverse effects.

In another embodiment, proliferating host cells, including stem cells or progenitor cells, may be extracted from the same individual (autologous), or from another individual of the same species, or from a different species (heterologous). The agent may be introduced in these host cells, or in artificially modified cell lines, in the form of a polynucleotide (cDNA) that has the ability to generate the agent in the form of a polypeptide by transcription in-vivo, inside the host cell. The host cells that express the agent polypeptide may be introduced back into the same or into a different human host by transplantation, where the host cells are intended to secrete the polypeptide for therapeutic purposes.

In another embodiment, the transcription of the polynucleotide that has the ability to generate the agent in the form of a polypeptide may be placed under the control of an inducible promoter, for example containing TetO. Such promoters may be subjected to repeated cycles of induction and inhibition, as needed for pain treatment.

In cases where host cells expressing the agent are transplanted into a receiving individual different from the original individual donor of the host cells, the receiving individual may be administered immune suppression therapy in order to avoid the rejection of transplanted cells or tissues.

In a different embodiment, the nucleic acid sequence that expresses the agent may be administered in the form of a viral vector, or in other forms of gene therapy, to cells in a human for the purpose of becoming intracellular, expressing the agent and inducing neuronal differentiation. For example, vectors expressing BDNF polynucleotide may be introduced in the spinal cord in order to promote the differentiation of neuron progenitors and immature neurons. Viral vectors that may be used for agent polynucleotide delivery to cells inside a human include adenoviruses, adeno-associated viruses, retroviruses, and other types of viruses. Transfecting agents, encapsulation in liposomes, microparticles, nanoparticles, microcapsules, or administration in linkage to a ligand subject to receptor-mediated endocytosis may be also used to introduce agent nucleic acid sequences into cells, inside or outside a human. Alternatively, nucleic acid-ligand complexes can be formed, in which the ligand comprises a fusogenic peptide to disrupt endosomes, allowing the nucleic acid to avoid lysosomal degradation. Alternatively, the nucleic acid may be targeted for in vivo cell specific uptake and expression, by targeting a specific receptor.

In a different embodiment, the host cells may be stimulated to produce their own agent, for the purpose of inducing neuronal differentiation. This procedure may be done using inducers of transcription specific for each agent, or by inducing agent-specific proteases which cleave the precursor protein into the biologically active "mature" polypeptide agent. This procedure may be performed on cells in cell culture or directly in cells inside a human.

In a different embodiment, cells induced to express the agent, whether by introducing a vector containing a polynucleotide that expresses the agent, or by directly introducing the agent polypeptide, may be introduced in an experimental animal for pre-clinical studies designed to develop a treatment for a disease or disorder. Alternatively, agent polynucleotides or polypeptides may be introduced directly into an experimental animal, using any methods well known to those of ordinary skill in the art.

EXAMPLES

Example 1

Pain Sensitivity is regulated by the number of spinal cord immature neurons

The increase in the number of spinal cord immature neurons typically induces an increase in pain sensitivity. This idea was tested in commercially available Notch ko mice, which were analyzed for both pain sensitivity and the number of spinal cord immature neurons. Five Notch3 ko mice and five wild-type B6 mice, all male and 3 months old, were sacrificed by perfusion-fixation with 4% paraformaldehyde. The fixed spinal cords were removed, then were frozen in Tek-OCT, then sliced in a microtome. The 35 micrometer-thick spinal cord slices were blocked in 2% bovine serum albumin in PBS, then double stained for immature neuron marker Calretinin and for mature neuron marker NeuN, using secondary antibodies with different absorption wavelengths. The slices were visualized by immunofluorescence, and the numbers of Calretinin-positive and NeuN-positive cells in the spinal cord layers I-II, responsible for pain transmission, were determined. Statistical analysis was performed using 5 slices from each animal. In Notch3 ko mice, the number of mature neurons showed an 86% decrease, and the number of immature neurons showed a 214% increase relative to wild-type mice. Concurrently, 10 Notch3 ko mice and 10 wild-type mice were tested for mechanical pain sensitivity using a series of von-Frey filaments. Mechanical pain was tested weekly for 4 weeks. The pain threshold in wild-type mice was 1-1.5 grams, while in Notch3 ko mice the pain threshold was 0.03-0.06 grams, indicating that pain sensitivity was 17-50 fold higher in Notch3 ko mice. This example shows a parallel between pain sensitivity and the number of immature neurons.

Example 2

Chronic constriction injury of the sciatic nerve induces a simultaneous increase in the number of spinal cord immature neurons, and in pain sensitivity The idea that immature spinal cord neurons can contribute to pain was tested using a standard experimental animal model, the chronic constriction injury of the sciatic nerve (CCI). Fifteen two-month old rats were subjected to CCI under pentobarbital anesthesia. Three chromic gut ligature were tightly placed around the right sciatic nerve. Fifteen control rats were subjected to the same surgery, but without placing the ligatures (Sham). Mechanical pain sensitivity on the hind paws was tested weekly, using a set of calibrated von-Frey filaments applied to the plantar surface. Thermal pain sensitivity on the plantar surface was tested weekly by applying a beam of radiant heat. The results are shown in FIG. 7, for the ipsilateral paw (A, B) and for the contralateral paw (C, D). The side ipsilateral to the injured nerve shows a much larger increase in pain sensitivity relative to the contralateral side. At weeks 2, 4 and 6 after CCI, groups of three rats were sacrificed by perfusion-fixation under anesthesia, the spinal cords were removed, frozen, and sliced in 35 micrometer-thick slices. The slices were blocked in a 5% solution of bovine serum albumin, then incubated with primary antibodies for immature neuron markers nestin, Mash1, DCX and Notch3. The slices were then incubated with dye-linked secondary antibodies and imaged by immunofluorescence. The immunofluorescence images were quantified for marker expression in the ipsilateral and contralateral halves of the gray matter, using NIH-ImageJ. The quantification of nestin (FIG. 2), Mash1 (FIG. 3), DCX (FIG. 4) and Notch3 (FIG. 5) is shown. The increased expression of all 4 markers in the ipsilateral spinal cord after CCI indicates a larger number of immature neurons, and correlates with the increased pain sensitivity. The timing of the largest increase in the number of immature neurons at 6 weeks coincides with the timing of the second phase of pain sensitivity, indicating that long-term pain may be the result of immature neuron activity.

Example 3

A reduction in the number of spinal cord immature neurons results in reduced pain sensitivity The epidermal growth factor (EGF) and the fibroblast growth factor 2 (FGF2) are known to be necessary for neurogenesis and the production of new neurons. Therefore, a reduction in the number of immature neurons present in the spinal cord was achieved by reducing the effective intraspinal activity of FGF2 and EGF. FGF2 concentration was reduced using a FGF2-specific neutralizing antibody. EGF signaling was inhibited using erlotinib, an inhibitor of the EGF receptor. The FGF2 antibody (10 microliters, 0.2 miligrams/ml) and erlotinib (5 microliters, 1 miligram/ml) were injected together (INH, FIG. 8) into the spinal canal (intrathecal injection) every other day for the first 3 weeks after CCI, using a phosphate buffer saline (PBS) vehicle. Control rats were injected with PBS vehicle alone (Veh). INH and Veh were each injected in separate rat groups, both in Sham animals (Sham+INH and Sham+Veh) and in CCI animals (CCI+INH and CCI+Veh). Each treatment group consisted of 9 rats. The rats were tested weekly for nociceptive sensitivity to both mechanical (Von Frey method) and thermal (Hargreaves method) stimuli, over a period of 8 weeks. INH treatment reduced mechanical nociceptive sensitivity in both CCI and Sham rats (FIG. 8, B). INH treatment also reduced thermal nociceptive sensitivity in CCI rats (FIG. 8, C). At week 4 after CCI, 3 animals from each treatment group were sacrificed by perfusion-fixation, their spinal cords were harvested, frozen and sliced on a microtome into 35-micrometer thick slices. The slices were blocked in a solution of bovine serum albumin and Tween-20 in PBS, then stained with primary antibodies specific for immature neuron markers Mash1, DCX and Notch3, and with dye-linked secondary antibodies, then imaged by immunofluorescence. The expression of each marker was individually quantified by immunofluorescence in the ipsilateral and contralateral halves of the spinal cord gray matter. Statistical analysis was performed using 5 slices from each spinal cord. FIG. 8 (A) shows that the INH treatment prevented the CCI-induced increase normally observed in the expression of all three markers. This example indicates that a reduction in the number of spinal cord immature neurons results in a reduction of pain sensitivity.

Example 4

An increase in the number of spinal cord immature neurons induces increased pain sensitivity This example details an experiment opposite to Example 3. In order to stimulate spinal cord neurogenesis and increase the number of immature spinal cord neurons, recombinant FGF2 (10 microliters, 0.1 micrograms/ml) and EGF (5 microliters, 0.1 microgram/ml) were injected together (GF, FIG. 8) into the spinal canal (intrathecal injection) every other day for the first 3 weeks after CCI, using a phosphate buffer saline (PBS) vehicle. Control rats were injected with PBS vehicle alone (Veh). GF and Veh were each injected both in Sham animals (Sham+GF and Sham+Veh) and in CCI (CCI+GF and CCI+Veh) animals. Each treatment group consisted of 9 rats. The rats were tested weekly for nociceptive sensitivity to both mechanical (von Frey method) and thermal (Hargreaves method) stimuli, over a period of 8 weeks. GF treatment increased mechanical nociceptive sensitivity in both CCI and Sham rats (FIG. 8, D). GF treatment also increased short term thermal nociceptive sensitivity in both CCI and Sham rats (FIG. 8, E). At week 4 after CCI, 3 animals from each treatment group were sacrificed by perfusion-fixation, their spinal cords were harvested, frozen and sliced on a microtome into 35-micrometer thick slices. The slices were blocked in a solution of bovine serum albumin and Tween-20 in PBS, then stained with primary antibodies specific for immature neuron markers Mash1, DCX and Notch3, and with dye-linked secondary antibodies, then imaged by immunofluorescence. The expression of each marker was individually quantified by immunofluorescence in the ipsilateral and contralateral halves of the spinal cord gray matter. Statistical analysis was performed using 5 slices from each animal. FIG. 8 (A) depicts the increase in the expression of Mash1, DCX and Notch3 over the CCI-induced increase normally observed, caused by GF treatment. This example indicates that an increase in the number of spinal cord immature neurons results in an amplification of pain sensitivity.

Example 5

BDNF concurrently reduces the number of spinal cord immature neurons and pain sensitivity.

TrkB is a classical example of receptor that induces neuronal differentiation. At the same time, TrkB activation has been known to induce pain. Therefore, FIG. 9 depicts the testing of BDNF both as a promoter of neuronal differentiation and as a regulator of pain susceptibility. Two groups of 9 rats were subjected to CCI and two groups of 9 rats to Sham surgery. Immediately after surgery, BDNF (10 microliters, 5 microgram/ml) was injected in the spinal canal (intrathecally) every other day for 3 weeks, to one group of CCI (CCI+BDNF) and one group of Sham (Sham+BDNF) rats. The other 2 groups of rats were injected with Vehicle (PBS) alone (CCI+Veh and Sham+Veh). After 4 weeks, 3 rats in each group were sacrificed by perfusion-fixation, the spinal cords were collected and sliced into 35 micrometer-thick slices. The slices were blocked in 2% BSA, then stained with primary antibodies for Mash1, DCX and Notch3, and with a dye-linked secondary antibody. The slices were imaged by immunofluorescence microscopy, and the stained areas were quantified for the ipsilateral and contralateral halves of the gray matter, using NIH-ImageJ. Statistical analysis was performed using 5 slices from each rat. FIG. 9 (A) depicts the effect of BDNF as a promoter of neuronal differentiation, by reducing the expression of all three markers. BDNF induced the immature neurons that express Mash1, DCX and Notch3 to undergo accelerated differentiation, which is expected to result in a reduced excitability. The same groups of rats were concurrently tested for pain sensitivity, using the von Frey method for mechanical pain and the Hargreaves method for thermal pain. FIG. 9 (B) depicts the long-term increase in mechanical pain threshold (decrease in pain sensitivity) caused by BDNF in both CCI and Sham rats. Although the BDNF treatment was applied for only 3 weeks, the decrease in pain lasted for 3 months because the immature neurons with high excitability, which regulate pain levels, are regenerated at a slow rate. The BDNF treatment increased long-term thermal pain sensitivity (FIG. 9, C) probably by reducing the number of inhibitory neurons involved in thermal pain transmission.

Example 6

Delayed BDNF treatment after CCI produces a brief, short-term increase in pain sensitivity, followed by a long-term decrease in pain The same experiments detailed in Example 5 were repeated, with the only modification that the BDNF treatment was delayed for 3 weeks after CCI. In this case, BDNF administration first induced a 2-3 day increase in both mechanical and thermal pain sensitivity, followed by a long-term decrease in pain sensitivity (FIG. 9, D,E). The 3 week delay in BDNF administration allowed an initial accumulation of neural progenitor cells, as depicted in FIGS. 1-4. Upon BDNF administration, all the neural stem cells present were induced to differentiate synchronously, first generating a large number of highly excitable immature neurons, which were responsible for the initial brief increase in pain sensitivity. These immature neurons continued to mature into low-excitable mature neurons, which were responsible for the long-term decrease in pain sensitivity (increased pain threshold to pain). This example confirmed that immature neurons are responsible for the regulation of pain, and explains why BDNF has been considered to be an inducer of pain.

Example 7

DHF concurrently reduces the number of spinal cord immature neurons and pain sensitivity.

The same experiments described in Example 5 were repeated with the modification that DHF was used instead of BDNF as a TrkB ligand. FIG. 10 depicts the testing of DHF both as a promoter of neuronal differentiation and as a regulator of pain. Two groups of 9 rats were subjected to CCI and two groups of 9 rats to Sham surgery. Immediately after surgery, DHF (1 ml, 70 miligram/ml) was injected intraperitoneally every other day for 3 weeks, to one group of CCI (CCI+DHF) and one group of Sham (Sham+DHF) rats. The other 2 groups of rats were injected with Vehicle (PBS) alone (CCI+Veh and Sham+Veh). After 4 weeks, 3 rats in each group were sacrificed by perfusion-fixation, the spinal cords were collected and sliced into 35 micrometer-thick slices. The slices were blocked in 2% BSA, then stained with primary antibodies for Mash1, DCX and Notch3, and with a dye-linked secondary antibody. The slices were imaged by immunofluorescence microscopy, and the stained areas were quantified for the ipsilateral and contralateral halves of the gray matter, using NIH-ImageJ. Statistical analysis was performed using 5 slices from each rat. FIG. 10 (A) depicts the effect of DHF as a promoter of neuronal differentiation, by reducing the expression of all three markers. The same groups of rats were concurrently tested for pain sensitivity, using the von Frey method for mechanical pain and the Hargreaves method for thermal pain. FIG. 10 (B) depicts the long-term increase in mechanical pain threshold (decrease in pain sensitivity) caused by DHF in both CCI and Sham rats. Although the DHF treatment was applied for only 3 weeks, the decrease in pain lasted for 3 months. The DHF treatment increased long-term thermal pain sensitivity (FIG. 9, C) probably by reducing the production of inhibitory neurons involved in thermal pain transmission.

Example 8

Delayed DHF treatment after CCI produces a brief short-term increase in pain sensitivity, followed by a long-term decrease in pain The same experiments detailed in Example 7 were repeated, with the only modification that the DHF treatment was delayed for 3 weeks after CCI. In this case, DHF administration first induced a 2-3 days increase in both mechanical and thermal pain sensitivity, followed by a long-term decrease in pain sensitivity (FIG. 10, D,E). The 3 week delay in BDNF administration allowed an initial accumulation of neural progenitor cells, as depicted in FIGS. 1-4. Upon DHF administration, all the neural stem cells present were induced to differentiate synchronously, first generating a large number of highly excitable immature neurons, which were responsible for the initial brief increase in pain sensitivity. These immature neurons continued to mature into low-excitable mature neurons, which were responsible for the long-term decrease in pain sensitivity (increased pain threshold to pain). This example confirmed that DHF can be used in an animal to treat pain.

Example 9

Use of Dihexa to treat pain in a human

Dihexa (N-hexanoic-Tyr-Ile-(6)aminohexanoic amide), an activator of c-Met receptor, is administered orally, 200 miligrams/day for 4 weeks, to a human for the purpose of treating pain. The subject is having chronic pain for the previous 6 months, as a result of injury. Before the beginning of treatment, and weekly thereafter for 6 months, the subject is tested for pain levels using a combination of subjective (numeric rating scale) and physiological (dolorimetric) evaluation methods. After 2 weeks of treatment the subject may report decreased pain. After 4 weeks of treatment, the subject may report that pain sensitivity is back to normal levels. Increased pain sensitivity may reoccur after 3 months, and then the treatment may be repeated.

Example 10

Combined use of NT4 and a flavone to treat pain in a human NT4 is a TrkB ligand and inducer of neuronal differentiation that may be used to treat pain. NT4 (200 microliters, 1 microgram/ml) is injected every other day for 3 weeks (10 injections total) into the spinal canal of a human patient diagnosed with fibromyalgia. The patient may report increased pain after 4-5 days, but the increase in pain subsides after 7-10 days with continued treatment. The patient may report decreased pain after 2 weeks, and no pain after 3-4 weeks. To prevent pain reoccurrence, a maintenance dose of 7,8-dihydroxy-4'-dimethylaminoflavone-8-O-glucozide (3-4 grams per day for 4-5 consecutive days) may be administered every month.

REFERENCES

Arnold L M, et al. (2013) The fibromyalgia family study: a genome-wide linkage scan study. Arthritis Rheum. 65, 1122-8.

Babcock D T, et al. (2011) Hedgehog signaling regulates nociceptive sensitization. Curr Biol. 21, 1525-1533.

Belleau M L, Warren R A. (2000) Postnatal development of electrophysiological properties of nucleus accumbens neurons. J Neurophysiol. 84, 2204-16.

Ben-Ari Y, et al. (2007) GABA; a pioneer transmitter that excites immature neurons and generates primitive oscillations. Physiol Rev. 87, 1215-84.

Bennett G J, Xie Y K. (1988) A peripheral mononeuropathy in rat that produces disorders of pain sensation like those seen in man. Pain 33, 87-107.

Bertrand N, et al. (2002) Proneural genes and the specification of neural cell types. Nat Rev Neurosci. 3: 517-30.

Bragina O, et al. (2010) Smoothened agonist augments proliferation and survival of neural cells. Neurosci. Lett. 482, 81-5.

Brown J P, et al. (2003) Transient expression of doublecortin during adult neurogenesis. J Comp Neurol. 467: 1-10.

Burnett B P, et al. (2007). A medicinal extract of Scutellaria baicalensis and Acacia catechu acts as a dual inhibitor of cyclooxygenase and 5-lipoxygenase to reduce inflammation. J Med Food. 10, 442-451.

Chi L, et al. (2006) Motor neuron degeneration promotes neural progenitor cell proliferation, migration, and neurogenesis in the spinal cords of amyotrophic lateral sclerosis mice. Stem Cells 24, 34-43.

Danilov A I, et al. (2006) Neurogenesis in the adult spinal cord in an experimental model of multiple sclerosis. Eur J Neurosci. 23, 394-400.

Dessaud E, et al., (2008) Pattern formation in the vertebrate neural tube: a sonic hedgehog morphogen-regulated transcriptional network. Development. 135, 2489-503.

Engert S, et al. (2008) Leukemia inhibitory factor differentially regulates capsaicin and heat sensitivity in cultured rat dorsal root ganglion neurons. Neuropeptides 42, 193-7.

Girija K, et al. (2002) Anti-nociceptive effect of synthesized dihydroxy flavones: possible mechanism. Indian J Exp Biol. 40, 1314-6.

Hadari Y R, et al. (1998) Binding of Shp2 tyrosine phosphatase to FRS2 is essential for fibroblast growth factor-induced PC12 cell differentiation. Mol Cell Biol. 18, 3966-73.

Hagenacker T, et al. (2010) Anti-allodynic effect of the flavonoid myricetin in a rat model of neuropathic pain: Involvement of p38 and protein kinase C mediated modulation of Ca(2)+ channels. Eur J Pain. 14, 992-998.

Horner, P J, et al. (2000) Proliferation and differentiation of progenitor cells throughout the intact adult rat spinal cord. J Neurosci. 20, 2218-28.

Hugnot J P, Franzen R. (2011) The spinal cord ependymal region: a stem cell niche in the caudal central nervous system. Frontiers Biosci. 16, 1044-59.

Inestrosa N C, Varela-Nallar L. (2015) Wnt signalling in neuronal differentiation and development. Cell Tissue Res. 359, 215-23.

Jang S W, et al. (2010) A selective TrkB agonist with potent neurotrophic activities by 7,8-dihydroxyflavone. Proc Natl Acad Sci USA. 107: 2687-92.

Jang S W, et al. (2010) Deoxygedunin, a natural product with potent neurotrophic activity in mice. PLOS One 5:e11528.

Jankowski M P, Koerber H R. (2010) Neurotrophic Factors and Nociceptor Sensitization. In: Kruger L, Light A R, editors. Translational Pain Research: From Mouse to Man, Chapter 2, Boca Raton, Fla.: CRC Press/Taylor & Francis.

Khan N, Smith M T. (2015) Neurotrophins and Neuropathic Pain: Role in Pathobiology. Molecules 20, 10657-88.

Lewin G R, Mendell L M. (1993) Nerve growth factor and nociception. Trends Neurosci. 16, 353-359.

Li J M, et al. (2007) Angiotensin II-induced neural differentiation via angiotensin II type 2 (AT2) receptor-MMS2 cascade involving interaction between AT2 receptor-interacting protein and Src homology 2 domain-containing protein-tyrosine phosphatase 1. Mol Endocrinol. 21, 499-511.

Lippoldt E K, et al. (2016) Inflammatory and neuropathic cold allodynia are selectively mediated by the neurotrophic factor receptor GFRα3. Proc Natl Acad Sci USA. 113:4506-11.

Liu S, et al. (2015) Wnt/Ryk signaling contributes to neuropathic pain by regulating sensory neuron excitability and spinal synaptic plasticity in rats. Pain 156, 2572-84.

Liu X, et al. (2010) A synthetic 7,8-dihydroxyflavone derivative promotes neurogenesis and exhibits potent antidepressant effect. J Med Chem. 53, 8274-8286.

LoTurco J J, et al. (1995) GABA and glutamate depolarize cortical progenitor cells and inhibit DNA synthesis. Neuron. 15, 1287-1298.

Lu Y, et al. (2008) Spinal cord injury-induced attenuation of GABAergic inhibition in spinal dorsal horn circuits is associated with down-regulation of the chloride transporter KCC2 in rat. J Physiol. 586, 5701-15.

Marion E, et al. (2014) Mycobacterial toxin induces analgesia in buruli ulcer by targeting the angiotensin pathways. Cell 157, 1565-1576.

Majumder A, et al. (2012) Neurotrophic effects of leukemia inhibitory factor on neural cells derived from human embryonic stem cells. Stem Cells 30, 2387-99.

Massa S M, et al. (2010) Small molecule BDNF mimetics activate TrkB signaling and prevent neuronal degeneration in rodents. J Clin Invest. 120, 1774-85.

Merighi A. (2016) Targeting the glial-derived neurotrophic factor and related molecules for controlling normal and pathologic pain. Expert Opin Ther Targets 20, 193-208.

Milenkovic N, et al. (2007) Nociceptive tuning by stem cell factor/c-Kit signaling. Neuron 56, 893-906.

Mowla S J, et al. (2001) Biosynthesis and Post-translational Processing of the Precursor to Brain-derived Neurotrophic Factor. J Biol Chem. 276, 12660-12666.

Pandurangan et al. (2014) Antinociceptive effect of certain dimethoxy flavones. Eur J Pharmacol. 727, 148-57.

Pankratova et al. (2010) Neuroprotective properties of a novel, non-haematologic agonist of the erythropoietin receptor.Brain 133, 2281-94.

Price T J, et al. (2005) Role of cation-chloride-cotransporters (CCC) in pain and hyperalgesia. Curr Top Med Chem. 5, 547-55.

Ramaswamy S, et al. (1985) Analgesic effect of 0-(beta-hydroxy ethyl)rutoside in mice. Indian J Exp Biol. 23, 219-20.

Ren K, Dubner R. (2010) Interactions between the immune and nervous systems in pain. Nat Med. 16, 1267-76.

Rokyta R, Fricová J. (2012) Ontogeny of the pain. Physiol Res. 61 Suppl 1:S109-22.

Rusanescu G, et al. (2014) Notch3 is necessary for neuronal differentiation and maturation in the adult spinal cord. J Cell Mol Med. 18, 2103-16.

Rusanescu G, et al. (2015) Adult spinal cord neurogenesis is a dynamic regulator of nociceptive sensitivity, J Cell Mol Med. 19, 2352-2364.

Rylski M, et al. (1979) The analgesic action of some flavonoids in the hot plate test. Acta Physiol Pol. 30, 385-388.

Schechter R, et al. (2007) New GABAergic interneurons supported by myelin-specific T cells are formed in intact adult spinal cord. Stem Cells 25, 2277-2282.

Seidah N G, et al. (1996) Cellular processing of the neurotrophin precursors of NT3 and BDNF by the mammalian proprotein convertases. FEBS Lett. 379, 247-250.

Seidah N G, et al. (1996) Cellular processing of the nerve growth factor precursor by the mammalian pro-protein convertases. Biochem J. 314, 951-960.

Shelton D. (2014) Development of nerve growth factor (NGF) inhibition as a strategy for treatment of pain. J Peripher Nery Syst. 19 Suppl 2:S12-3.

Shi Y, et al. (2012) Regulation of Wnt signaling by nociceptive input in animal models. Mol Pain 8, 47.

Shi Y, et al. (2012) Analgesic and uterine relaxant effects of isoliquiritigenin, a flavone from *Glycyrrhiza glabra*. Phytother Res. 26, 1410-7.

Thirugnanasambantham P, et al. (1990) Analgesic activity of certain flavone derivatives: a structure-activity study. J Ethnopharmacol. 28, 207-14.

Thirugnanasambantham P, et al. (1993) Analgesic activity of certain flavone derivatives: a structure-activity study. Clin Exp Pharmacol Physiol. 20, 59-63.

Thompson S W, et al. (1996) Leukemia inhibitory factor induces mechanical allodynia but not thermal hyperalgesia in the juvenile rat. Neuroscience 71, 1091-1094.

Vegunta S, et al. (2015) Chronic pain in Noonan syndrome: A previously unreported but common symptom. Am J Med Genet A. 167A, 2998-3005.

Vescovi A L, et al. (1993) bFGF regulates the proliferative fate of unipotent (neuronal) and bipotent (neuronal/astroglial) EGF-generated CNS progenitor cells. Neuron 11, 951-66.

Vidyalakshmi K, et al. (2010) Antinociceptive effect of certain dihydroxy flavones in mice. Pharmacol Biochem Behay. 96, 1-6.

Viswanathan S, et al. (1984) Gossypin-induced analgesia in mice. Eur J Pharmacol. 98, 289-94.

Wallén A, et al. (1999) Fate of mesencephalic AHD2-expressing dopamine progenitor cells in NURR1 mutant mice. Exp Cell Res. 253, 737-46.

Wu, X., et al. (2004) Purmorphamine induces osteogenesis by activation of the hedgehog signaling pathway. Chem Biol. 11, 1229-1238.

Yamada J, et al. (2004) Cl-uptake promoting depolarizing GABA actions in immature rat neocortical neurones is mediated by NKCC1. J Physiol. 557(Pt 3), 829-41.

Yang X, et al. (2014) Reversal of bone cancer pain by HSV-1-mediated silencing of CNTF in an afferent area of the spinal cord associated with AKT-ERK signal inhibition. Curr Gene Ther. 14, 377-88.

Yu Q, et al. (2012) 7,8,3'-Trihydroxyflavone, a potent small molecule TrkB receptor agonist, protects spinal ganglion neurons from degeneration both in vitro and in vivo. Biochem Biophys Res Comm. 422, 387-92.

Yunus M, et al. (1999) Genetic linkage analysis of multicase families with fibromyalgia syndrome. J Rheumatol. 26, 408-12.

Zambelli V O, et al. (2014) Aldehyde dehydrogenase-2 regulates nociception in rodent models of acute inflammatory pain. Sci Transl Med. 6, 251ra118.

Zhang Z J, Sieber-Blum M. (2009) Essential role of stem cell factor signaling in primary sensory neuron development. Dev Neurosci. 31, 202-11.

Zurn A D, et al. (1996) Combined effects of GDNF, BDNF and CNTF on motor neuron differentiation in vivo. J Neurosci Res. 44, 133-41.

---

The invention claimed is:

1. A method of treating chronic pain in an individual, comprising the administration to the individual of a therapeutically effective amount of a polypeptide having at least 95% sequence identity to SEQ ID NO:1, wherein chronic pain is the result of mechanical injury, metabolic disfunction, genetic variations or other unknown causes, as defined in the specification, and the therapeutically effective amount is an amount sufficient to cause a detectable decrease in pain, as determined by a pain or nociception measurement method.

2. The method of claim 1, wherein the polypeptide has the amino acid sequence of SEQ ID NO:1.

3. The method of claim 1, wherein the polypeptide has the ability to activate TrkB receptors.

* * * * *